(12) United States Patent
Zhang et al.

(10) Patent No.: US 10,815,226 B2
(45) Date of Patent: Oct. 27, 2020

(54) HETEROARYL COMPOUNDS AS INHIBITORS OF NECROSIS, COMPOSITION AND APPLICATION THEREOF

(71) Applicants: Xiaohu Zhang, Suzhou (CN); ACCRO BIOSCIENCE INC., Grand Cayman (KY)

(72) Inventors: Xiaohu Zhang, Suzhou (CN); Haikuo Ma, Suzhou (CN); Jiyue Zheng, Suzhou (CN); Sudan He, Suzhou (CN)

(73) Assignee: ACCRO BIOSCIENCE INC., Grand Cayman (KY)

( * ) Notice: Subject to any disclaimer, the term of this patent is extended or adjusted under 35 U.S.C. 154(b) by 0 days.

(21) Appl. No.: 16/319,337

(22) PCT Filed: Jul. 15, 2017

(86) PCT No.: PCT/US2017/042283
§ 371 (c)(1),
(2) Date: Jan. 19, 2019

(87) PCT Pub. No.: WO2018/017435
PCT Pub. Date: Jan. 25, 2018

(65) Prior Publication Data
US 2019/0284180 A1    Sep. 19, 2019

(30) Foreign Application Priority Data

Jul. 22, 2016   (CN) .......................... 2016 1 0581012
Jun. 21, 2017   (CN) .......................... 2017 1 0473744

(51) Int. Cl.
| | | |
|---|---|---|
| C07D 495/04 | (2006.01) | |
| C07D 487/04 | (2006.01) | |
| C07D 471/04 | (2006.01) | |
| C07D 417/04 | (2006.01) | |
| C07D 417/10 | (2006.01) | |
| C07D 417/14 | (2006.01) | |
| C07D 401/04 | (2006.01) | |

(52) U.S. Cl.
CPC ......... *C07D 417/10* (2013.01); *C07D 401/04* (2013.01); *C07D 417/04* (2013.01); *C07D 417/14* (2013.01); *C07D 471/04* (2013.01); *C07D 487/04* (2013.01); *C07D 495/04* (2013.01)

(58) Field of Classification Search
CPC .......... A61P 25/28; A61P 29/00; A61P 35/00; C07D 401/04; C07D 417/04; C07D 417/10; C07D 417/14; C07D 471/04; C07D 487/04; C07D 495/04
See application file for complete search history.

(56) References Cited

U.S. PATENT DOCUMENTS

2011/0178070 A1    7/2011   Gong et al.
2016/0046616 A1*   2/2016   Biswal ............... A61K 31/7048
                                                            514/156

OTHER PUBLICATIONS

Yang, et al, Discovery of a 6-(pyridin-3-yl)benzo[d]thiazole template for optimization of hedgehog and PI3K/AKT/mTOR dual inhibitors, Bioorganic & Medicinal Chemistry Letters, 25(17), 3665-3670(2015). (Year: 2015).*

* cited by examiner

*Primary Examiner* — Erich A Leeser
(74) *Attorney, Agent, or Firm* — Feng Tian

(57) ABSTRACT

The present disclosure provides heteroaryl compounds of formulas I, Ia and Ib, processes for their preparation, pharmaceutical compositions containing them, and their use in the treatment of diseases and disorders, arising from or related to necrosis.

19 Claims, 2 Drawing Sheets

HETEROARYL COMPOUNDS AS INHIBITORS OF NECROSIS, COMPOSITION AND APPLICATION THEREOF

CROSS REFERENCE TO RELATED APPLICATIONS

This application claims the benefit of Chinese Patent Applications 210610581012.7, filed on Jul. 22, 2016; and 201710473744.9, filed on Jun. 21, 2017; all of which are hereby incorporated by reference.

FIELD OF INVENTION

The present invention generally relates to heteroaryl compounds and, more particularly, relates to novel heteroaryl compounds that are useful in the therapies targeting necrosis mediated diseases, including inflammatory diseases, tumors, metabolic diseases, and neurodegenerative diseases such as cerebral ischemia and stroke, in mammals.

BACKGROUND OF THE INVENTION

Different types of cell death are often defined by morphological criteria, and are classified as apoptosis and necrosis, two of the basic types. Apoptosis is characterized by cell shrinkage, chromatin condensation, the increased activities of cysteinyl aspartate-specific proteases or caspases, and the controlled breakdown of the cell into apoptotic bodies. Because apoptosis is usually physiological aberrations, it is not inflammatory. Necrosis is thought to begin with an impairment of the cell's ability to maintain homeostasis, continue to cause damage of the plasma membrane integrity, and lead to cytoplasmic and organelle swelling and the eventual lysis of the cell. Due to the release of cytoplasmic contents into the surrounding extracellular space, necrosis usually results in inflammatory response.

Early studies considered necrosis as an accidental and uncontrolled form of cell death lacking underlying signaling events. But later studies has shown that when stimulated by proinflammatory cytokins such as tumor necrosis factor-α (TNF-α), some cells choose the necrotic pathway instead of the apoptotic pathway. Such cell types include L929 murine fibroblasts and the NIH 3T3N murine fibroblasts. Recent research on the function of RIP1/RIP3 in TNF-α promoted necrosis pathway laid the foundation to elucidate the mechanism of necrosis. See Cho Y. S. et al., *Cell* 2009; 137(6): 1112-23; Zhang D. W. et al., *Science* 2009, 325(5938): 332-6; He, S. et al., *Nat. Immunolo. Cell* 2009; 137(6): 1100-11.

For example, some lethal stimuli can induce either apoptosis or necrosis, depending on the cell type and/or experimental setting. Regarding the molecular bases of this phenomenon, two members of the receptor-interacting protein kinase (RIP) family, RIP1 and RIP3, have been demonstrated to control the switch between apoptotic and necrotic cell death. When the apoptosis pathway is malfunctioned or inhibited, the nectosis pathway can be activated. This regulated necrotic cell death, or necroptosis, can be mediated by the interaction of activated RIP3 and mixed lineage kinase like (MLKL). RIP1 can induce the function of RIP3 to promote necroptosis while the proteolytic activity of a ripotosome complex formed by RIP1, fas-associating death domain (FADD) and caspase-8 can antagonize the necroptosis promotion activities of RIP3. Upon RIP3 phosphoraylation of Thr357 and Ser358 in MLKL, human MLKL shifts from its monomeric state to an active oligomeric state. The ologomeric MLKL can bind to phosphoinositol and myocardial phospholipid so that the necrosome complex can move from cytomplasm to cell membrane or organelle membrane, and form permeable channels in the memberance structure, destroy the membrane integrity, and induce cell death.

In addition, phosphorylated RIP3 can interact with downstream bioenergetics enzymes including glycogen phosphorylase (PYGL), glutamate-ammonia ligase (GLUL) and glutamate dehydrogenase 1 (GLUD1), thereby enhancing their catalytic activity. Enhanced glycogenolysis and glutaminolysis can provide additional respiratory substrates, such as phosphorylated glucose and keoglutarate, accelerate mitochondrial citric acid cycle, and ultimately result in the overgeneration of reactive oxygen species (ROS). Excess ROS, in turn, can trigger mitochondrial membrane permeabilization (MMP), thereby mediating TNF-induced programmed necrosis. Therefore, inhibition of necrosis may become a potential target for the treatment of metabolic diseases, such as diabetes.

Programmed necrosis may be involved in cell death associated with lesions of neurons and glial cells—the most essential components of the central nervous system. Many research projects indicate that inhibition of programmed necrosis may protect the nervous system. Some research programs seek to reduce harms to nervous system by reversing the necrosis and mitigating tissue damage. Accordingly, inhibition of necrosis often becomes the target of treatment for injuries to the nervous system. For example, in ischemic stroke, loss of cerebral circulation may lead to local or total cerebral ischemia and hypoxia. The ensuing death of large number of neurons may affect their corresponding nerve motor function. Consequently reducing the death of neurons may become the objective for the treatment of ischemic stroke.

Accordingly, in order to improve the afore-mentioned diseases caused by necrosis, there is a need for effective inhibitors of necrosis.

SUMMARY OF THE INVENTION

The present disclosure provides heteroaryl compounds as inhibitors of necrosis, and compositions and applications thereof. These disclosed heteroaryl compounds, and compositions and applications thereof, may effectively inhibit necrosis, thereby finding application in treatments of necrotic pathway-related diseases and disorders, including, for example, inflammation, tumors, metabolic diseases and neurodegenerative diseases such as cerebral ischemia and stroke.

An aspect of the present disclosure provides a compound of formula (I):

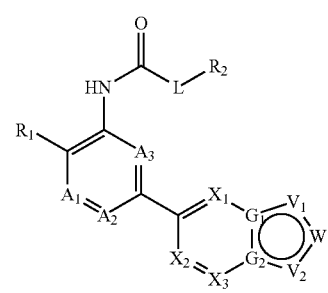

or a pharmaceutically acceptable salt, solvate, stereoisomer or a tautomer thereof, wherein $A_1$, $A_2$ and $A_3$ are independently N or $CR_3$;

$X_1$, $X_2$ and $X_3$ are independently N or $CR_4$;

$G_1$ and $G_2$ are independently N or C;

$V_1$ and $V_2$ are independently N, O, S, $NR_5$ or $CR_3$;

W is $V_3$, $V_4$-$V_5$, or $V_4$=$V_5$, $V_3$, $V_4$ and $V_5$ are independently N, O, S, or $CR_6$, wherein $V_4$ connects with $V_1$, and $V_5$ connects with $V_2$;

L is none, O, S, $NR_{12}$ or $CR_{12}R_{13}$;

$R_1$ is H, deuterium, halide, amino, —$NO_2$, —OH, —SH, —CN, $C_{1-6}$ alkyl, $C_{3-6}$ cycloalkyl, $C_{1-6}$ alkoxy, $C_{2-6}$ alkenyl, or $C_{2-6}$ alkynyl, wherein $C_{1-6}$ alkyl, $C_{3-6}$ cycloalkyl, $C_{1-6}$ alkoxy, $C_{2-6}$ alkenyl, $C_{2-6}$ alkynyl are unsubstituted or substituted with 1 to 3 groups selected from halide, deuterium, —CN, —$CF_3$, $C_{1-6}$ alkyl, $C_{3-6}$ cycloalkyl and $C_{1-6}$ alkoxy;

$R_2$ is $C_{1-6}$ alkyl, $C_{3-8}$ cycloalkyl, $C_{6-12}$ spirocycle, phenyl, 5-6 membered heteroaryl comprising 1-3 hetero atoms, 3-8 membered heterocycle comprising 1-3 hetero atoms, or 6-12 membered heterospirocycle comprising 1-3 hetero atoms, all of which are unsubstituted or substituted with 1-3 $R_9$, wherein each hetero atom is independently N, O or S;

each of $R_3$, $R_4$ and $R_5$ is independently selected from the group consisting of H, deuterium, halide, amino, —OH, —CN, $C_{1-6}$ alkoxy, $C_{1-6}$ alkylthio, $C_{3-6}$ cycloalkyl or $C_{1-6}$ alkyl;

$R_6$ is H, deuterium, halide, —OH, —CN, $C_{1-6}$ alkoxy, $C_{1-6}$ alkyl; $C_{3-6}$ cycloalkyl or —$NR_7R_8$;

$R_7$ is H, $C_{1-6}$ alkyl or $C_{3-6}$ cycloalkyl;

$R_8$ is H, C(O)$R_{10}$, C(O)$NR_{10}R_{11}$, C(O)O$R_{10}$, S(O)$_2R_{10}$, S(O)$_2NR_{10}R_{11}$, $C_{1-6}$ alkyl, $C_{3-6}$ cycloalkyl, $C_{2-6}$ alkenyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, phenyl, 3-6 membered heterocycle and 5-6 membered heteroaryl is unsubstituted or substituted with 1-3 groups selected from the group consisting of halide, deuterium, —CN, $C_{1-6}$ alkyl, $C_{3-6}$ cycloalkyl, $C_{1-6}$ alkoxy and 3-6 membered heterocycle comprising 1-3 hetero atoms, each hetero atom is independently N, O or S;

$R_9$ is H, deuterium, halide, —OH, oxy, —CN, -amino, $C_{1-6}$ alkyl, $C_{3-6}$ cycloalkyl or $C_{1-6}$ alkoxy, wherein each of $C_{1-6}$ alkyl, $C_{3-6}$ cycloalkyl, and $C_{1-6}$ alkoxy is unsubstituted or substituted with 1-3 groups selected from the group consisting of halide, deuterium, and $C_{1-3}$ alkyl;

each of $R_{10}$ and $R_{11}$ is independently H, $C_{1-6}$ alkyl, $C_{3-6}$ cycloalkyl, $C_{2-6}$ alkenyl, $C_{2-6}$ alkynyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, $C_{2-6}$ alkenyl, $C_{2-6}$ alkynyl, phenyl, 3-6 membered heterocycle and 5-6 membered heteroaryl is unsubstituted or substituted with 1-3 groups selected from the group consisting of halide, deuterium, —CN, —OH, —$CF_3$, $C_{1-6}$ alkyl, $C_{3-6}$ cycloalkyl, $C_{1-6}$ alkoxy and 5-6 membered heteroaryl comprising 1-3 hetero atoms, each hetero atom is independently N, O or S; or $R_{10}$ and $R_{11}$ together, with nitrogen atom they attached to, form a first 5-6 membered ring; or $R_{10}$ and $R_5$ together, with adjacent atoms they attached to, form a second 5-6 membered ring;

$R_{12}$ and $R_{13}$ are independently H, deuterium, halide, —OH, $C_{1-3}$ alkyl or $C_{1-6}$ alkoxy.

In some embodiments of aspects provided herein, $A_3$ is CH, W is C—$NR_7R_8$ to afford a structure shown in Formula Ia:

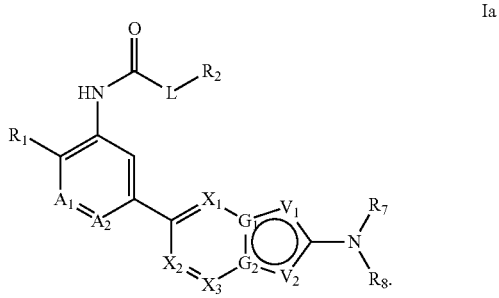

In some embodiments of aspects provided herein, sub-group

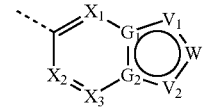

is selected from the group consisting of:

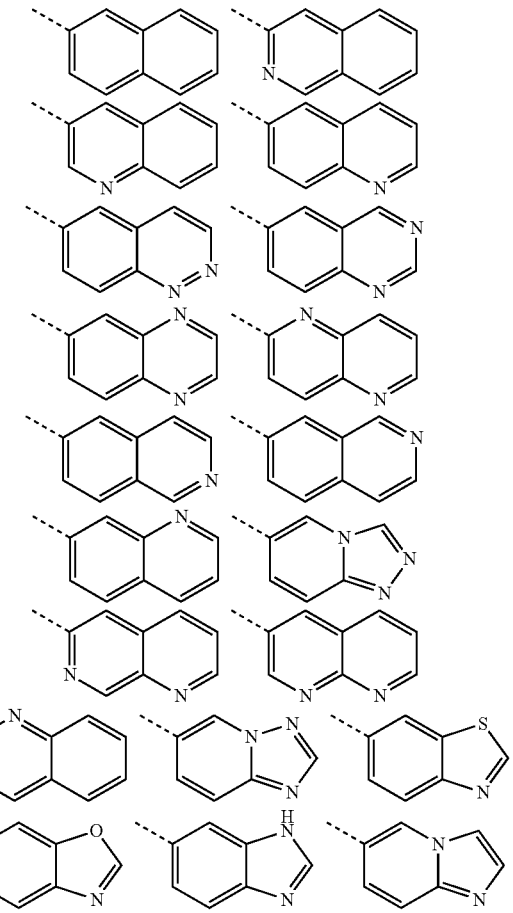

-continued

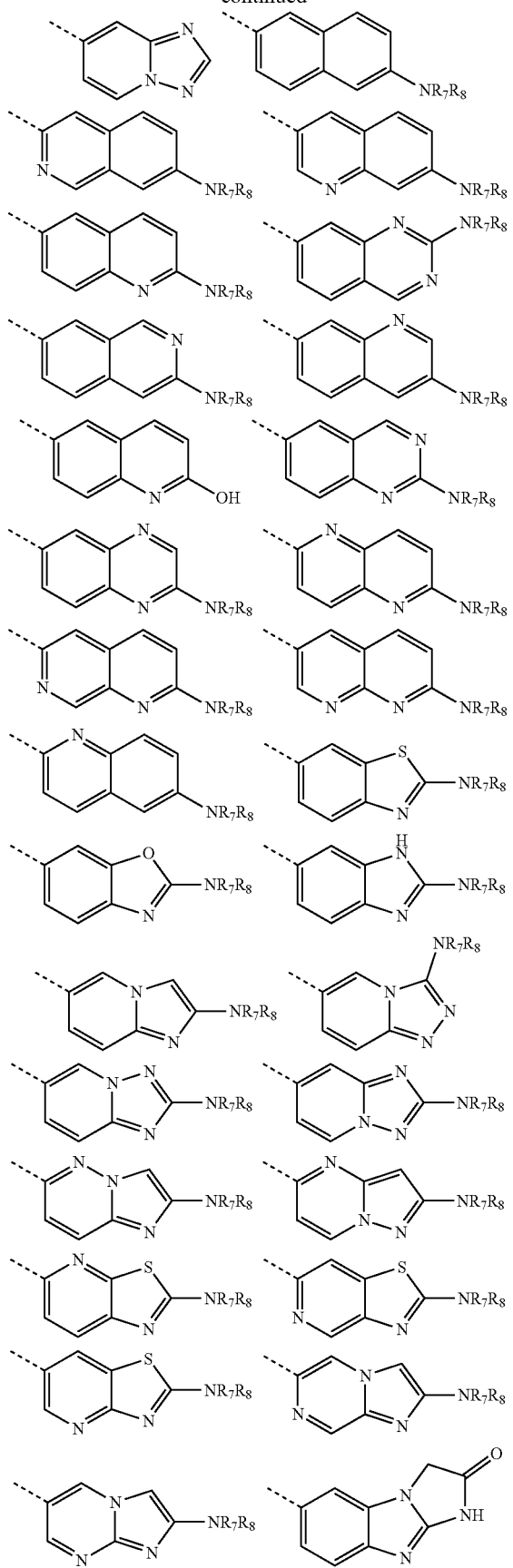

-continued

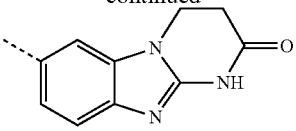

unsubstituted or substituted by 1-3 groups independently selected from the group consisting of H, deuterium, halide, amino, —OH, —CN, $C_{1-6}$ alkoxy, $C_{1-6}$ alkylthio, $C_{3-6}$ cycloalkyl and $C_{1-6}$ alkyl.

In some embodiments of aspects provided herein, subgroup

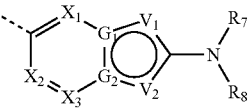

is selected from the group consisting of:

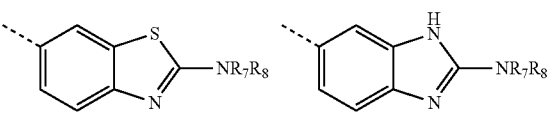

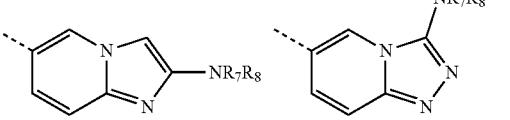

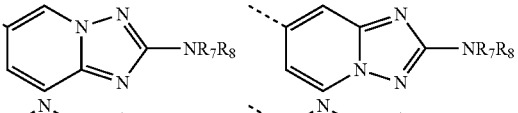

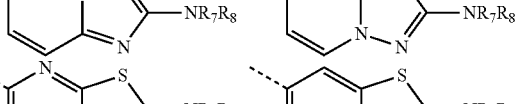

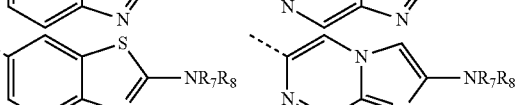

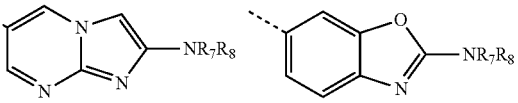

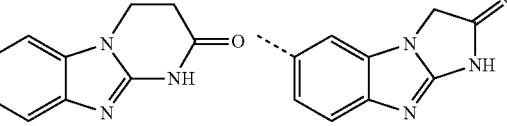

unsubstituted or substituted by 1-3 groups independently selected from the group consisting of H, deuterium, halide, amino, —OH, —CN, $C_{1-6}$ alkoxy, $C_{1-6}$ alkylthio, $C_{3-6}$ cycloalkyl and $C_{1-6}$ alkyl.

In some embodiments of aspects provided herein, L is none, $CH_2$, O or NH. In some embodiments of aspects provided herein, $R_2$ is selected from the group consisting of:

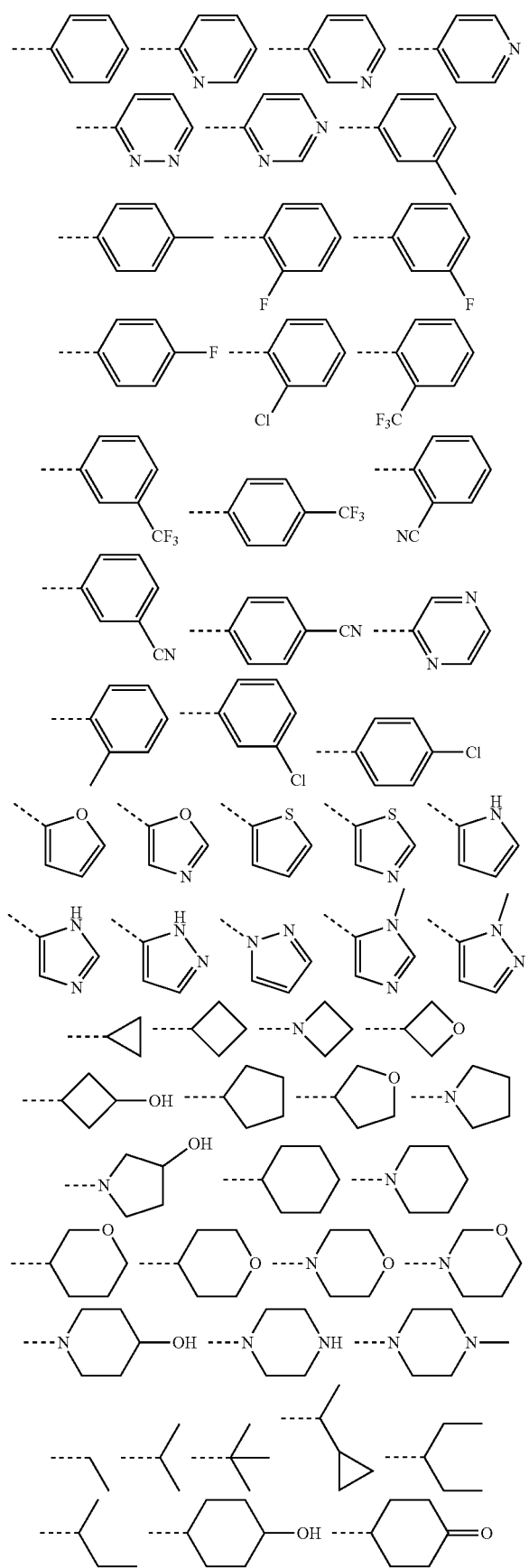
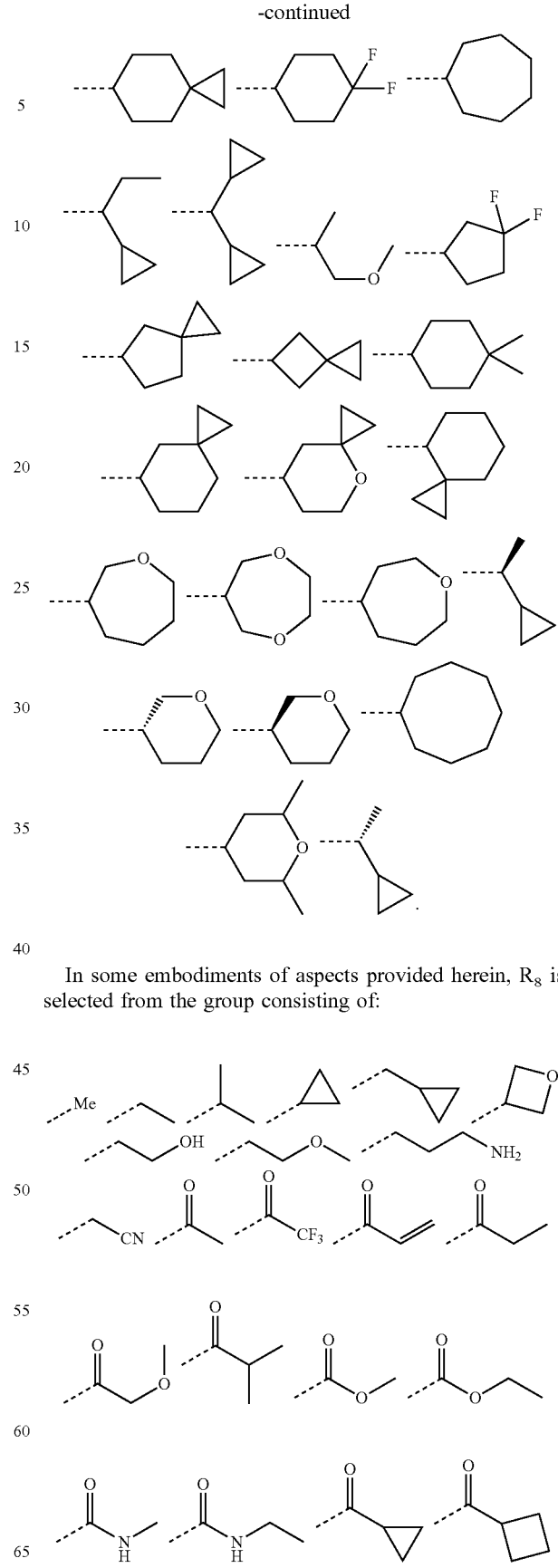
-continued
In some embodiments of aspects provided herein, $R_8$ is selected from the group consisting of:

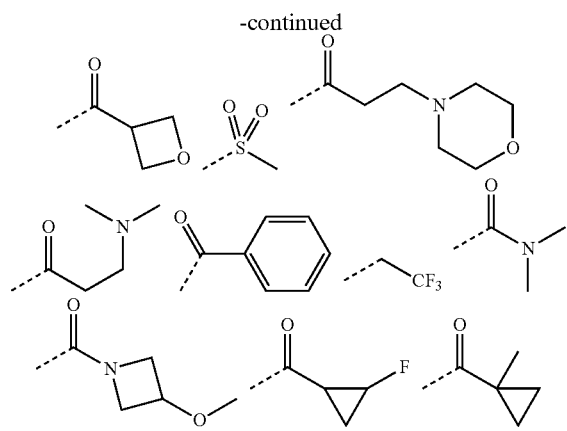
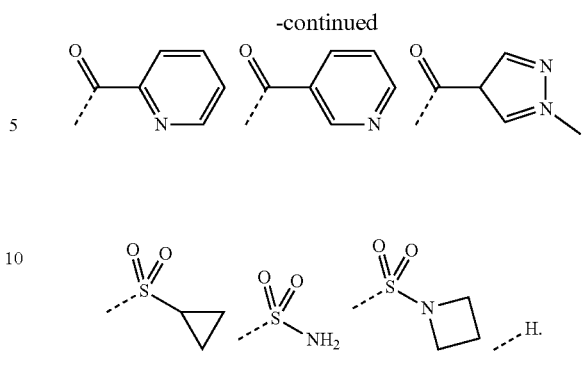
In some embodiments of aspects provided herein, the compound is selected from the group consisting of:
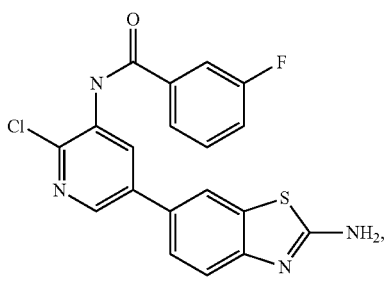
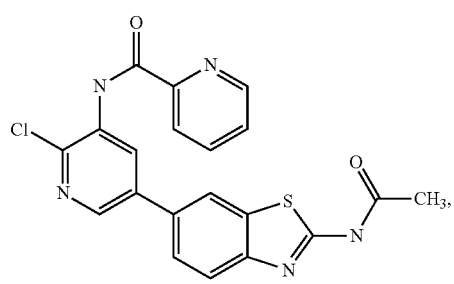
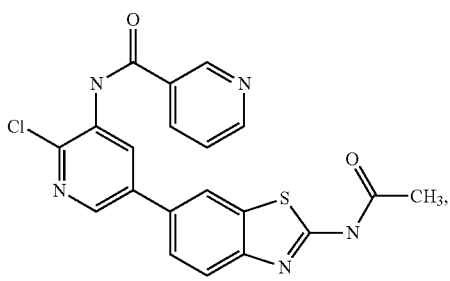
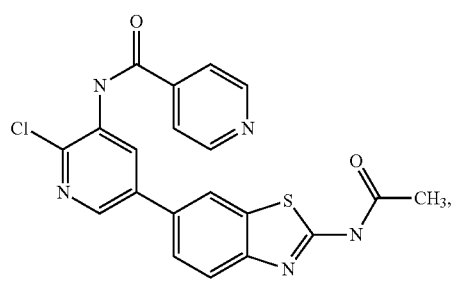
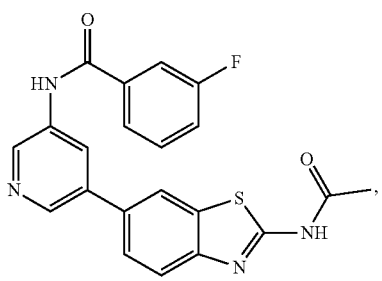
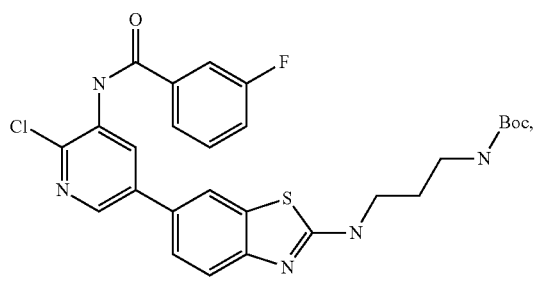
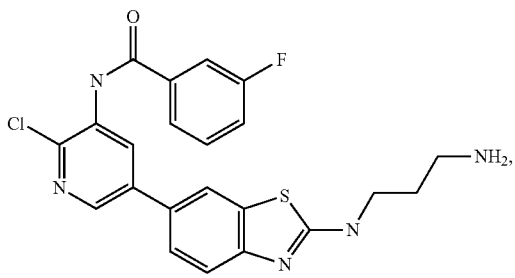

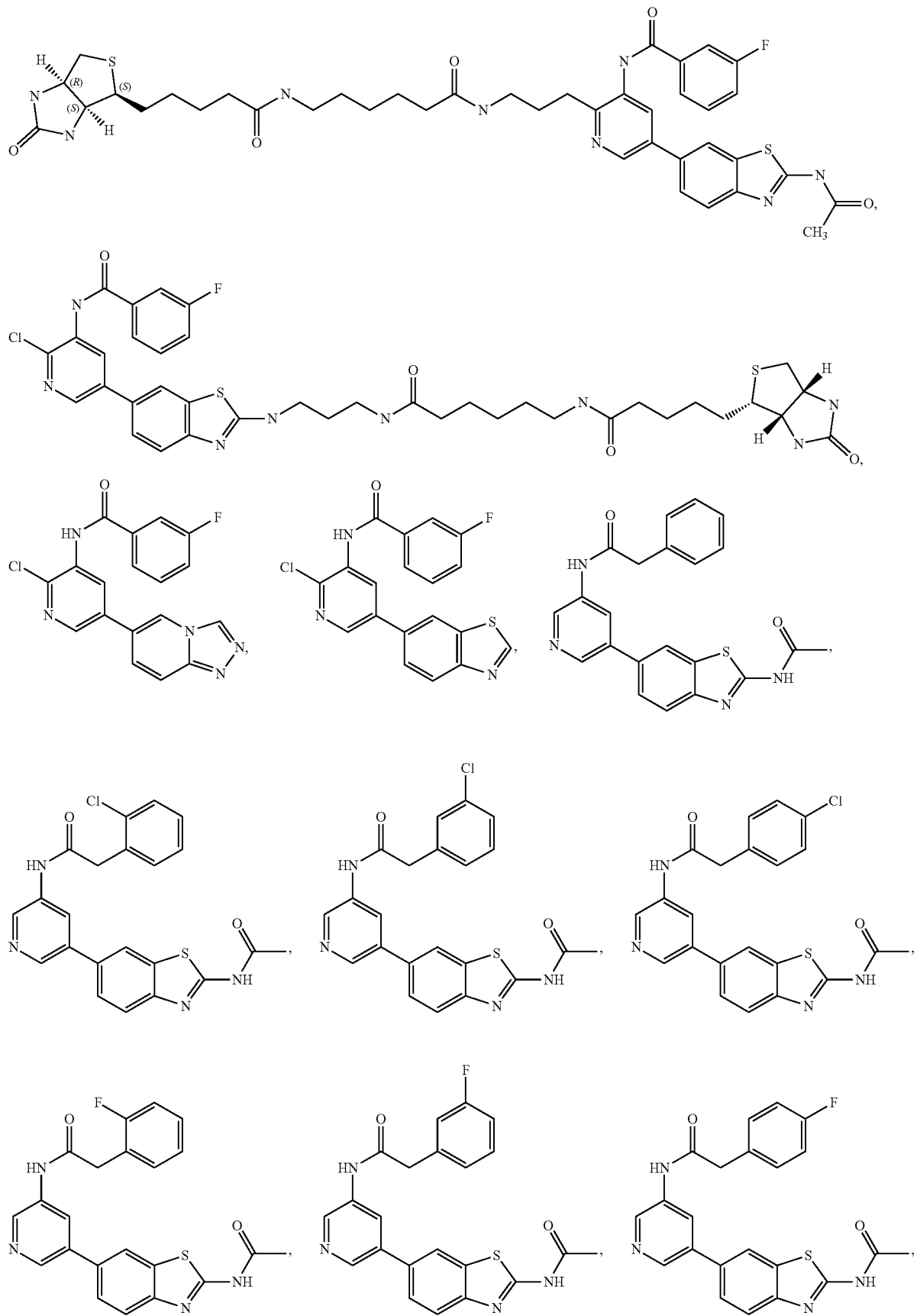

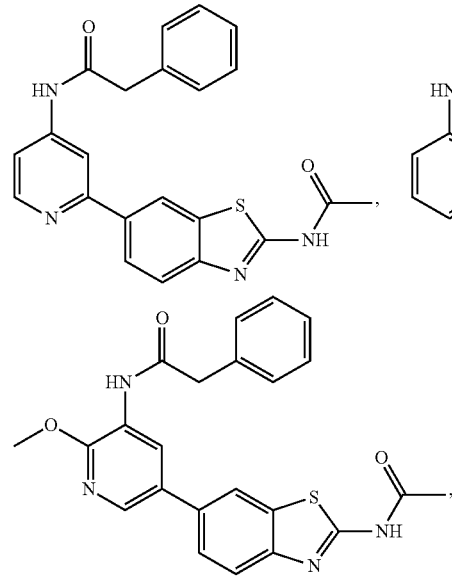
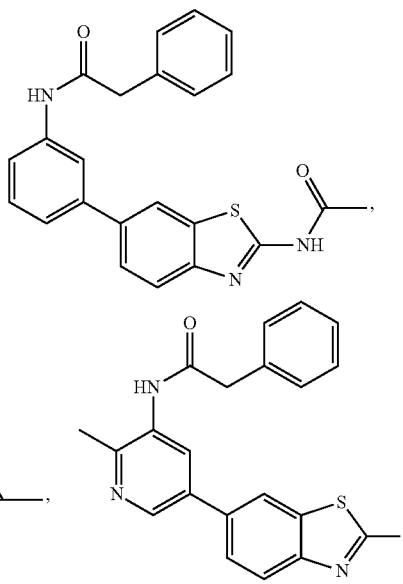
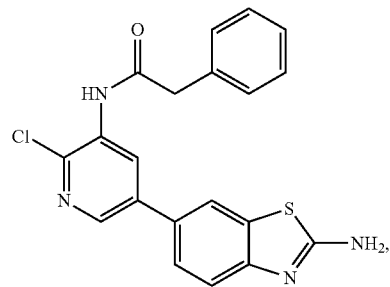
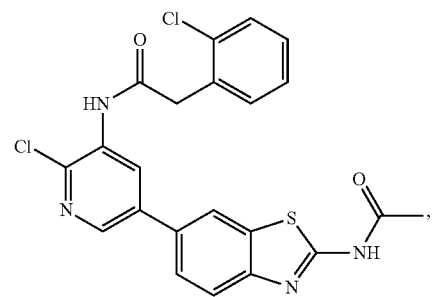
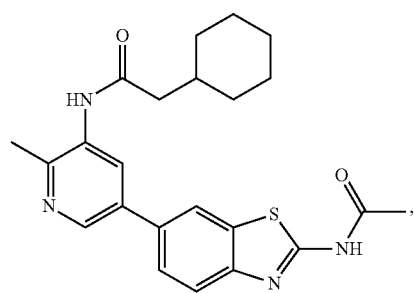
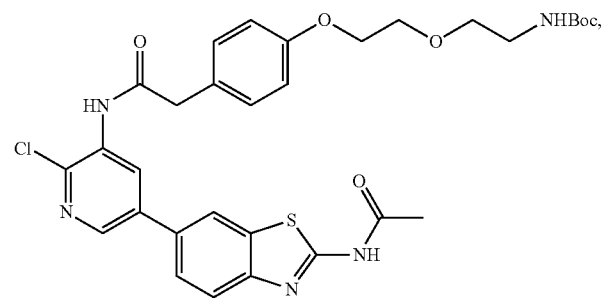
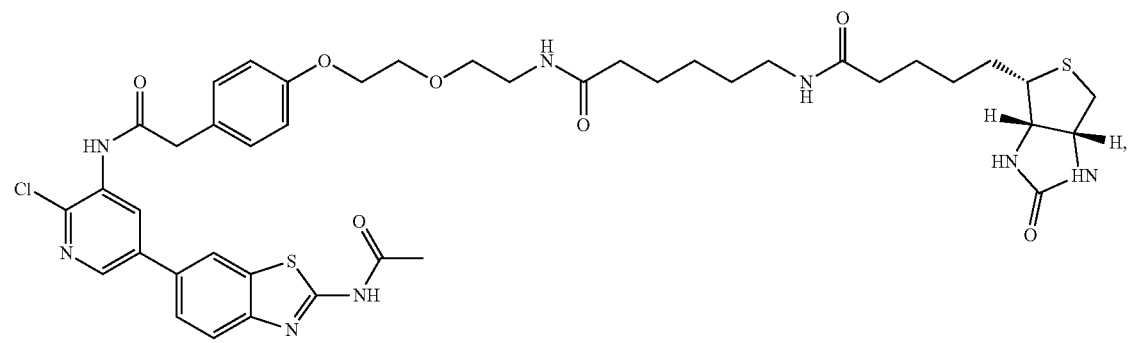

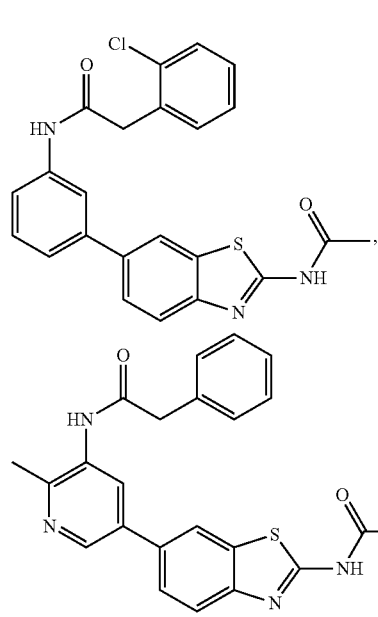
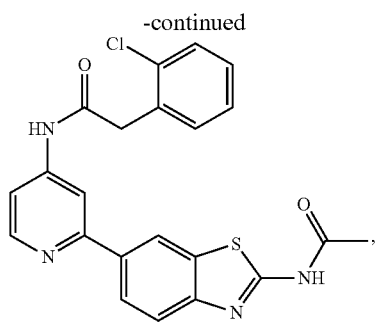
-continued
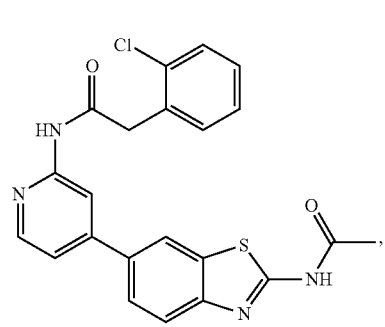
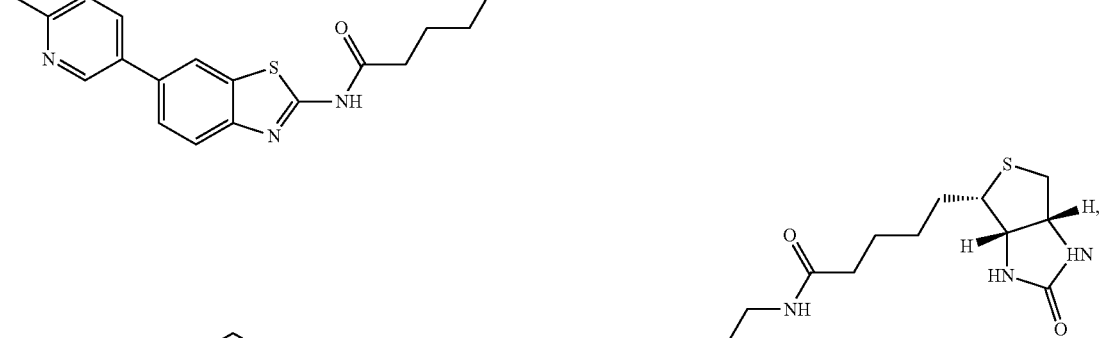
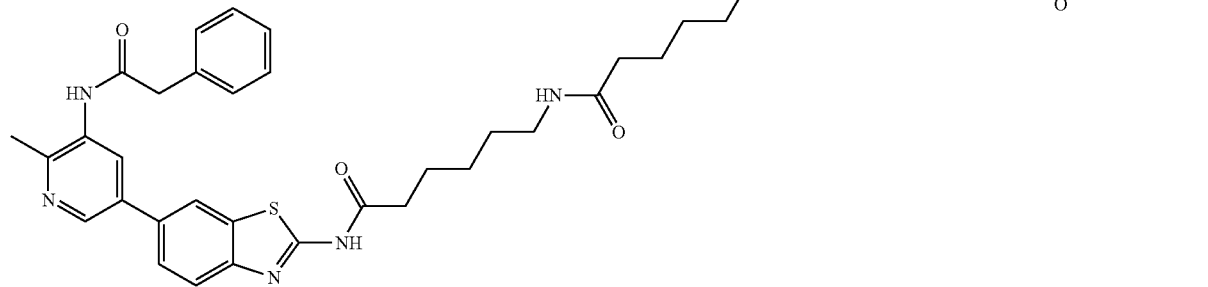
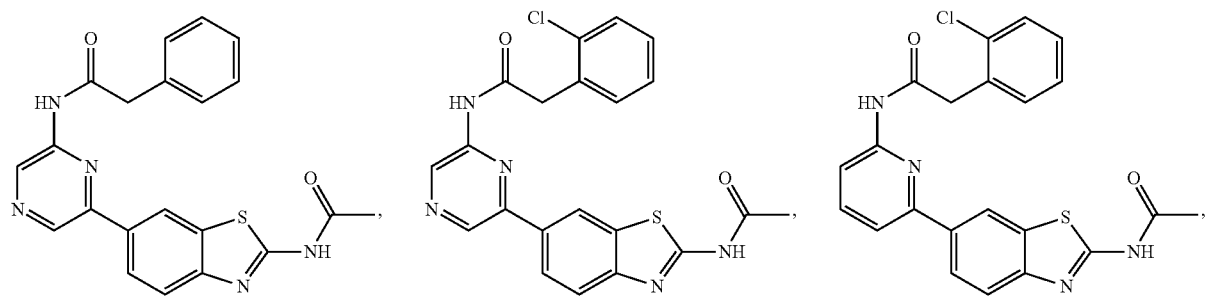
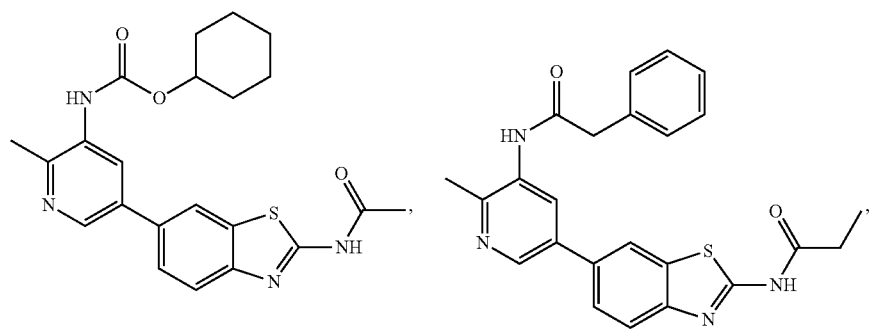

-continued
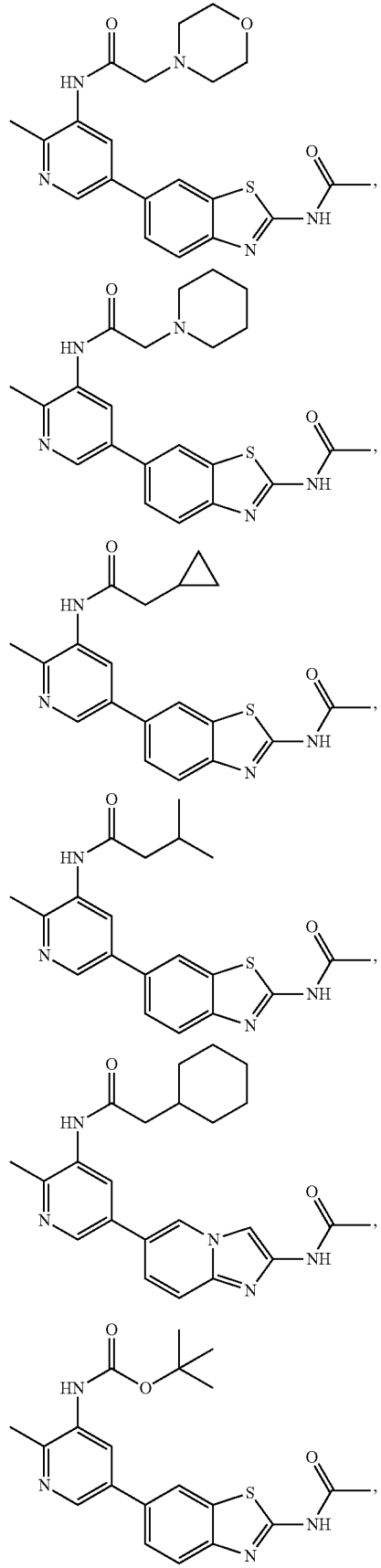
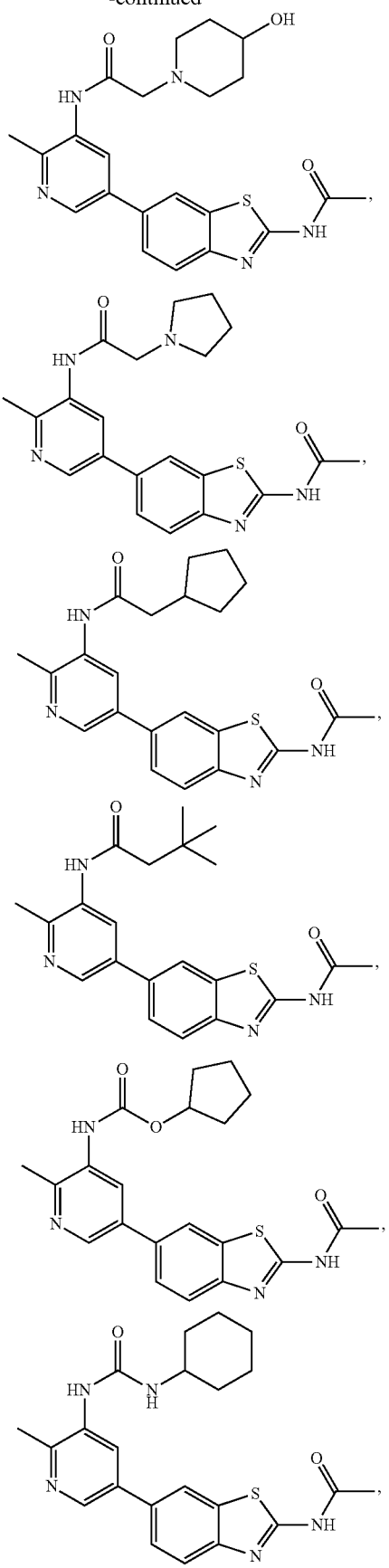

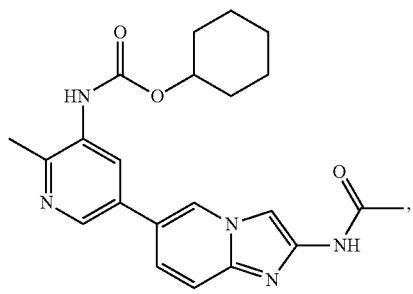
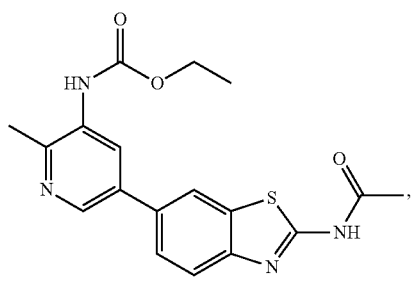
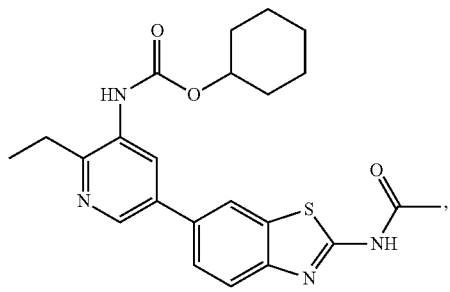
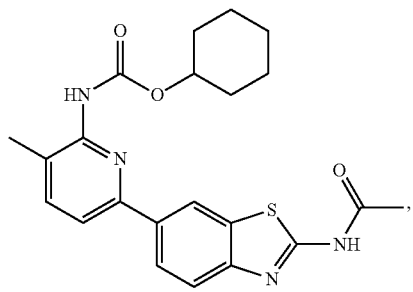
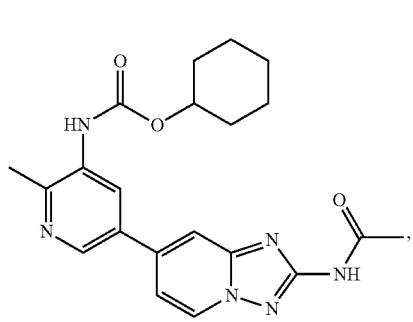
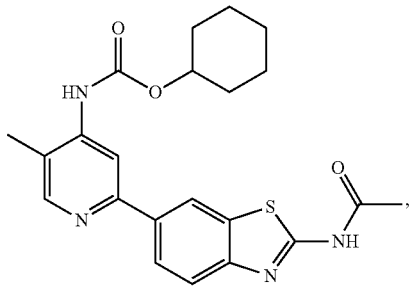
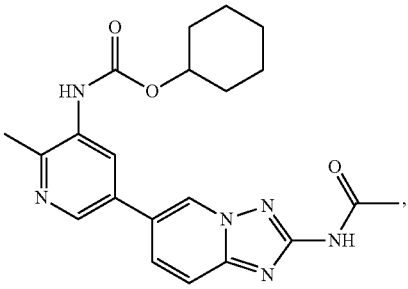
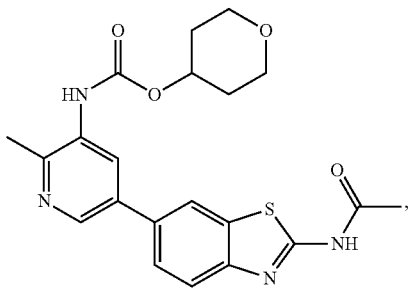
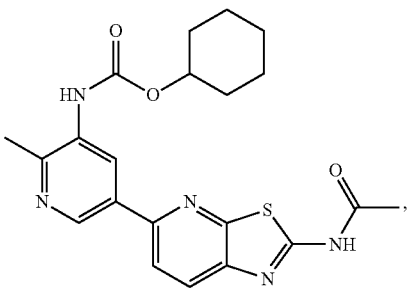
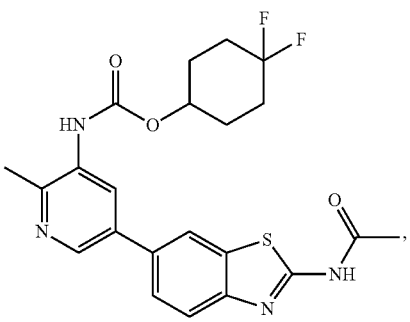

-continued
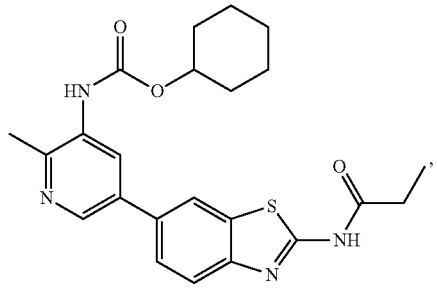
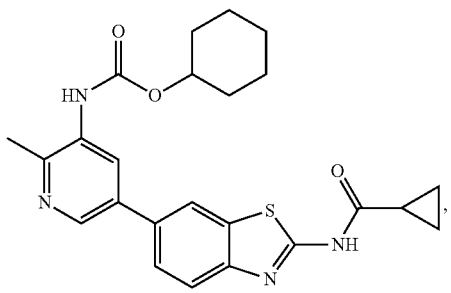
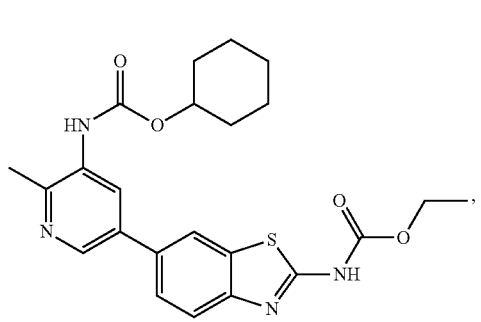
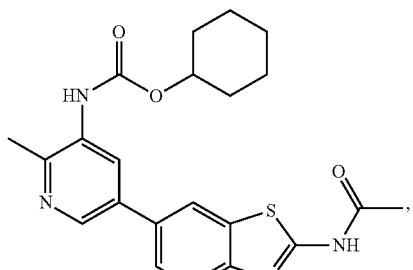
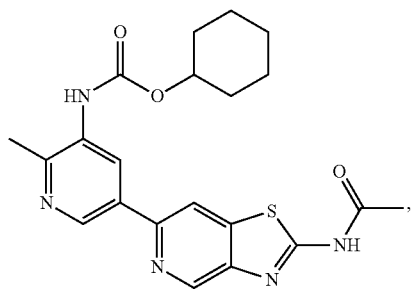
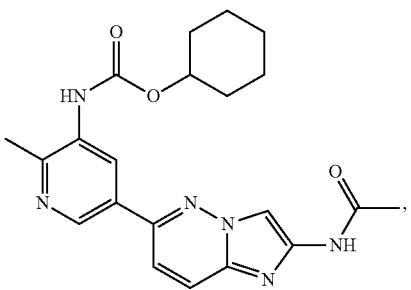
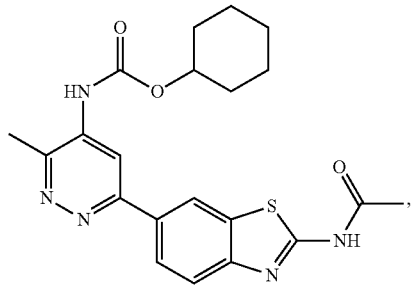
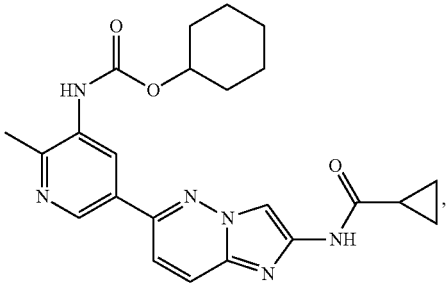
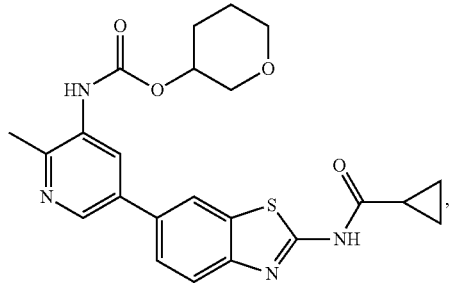
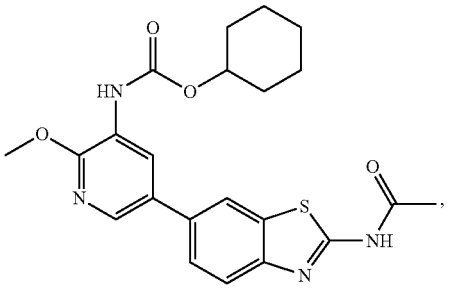

-continued
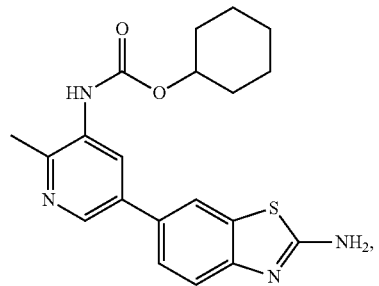 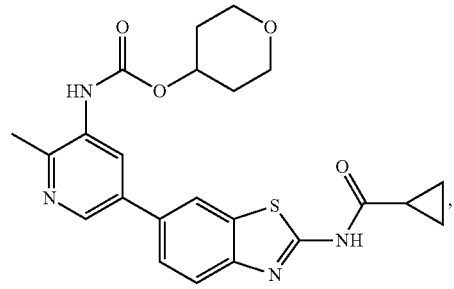
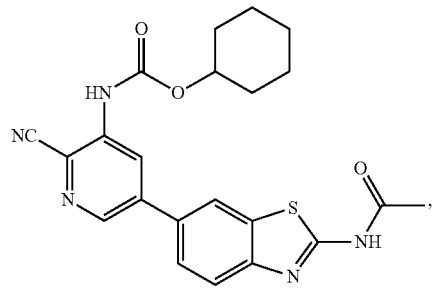 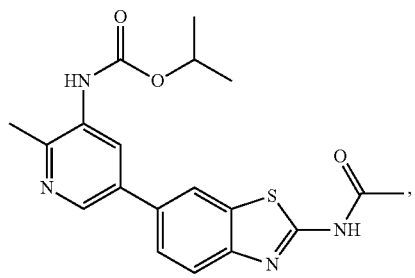
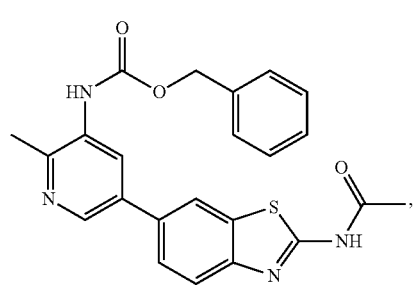 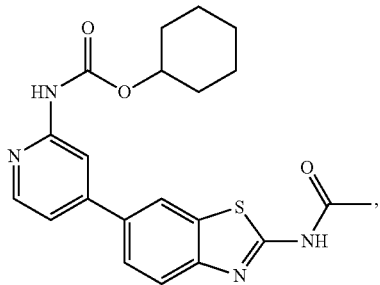
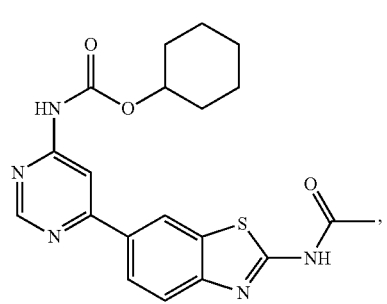 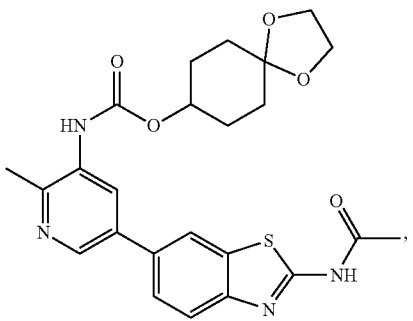
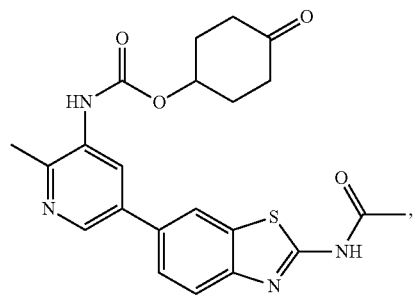 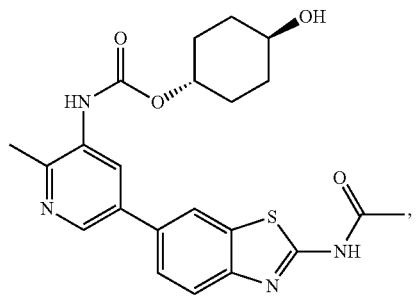

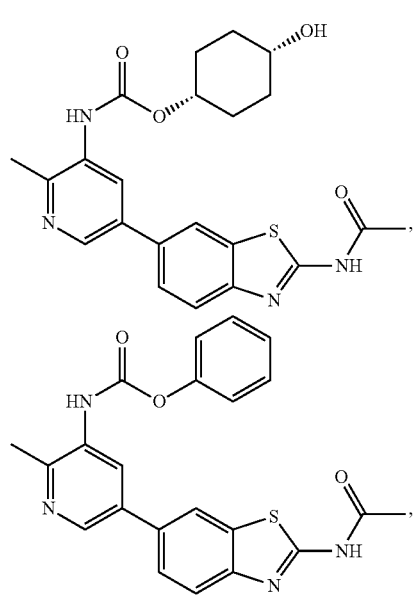
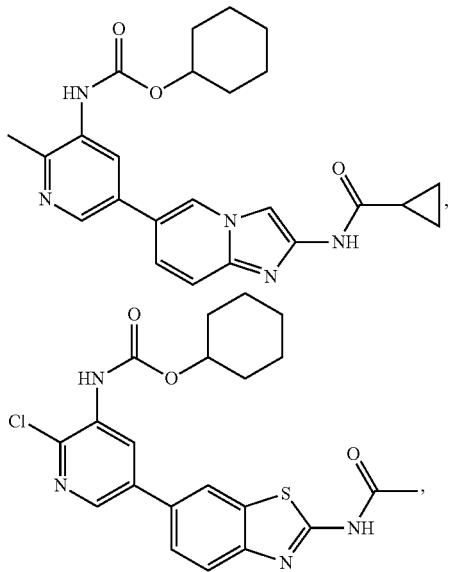
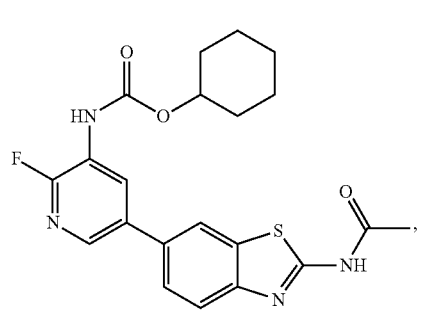
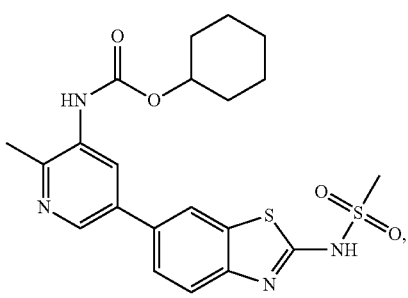
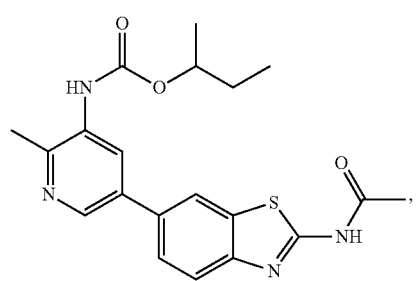
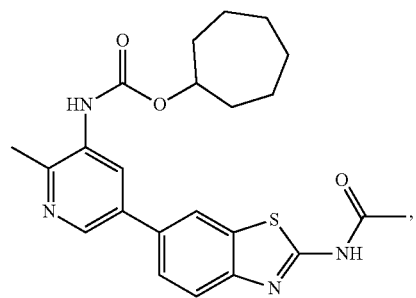
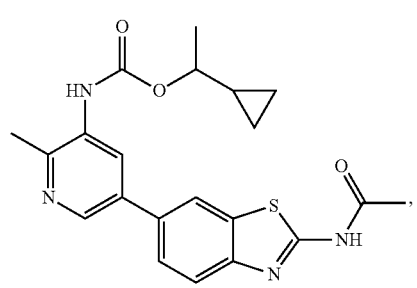
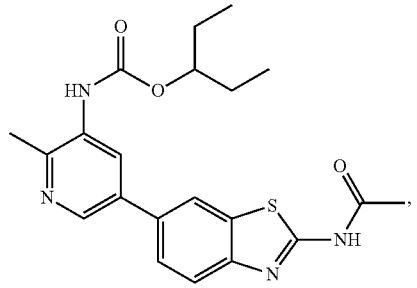

-continued
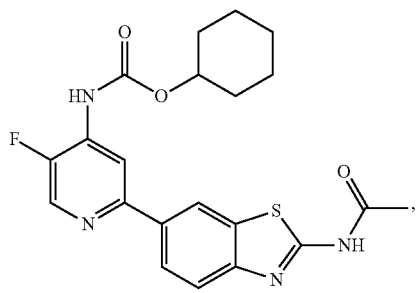
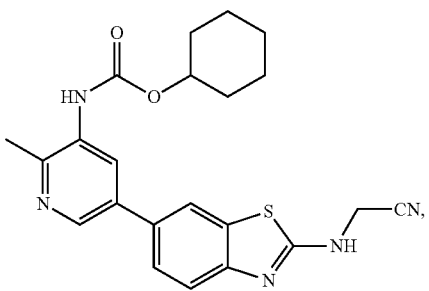
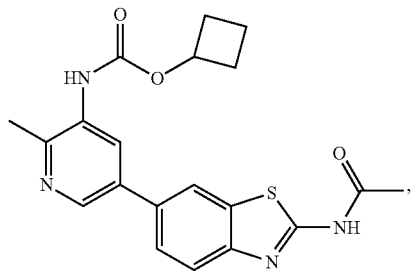
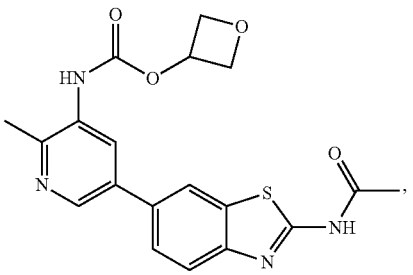
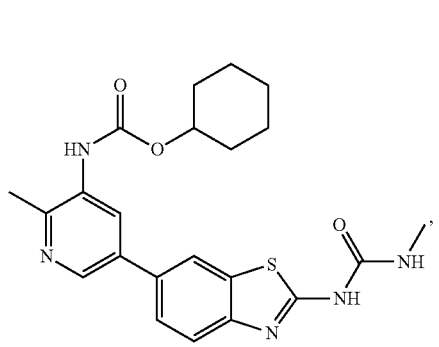
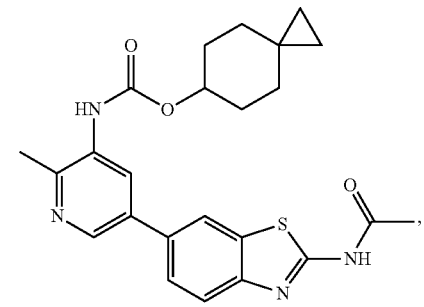
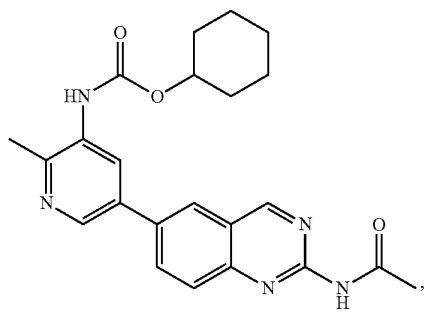
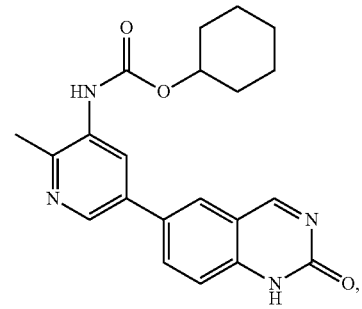
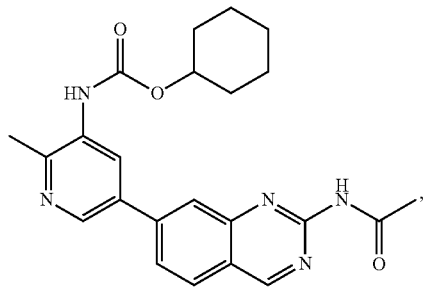
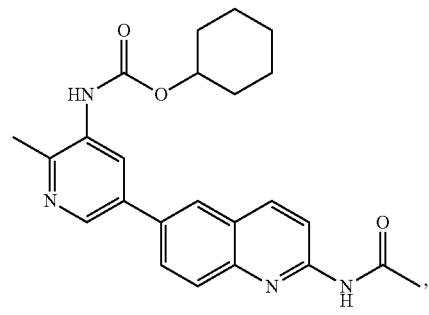

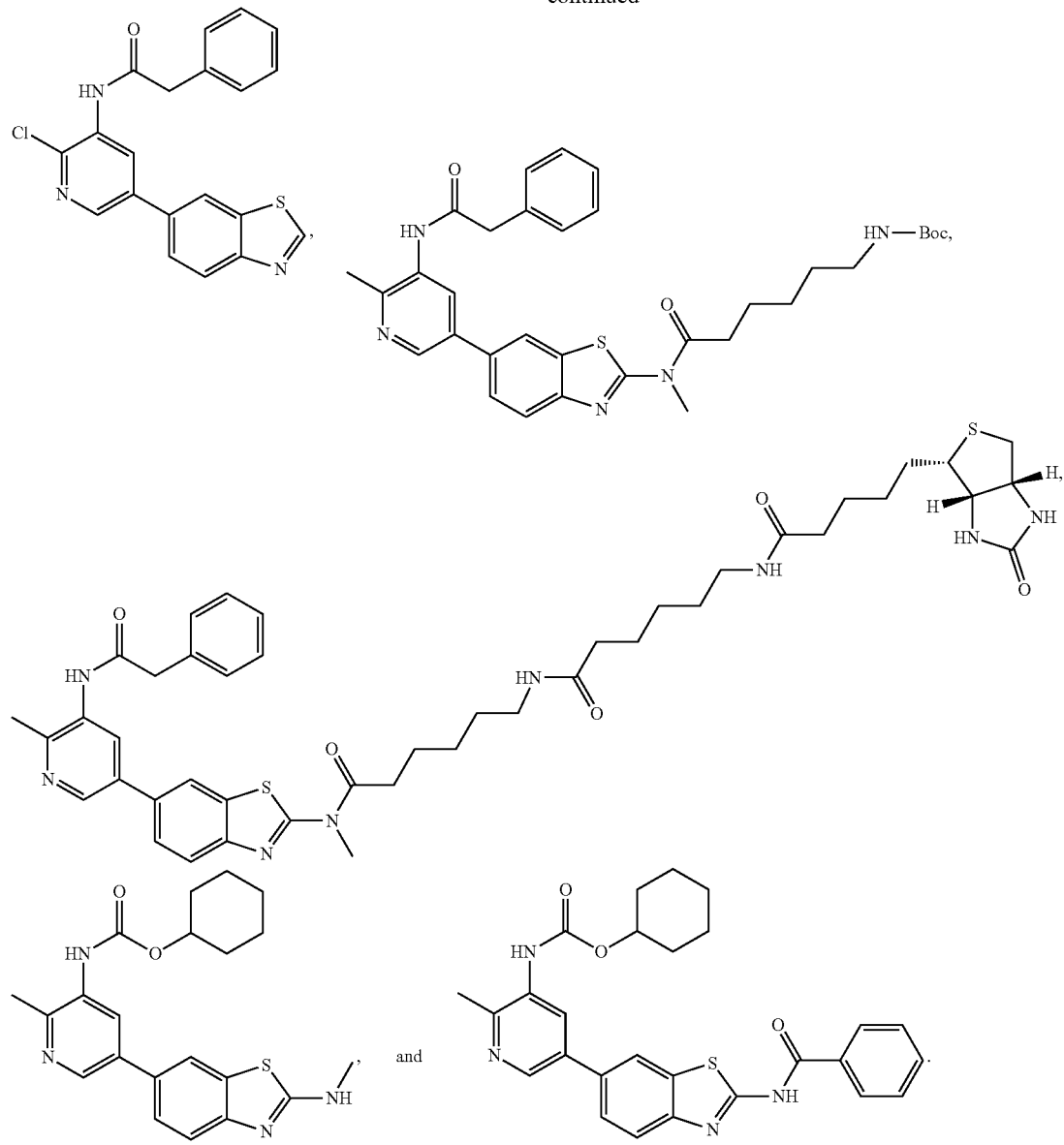
In some embodiments of aspects provided herein, $X_1$, $X_2$ and $X_3$ are CH, $G_1$ and $G_2$ are C, $V_1$ is S, $V_2$ is N, and W is C—$NR_7R_8$ to afford a structure shown in Formula Ib:
In some embodiments of aspects provided herein, $A_1$ is N, $A_2$ and $A_3$ are CH, $G_1$ and $G_2$ are C, $V_1$ is S, $V_2$ is N, and W is C—$NR_7R_8$ to afford a structure shown in Formula Ic:
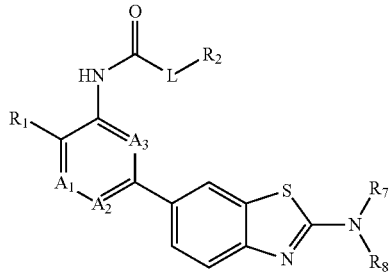
Ib
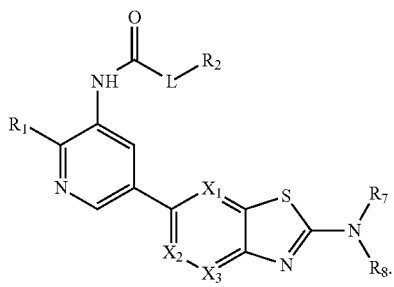
Ic Another aspect of the present disclosure provides a pharmaceutical composition comprising a therapeutically effective amount of a compound as in one of claims 1-10 inclusive and a pharmaceutically acceptable carrier or diluent.

Still another aspect of the present disclosure provides a method for treating a necrosis-related disorder in a mammal suffering therefrom, comprising administering to the mammal a therapeutically effective amount of at least one compound of claim 1, or a pharmaceutical composition thereof, wherein the necrosis-related disorder is systematic inflammatory response, tumor, cancer, metabolic diseases or neurodegenerative diseases.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Figure 1:
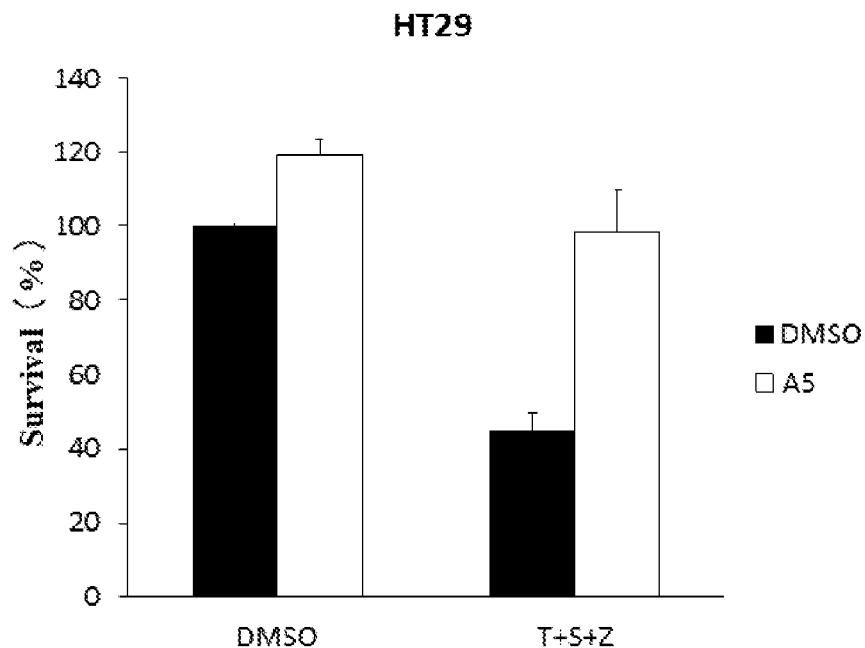
FIG. 1 depicts the inhibition of TNF-α induced-necrosis in HT29 cells by compound A5 in Example 55.

Before proceeding with the detailed description, it is to be appreciated that the following detailed description is merely exemplary in nature and is not intended to limit the invention or the application and uses thereof. Hence, although the present disclosure is, for convenience of explanation, depicted and described as shown in certain illustrative embodiments, it will be appreciated that it can be implemented in various other types of embodiments and equivalents, and in various other systems and environments. Furthermore, there is no intention to be bound by any theory presented in the preceding background or the following detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms.

As used herein, the singular forms "a," "an" and "the" include plural referents unless the context clearly dictates otherwise. Thus, for example, reference to "a molecule" includes a plurality of such molecules, and the like.

The term "about" or "nearly" as used herein generally refers to within +/−15%, 10%, 9%, 8%, 7%, 6%, 5%, 4%, 3%, 2%, or 1% of the designated amount.

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms.

The term "alkyl" as used herein generally refers to a straight or branched chain saturated aliphatic hydrocarbon. Alkyl groups include groups having from 1 to 8 carbon atoms ($C_1$-$C_8$ alkyl), from 1 to 6 carbon atoms ($C_1$-$C_6$ alkyl) and from 1 to 4 carbon atoms ($C_1$-$C_4$ alkyl), including, for example, methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. In some instances, a substituent of an alkyl group is specifically indicated. For example, "cyanoalkyl" refers to an alkyl group substituted with at least one cyano substituent.

The term "alkenyl" as used herein generally refers to straight or branched chain alkene groups, which comprise at least one unsaturated carbon-carbon double bond. Alkenyl groups include $C_2$-$C_8$ alkenyl, $C_2$-$C_6$ alkenyl and $C_2$-$C_4$ alkenyl groups, which have from 2 to 8, 2 to 6 or 2 to 4 carbon atoms, respectively, including, for example, ethenyl, allyl or isopropenyl. The term "alkynyl" as used herein generally refers to straight or branched chain alkyne groups, which have one or more unsaturated carbon-carbon bonds, at least one of which is a triple bond. Alkynyl groups include $C_2$-$C_8$ alkynyl, $C_2$-$C_6$ alkynyl and $C_2$-$C_4$ alkynyl groups, which have from 2 to 8, 2 to 6 or 2 to 4 carbon atoms, respectively.

The term "cycloalkyl" as used herein generally refers to a group that comprises one or more saturated rings in which all ring members are carbon, including, for example, cyclopropyl, cyclobutyl, cyclopentyl, cyclohexyl, cycloheptyl, cyclooctyl, adamantyl. Cycloalkyl groups do not comprise an aromatic ring or a heterocyclic ring. For example, certain cycloalkyl groups are $C_3$-$C_7$ cycloalkyl, in which the cycloalkyl group contains a single ring having from 3 to 7 ring members, all of which are carbon. The term "cycloalkenyl" as used herein generally refers to a group that comprises one or more unsaturated rings in which all ring members are carbon.

The term "alkoxy" as used herein generally refers to an alkyl group as described above attached via an oxygen bridge. Alkoxy groups include $C_1$-$C_6$ alkoxy and $C_1$-$C_4$ alkoxy groups, which have from 1 to 6 or from 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups.

The term "alkylamino" as used herein generally refers to a secondary or tertiary amine that has the general structure —NH—R1 or —N(R1)(R2), wherein R1 and R2 are selected independently from alkyl, cycloalkyl and (cycloalkyl)alkyl groups. Such groups include, but are not limited to, for example, mono- and di-($C_1$-$C_6$ alkyl)amino groups, in which each $C_1$-$C_6$ alkyl may be the same or different. It will be apparent that the definition of "alkyl" as used in the term "alkylamino" differs from the definition of "alkyl" used for all other alkyl-containing groups, in the inclusion of cycloalkyl and (cycloalkyl)alkyl groups.

The term "halogen" as used herein generally refers to fluorine, chlorine, bromine, and iodine. The term "haloalkyl" as used herein generally refers to an alkyl group that is substituted with one or more independently chosen halogens (e.g., "$C_1$-$C_6$ haloalkyl" groups have from 1 to 6 carbon atoms and at least one halogen). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl.

The term "heteroaryl" as used herein generally refers to an aromatic group in which at least one aromatic ring comprises at least one heteroatom selected from N, O and S. Heteroaryls include, for example, 5-12 membered heteroaryls. Examples included but are not limited to imidazole, furan, furazan, isothiazole, isoxazole, oxadiazole, oxazole, pyrazine, pyrazole, pyridazine, pyridine, pyrimidine, tetrazole, thiazole and thiophene.

The term "heterocyclic" as used herein generally refers to a ring structure containing 3-12 ring atoms, in which at least one ring atom is carbon and at least one ring atom is heteroatom selected from N, O, and S. A heterocyclic group may be aromatic or non-aromatic. Piperidine and oxetane are non-limiting examples of non-aromatic heterocycles. Thiazole and pyridine are non-limiting examples of aromatic heterocycles.

The terms "substituent" and "substituted," as used herein, generally denote that a molecular moiety is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. A straight chain substitutent may be a moiety such as a halogen, alkyl group, haloalkyl group or other group that is covalently bonded to an atom (preferably a carbon or nitrogen atom) that is a member of a straight chain.

The term "bicycloheteroalkyl" as used herein generally refers to a double ring structure which shares one or two atoms and which comprise at least one hetero atom independently selected from the group consisting of N, O, and S in the ring. The term "bicycloheteroalkylene" as used herein generally refers to a di-radical of bicycloheteroalkyl group, which may bind to two other groups.

The term "cycloalkylamine" as used herein generally refers to either a ring structure with an amino group attached to a carbon atom in the ring or a ring structure with a nitrogen atom as member of the ring.

The term "cycloalkylamide" as used herein generally refers to either a ring structure with an amid group attached to a carbon atom in the ring via the amide carbon or a ring structure with both the amide nitrogen and amide carbon atoms becoming members of the ring.

The term "cyclourea" as used herein generally refers to a ring structure with the urea carbon and both urea nitrogen atoms becoming members of the ring. One example of cyclourea is oxoimidazolidine.

The term "pharmaceutically acceptable" as used herein generally refers to a form of the compound that is safe for administration to a subject. For example, a free base, a salt form, a solvate, a hydrate, a prodrug or derivative form of a compound of formula I, which has been approved for mammalian use, via oral ingestion or any other route of administration, by a governing authority or regulatory agency, such as the Food and Drug Administration (FDA) of the United States, is pharmaceutically acceptable.

Included in the compounds of Formulas I, Ia and Ib are the pharmaceutically acceptable salt forms of the free-base compounds. The term "pharmaceutically-acceptable salts" as used herein generally refers to salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

In some embodiments, the compound(s) of Formulas I, Ia and Ib is used to treat a subject by administering the compound(s) as a pharmaceutical composition. To this end, the compound(s), in one embodiment, is combined with one or more pharmaceutically acceptable excipients, including carriers, diluents or adjuvants, to form a suitable composition, which is described in more detail herein.

The term "excipient" as used herein generally refers to any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein generally refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" as used herein generally refers to quantifying the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Regardless of the route of administration selected, the compounds of the present invention, which may be used in a suitable hydrated form, and/or the pharmaceutical compositions of the present invention, are formulated into pharmaceutically acceptable dosage forms or by other conventional methods known to those of skill in the art.

Actual dosage levels of the active ingredients in the pharmaceutical compositions of the present invention may be varied so as to obtain an effective amount of the active ingredient to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular hedgehog inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. The mode of administration can have a large effect on dosage. Higher doses may be used for localized routes of delivery.

If desired, the effective daily dose of the active compound may be administered as two, three, four, five, six or more sub-doses administered separately at appropriate intervals throughout the day, optionally, in unit dosage forms. Those of skill in the art will readily appreciate that dose levels can vary as a function of the specific compound, the severity of the symptoms and the susceptibility of the subject to side effects. Dosages for a given compound disclosed herein are readily determinable by those of skill in the art by a variety of means.

Pharmaceutical Compositions/Formulations

One embodiment provides a pharmaceutical composition comprising a compound of formula I, or a stereoisomer, tautomer, hydrate, solvate or pharmaceutically acceptable salt thereof, and at least one pharmaceutically acceptable excipient.

In some embodiments, the present invention provides methods for regulating the Wnt signaling pathway and/or treating a Wnt-mediated disorder in a mammal suffering therefrom. The method comprises administrating to a mammalian subject a therapeutically effective amount of at least one compound of formula I, or a pharmaceutical composition thereof, and optionally in combination with a second therapeutic agent. The method comprises treating or preventing disorder is a cell proliferative disorder selected from the group consisting of systemic sclerosis, skin fibrosis, idiopathic pulmonary fibrosis, renal fibrosis, liver fibrosis, drug-induced fibrosis, radiation-induced fibrosis, colorectal cancer, breast cancer, head and neck squamous cell carcinoma, esophageal squamous cell carcinoma, non-small cell lung cancer, gastric cancer, pancreatic cancer, leukemia, lymphoma, neuroblastoma, retinoblastoma, sarcoma, osteosarcoma, chondosarcoma, Ewing's sarcoma, rhabdomyosarcoma, brain tumor, Wilm's tumor, basal cell carcinoma, melanoma, head and neck cancer, cervical cancer and prostate cancer.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in *Remington: The Science and Practice of Pharmacy*, Nineteenth Ed., Easton, Pa.: Mack Publishing Company (1995); Hoover, John E., *Remington's Pharmaceutical Sciences*, Mack Publishing Co., Easton, Pa. (1975); Liberman, H. A. and Lachman, L., Eds., *Pharmaceutical Dosage Forms*, Marcel Decker, New York, N.Y. (1980); and *Pharmaceutical Dosage Forms and Drug Delivery Systems*, Seventh Ed., Lippincott Williams & Wilkins (1999), herein incorporated by reference for such disclosure.

A pharmaceutical composition, as used herein, refers to a mixture of a compound of formula I with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

All formulations for oral administration are in dosages suitable for such administration. Examples of such dosage units are tablets or capsules. In some embodiments, these contain an amount of active ingredient from about 1 to 2000 mg, advantageously from about 1 to 500 mg, and typically from about 5 to 150 mg. A suitable daily dose for a human or other mammal vary widely depending on the condition of the patient and other factors, but, once again, can be determined using routine methods and practices.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Synthetic Methods

Methods of the present invention may include the use of at least one compound of Formulas I, Ia and Ib, which inhibits necrosis in the regulation of repair and/or functional performance of a wide range of cells, tissues and organs, and have therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Accordingly, the methods and compositions of the present invention include the use of the subject inhibitors for all such uses as inhibitors of necrosis may be implicated. Moreover, the subject methods can be performed on cells which are provided in culture (in vitro), or on cells in a whole animal (in vivo).

The examples and preparations provided below illustrated and exemplify the compounds described herein and methods of preparing such compounds. In general, the compounds described herein may be prepared by processes known in the general chemical arts.

The compounds of the present invention can be prepared using various synthetic routes, including those described below, starting from commercially available materials. Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Functional groups may be removed according to known procedures in the art.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981).

All synthetic procedures described herein can be carried out under known reaction conditions, advantageously under those described herein, either in the absence or in the presence (usually) of solvents or diluents.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described above.

All reagents and solvents were obtained commercially. When required, all reagents and solvents were purified by standard techniques: tetrahydrofuran was purified by distillation from sodium. All thin-layer chromatography (TLC, GF254) analyses and column purification (100-200 mesh) were performed on silica gel (Qingdao Haiyang Chemical Co. Ltd. or Yantai Chemical Co. Ltd.), using petroleum ether (b.p. 60-90° C.)/ethyl acetate (v/v) as eluent; and spots revealed by UV visualization at 254 nm and $I_2$ vapor or phosphomolybdic acid. All nuclear magnetic resonance spectra were recorded using a Bruck-400 spectrometer at 400 MHz using TMS as an internal standard. LC-MS was run using an Agilent 1100 system with LC-MSDTrap recorder, diode array detector (DAD) with detecting wavelength at 214 nm and 254 nm, and ESI source. The HPCL column is an Agela Durashell C18 3.5 μm 4.6×50 mm column. Gradients were run using 0.1 $NH_4HCO_3$ aqueous solution and acetonitrile with gradient 5/95 to 95/5 in the run time indicated (for example, 5 min), flow rate at 1.8 mL/min.

The size and scale of the synthetic methods will vary depending on the desired amount of end product. It is understood that while specific reactants and amounts are provided in the Examples, one of skill in the art knows other alternative and equally feasible sets of reactants that will also yield the same compounds. Thus, where general oxidizers, reducers, solvents of various nature (aprotic, apolar, polar, etc.) are utilized, equivalents will be known in the art and are herein contemplated for use in the present methods.

Many of the steps below indicate various work-ups following termination of the reaction. A work-up involves generally quenching of a reaction to terminate any remaining catalytic activity and starting reagents. This is generally followed by addition of an organic solvent and separation of the aqueous layer from the organic layer. The product is typically obtained from the organic layer and unused reactants and other spurious side products and unwanted chemicals are generally trapped in the aqueous layer and discarded. The work-up in standard organic synthetic procedures found throughout the literature is generally followed by drying the product by exposure to a drying agent, such as anhydrous $Na_2SO_4$, to remove any excess water or aqueous byproducts remaining partially dissolved in the organic layer and concentration of the remaining organic layer. Concentration of product dissolved in solvent may be achieved by any known means, such as evaporation under pressure, evaporation under increased temperature and pressure, and the like. Such concentrating may be achieved by use of standard laboratory equipment such as rotary-evaporator distillation, and the like. This is optionally followed by one or more purification steps which may include, but is not limited to, flash column chromatography, filtration through various media and/or other preparative methods known in the art and/or crystallization/recrystallization. (See, for instance, Addison Ault, "Techniques and Experiments for Organic Chemistry," 6th Ed., University Science Books, Sausalito, Calif., 1998, Ann B. McGuire, Ed., pp. 45-59).

General Synthetic Routes

The following Methods A-F are embodiments for some general synthetic routes leading to compounds of Formula I, Ia, and b. Detailed reaction conditions for each Method can be found in the examples shown vide infra.

Method A:

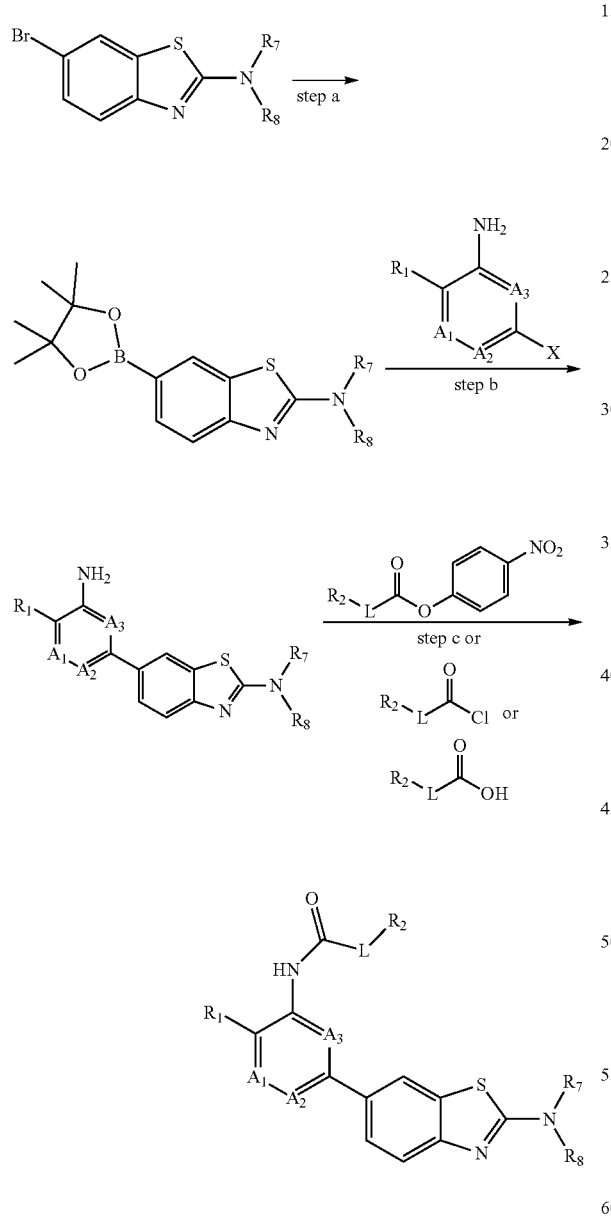

A protected 6-bromobenothiazole can undergo a Miyaura Borylation reaction to give a boronate product (step a). The boronate product can react with a heteroaryl halide in a Suzuki coupling reaction to give a heteroaryl-substituted benothizole compound (step b). Finally, the free amine on the heteroaryl ring can be acylated to give the final product (step c).

Method B:

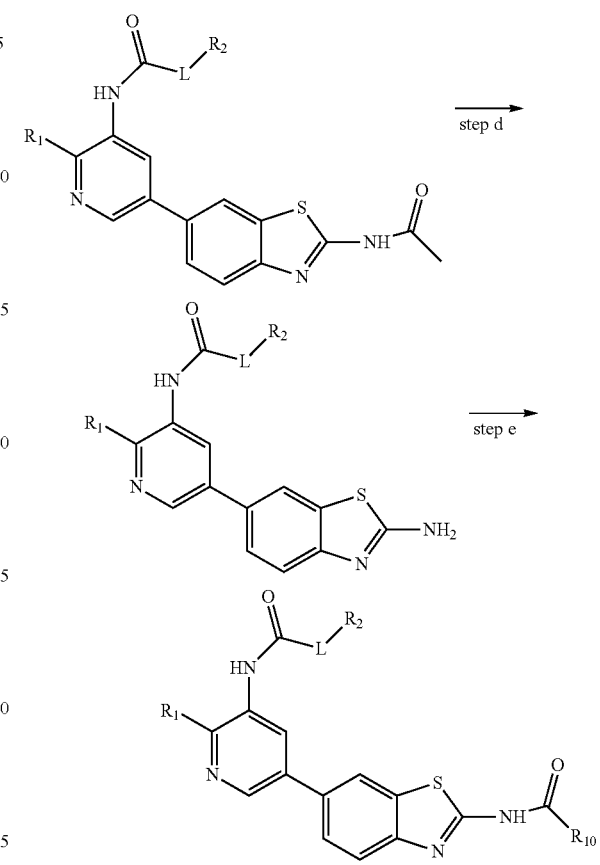

An acetamide product can be hydrolysized to give a substituted benothizole amine (step d). Finally, the free amine on the benothiazole ring can be acylated to give the final product (step e).

Method C:

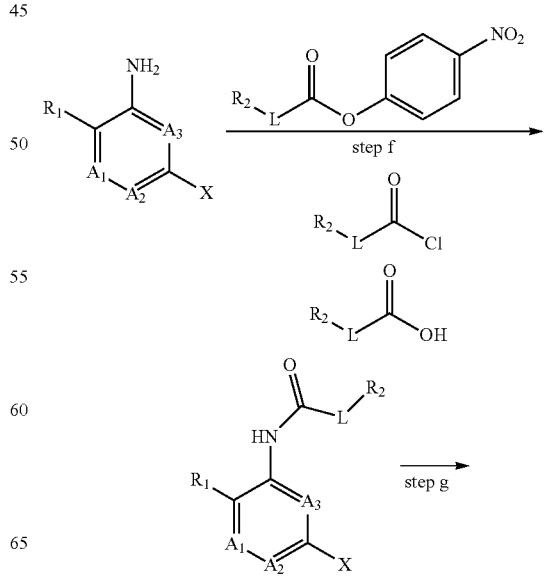

41

-continued

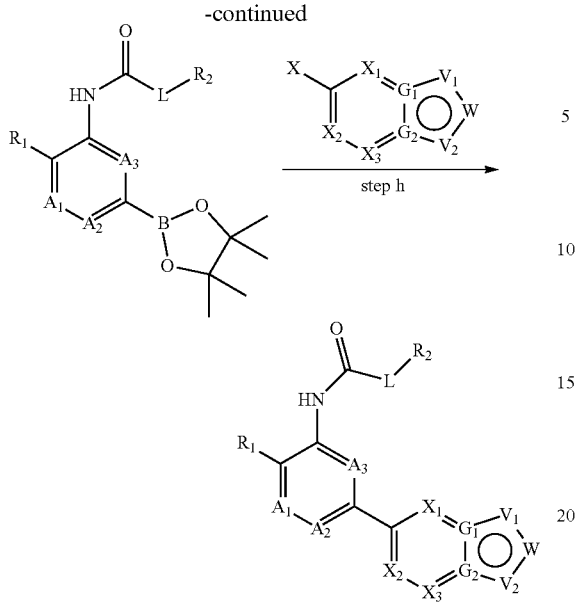

A halide substituted hetetroarylamine can be acylated to give a halide substituted hetetroarylamide (step f). Then the halide substituted hetetroarylamide can undergo a Miyaura Borylation reaction to give a boronate product (step g). The boronate product can react with a heteroaryl halide in a Suzuki coupling reaction to give the final product (h).

Method D:

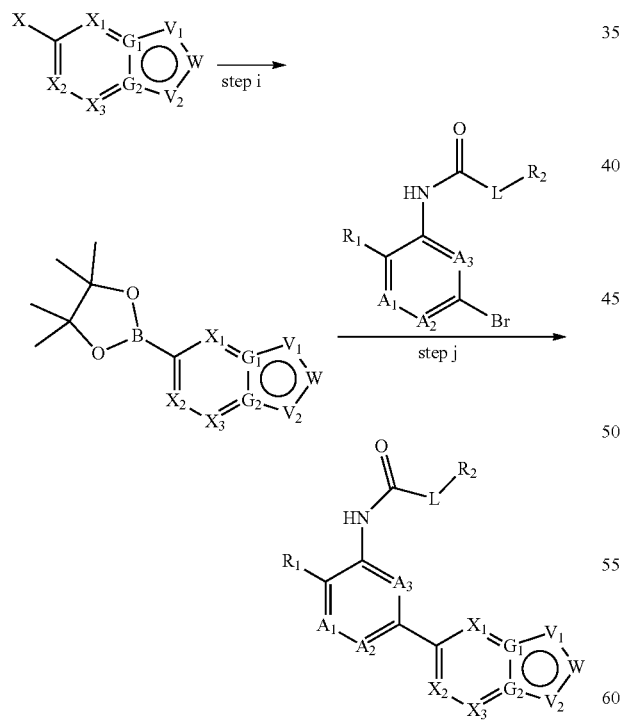

A halide substituted biheteroaryl ring can undergo a Miyaura Borylation reaction to give a boronate product (step i), and then the boronate product can react with a heteroaryl bromide in a Suzuki coupling reaction to give the final product (step j).

42

Method E:

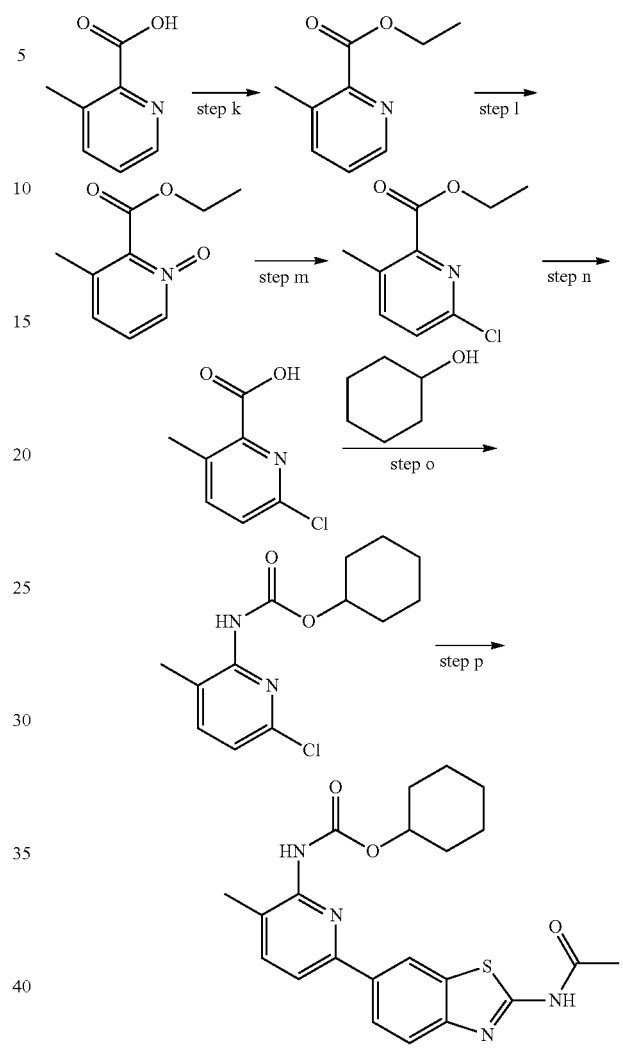

A 3-methylpicolinic acid can be esterified to give ethyl 3-methylpicolinate (step k), then the 2-(ethoxycarbonyl)-3-methylpyridine 1-oxide can be subjected to an m-CPBA oxidation (step l). Then ensuing chlorination of 2-(ethoxycarbonyl)-3-methylpyridine 1-oxide with phosphoryl trichloride can produce ethyl 6-chloro-3-methylpicolinate (step m). The ethyl 6-chloro-3-methylpicolinate can be hydrolysized to give picolinic acid, which can undergo a Curtius rearrangement reaction to afford cyclohexyl 6-chloro-3-methylpyridin-2-ylcarbamate (steps n and o). The chloropyridine intermediate can react with a boronate product in a Suzuki coupling reaction to give the final product (step p).

Method F:

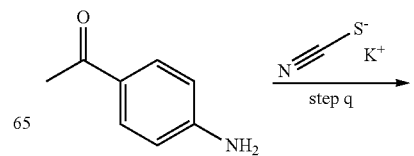

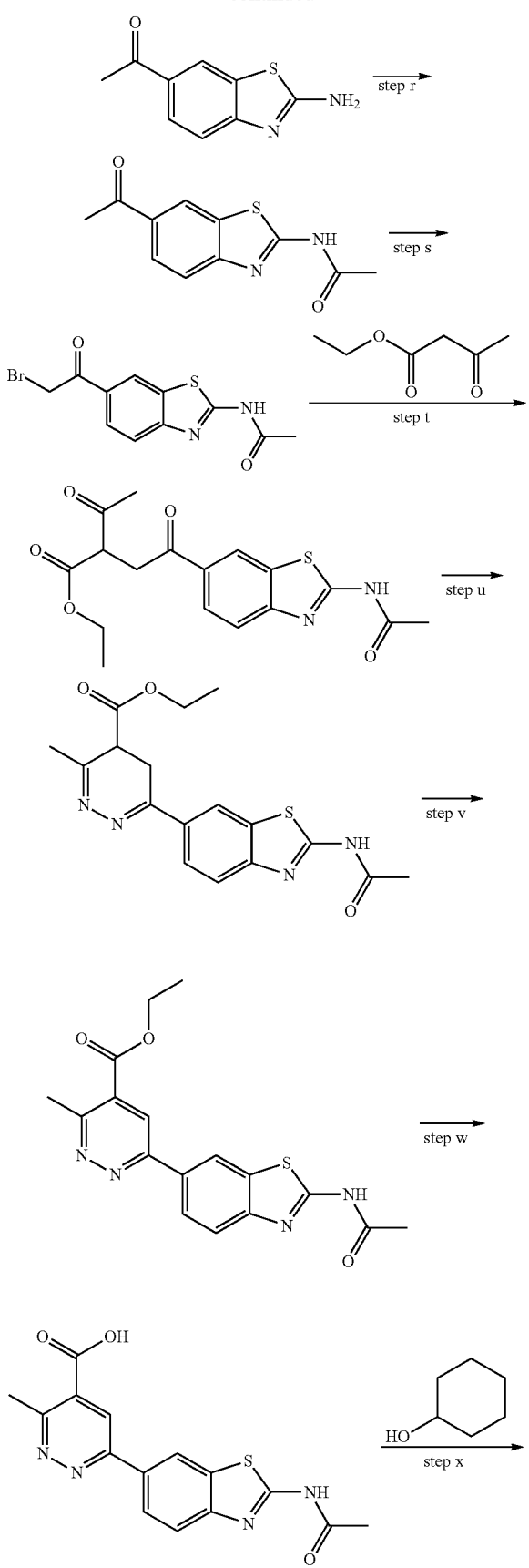

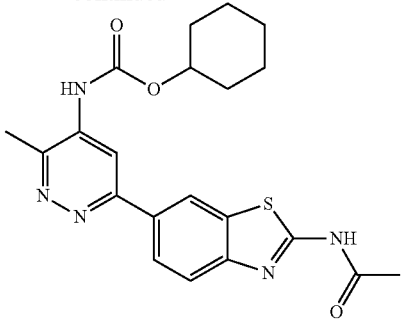 [SMILES: CC(=O)Nc1nc2ccc(-c3cc(NC(=O)OC4CCCCC4)c(C)nn3)cc2s1]

The commercially available reagent 1-(4-aminophenyl)ethanone can react with potassium thiocyanate to give 1-(2-aminobenzo[d]thiazol-6-yl)ethanone (step q). The free amine of benothiazole can be acylated to give the N-(6-acetylbenzo [d]thiazol-2-yl)acetamide (step r). Then bromination of the acetamide with $Br_2$ can produce N-(6-(2-bromoacetyl) benzo[d]thiazol-2-yl)acetamide (step s). The α-bromoketone intermediate can be alkylated with ethylacetoacetate to afford ethyl 4-(2-acetamidobenzo[d]thiazol-6-yl)-2-acetyl-4-oxobutanoate (step t). The protected benzothiazole can cyclize with hydrazine to give ethyl 6-(2-acetamidobenzo[d]thiazol-6-yl)-3-methyl-4,5-dihydropyridazine-4-carboxylate (step u) and then oxidation of dihydropyridazine with bromine can produce a pyridazine compound (step v). The pyridazine compound can be hydrolysized (step w) to afford pyridazine acid, which can undergo a Curtius rearrangement reaction to give the final product (step x).

Example 1: Compound A42 Made by Method A

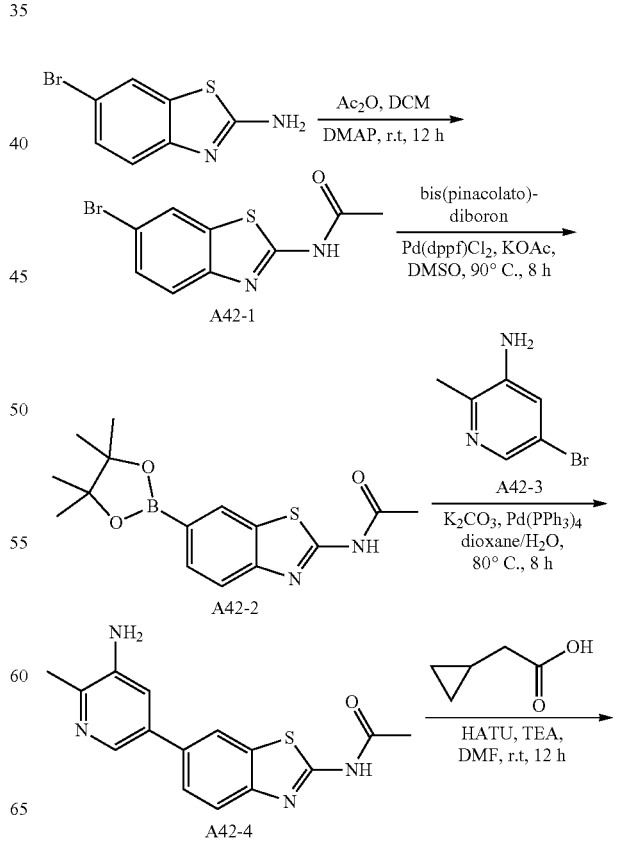

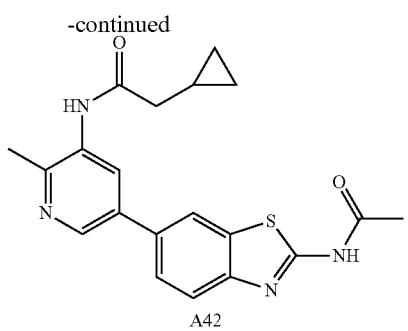

Step 1: N-(6-bromobenzo[d]thiazol-2-yl)acetamide

To a stirred solution of 6-bromobenzo[d]thiazol-2-amine (2.50 g, 10.7 mmol) and DMAP (1.33 g, 12.8 mmol) in 20 mL dichloromethane at 0° C., Ac$_2$O (1.23 mL, 13.0 mmol) was added dropwise. After carried out at r.t. overnight, the mixture was quenched with 100 mL 1 N HCl. The resulting precipitate was filtered. The cake was washed with water and dried under vacuum to give A42-1 as a white solid (2.30 g, 79%). $^1$H NMR (300 MHz, CDCl$_3$) δ 9.90 (br s, 1H), 7.94 (s, 1H), 7.61 (d, J=10.4 Hz, 1H), 7.54 (d, J=10.4 Hz, 1H), 2.30 (s, 3H).

Step 2: N-(6-(4,4,5,5-tetramethyl-1,3,2-dioxaborolan-2-yl)benzo-[d]thiazol-2-yl) Acetamide A 100 mL flask was charged with A42-1 (2.10 g, 7.75 mmol), bis(pinacolato)diboron (3.00 g, 11.8 mmol), KOAc (3.00 g, 30.6 mmol) and Pd(dppf)Cl$_2$ (560 mg, 0.765 mmol) followed by addition of 50 mL DMSO. The equipment was evacuated and refilled with N$_2$ three times. The reaction was carried out at 90° C. for 8 h. After cooled to r.t., the mixture was filtered. The filtrate was diluted with ethyl acetate. The organic phase was washed with brine. The organic phase was dried with Na$_2$SO$_4$ and the solvent was removed by vacuum. The residue was recrystallized in petroleum ether to give A42-2 as a brown solid (2.40 g, 97%). $^1$H NMR (300 MHz, CDCl$_3$) δ 8.30 (s, 1H), 7.87 (d, J=8.0 Hz, 1H), 7.72 (d, J=8.0 Hz, 1H), 2.30 (s, 3H), 1.37 (s, 12H).

Step 3: N-(6-(5-amino-6-methylpyridin-3-yl)benzo[d]thiazol-2-yl)acetamide

A 25 mL flask was charged with A42-2 (318 mg, 1.00 mmol), 5-bromo-2-methylpyridin-3-amine A42-3 (187 mg, 1.00 mmol), K$_2$CO$_3$ (345 mg, 2.50 mmol) and Pd(PPh$_3$)$_4$ (90 mg, 0.078 mmol) followed by addition of dioxane/H$_2$O (10 mL/0.5 mL). The equipment was evacuated and refilled with N$_2$ three times. The reaction was carried out at 80° C. for 8 h. After cooled to r.t., the resulting precipitate was filtered. The cake was washed with ethyl acetate to give A42-4 as a white solid (150 mg, 50%). $^1$H NMR (400 MHz, DMSO-d6) δ 8.13 (s, 1H), 8.00 (s, 1H), 7.73 (d, J=8.4 Hz, 1H), 7.58 (d, J=8.4 Hz, 1H), 7.20 (s, 1H), 5.14 (s, 2H), 2.30 (s, 3H), 2.18 (s, 3H).

Step 4: N-(5-(2-acetamidobenzo[d]thiazol-6-yl)-2-methylpyridin-3-yl)-2-cyclopropylacetamide A mixture of A42-4 (30 mg, 0.10 mmol), 2-cyclopropylacetic acid (12 mg, 0.12 mmol), HATU (57 mg, 0.15 mmol) and TEA (15 mg, 0.15 mmol) in 2 mL DMF was stirred at r.t. overnight. After that, the mixture was diluted with ethyl acetate. The organic phase was washed with brine. The organic phase was dried with Na$_2$SO$_4$ and the solvent was removed by vacuum. The residue was purified by column chromatography (dichloromethane:methanol=100:2) to give A42 as a white solid (17 mg, 45%). $^1$H NMR (400 MHz, DMSO-d6) δ 12.41 (s, 1H), 9.44 (s, 1H), 8.62 (s, 1H), 8.32 (s, 1H), 8.16 (s, 1H), 7.82 (d, J=8.4 Hz, 1H), 7.72 (d, J=8.4 Hz, 1H), 2.46 (s, 3H), 2.31 (d, J=7.0 Hz, 2H), 2.22 (s, 3H), 1.13-1.09 (m, 1H), 0.52-0.51 (m, 2H), 0.25-0.24 (m, 2H).

Example 2: Compound A36 Made by Method D

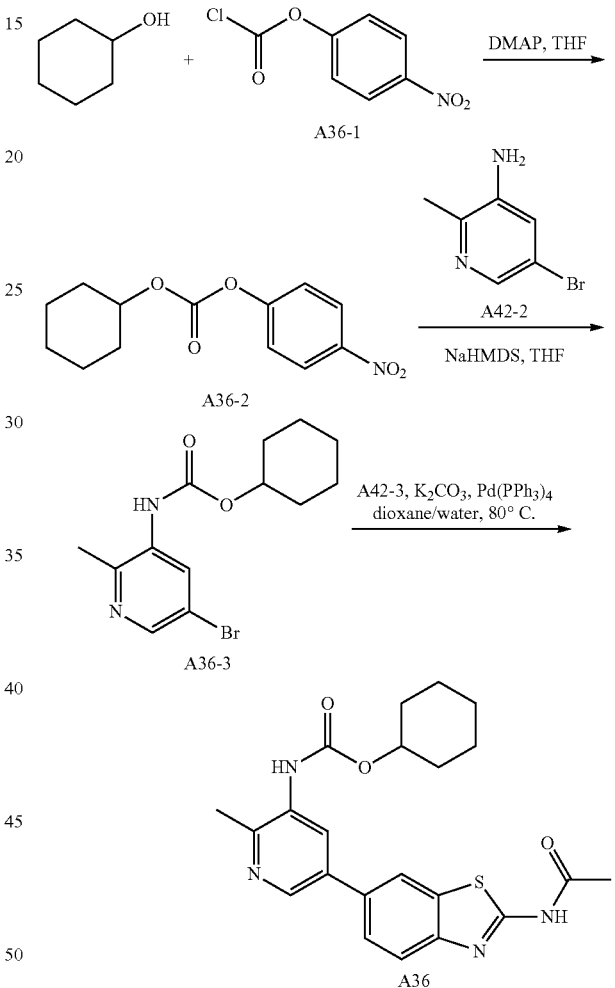

A Step 1: Cyclohexyl (4-nitrophenyl) Carbonate

To a stirred solution of cyclohexanol (12.0 g, 118 mmol) and DMAP (1.2 g, 9.9 mmol) in 50 mL THF at 0° C. was added 4-nitrophenyl carbonochloridate A36-1 (20 g, 99 mmol) in partitions. The reaction was carried out at r.t. for 4 h. After the solvent removed by vacuum, the residue was purified by column chromatography (petroleum ether:ethyl acetate=100:2) to give A36-2 as a white solid (12.4 g, 47%).

Step 2: Cyclohexyl (5-bromo-2-methylpyridin-3-yl)carbamate

To a stirred solution of 5-bromo-2-methyl-pyridin-3-amine (1.4 g, 7.6 mmol) in 20 mL anhydrous THF at 0° C., NaHMDS (2 M, 8 mL, 16 mmol) was added dropwise. After stirred for 15 min, a solution of A36-2 (2.4 g, 9.1 mmol) in 5 mL anhydrous THF was added dropwise. The reaction was carried out at 0° C. for another 15 min. After that, the reaction was quenched with water. The mixture was diluted with ethyl acetate. The organic phase was washed with 1 N NaOH. The organic phase was dried over Na$_2$SO$_4$ and the solvent was removed by vacuum. The residue was purified by column chromatography (petroleum ether:ethyl acetate=7:1) to give A36-3 as a yellow solid (2.3 g, 82%). $^1$H NMR (400 MHz, CDCl$_3$) δ 8.48 (s, 1H), 8.26 (s, 1H), 6.38 (s, 1H), 4.87-4.67 (m, 1H), 2.46 (s, 3H), 2.01-1.95 (m, 2H), 1.80-1.71 (m, 2H), 1.53-1.20 (m, 6H).

Step 3: Cyclohexyl (5-(2-acetamidobenzo[d]thiazol-6-yl)-2-methylpyridin-3-yl)carbamate (A36)

A 50 mL flask was charged with A36-3 (1.9 g, 6.29 mmol), A42-2 (1.96 g, 6.29 mmol), K$_2$CO$_3$ (2.17 g, 15.7 mmol) and Pd(PPh$_3$)$_4$ (580 mg, 0.502 mmol) followed by addition of dioxane/H$_2$O (44 mL/4 mL). The equipment was evacuated and refilled with N$_2$ three times. The reaction was carried out at 80° C. for 12 h. After the solvent was removed by vacuum, the residue was purified by column chromatography (dichloromethane:methanol=100:2) to give A36 as a white solid (750 mg, 28%). $^1$H NMR (400 MHz, DMSO-d6) δ 12.41 (s, 1H), 9.12 (s, 1H), 8.59 (s, 1H), 8.31 (s, 1H), 8.10 (s, 1H), 7.82 (d, J=8.4 Hz, 1H), 7.72 (d, J=8.4 Hz, 1H), 4.74-4.56 (m, 1H), 2.46 (s, 3H), 2.22 (s, 3H), 1.92-1.89 (m, 2H), 1.75-1.67 (m, 2H), 1.56-1.25 (m, 6H).

Example 3: Compound A37 Made by Method B

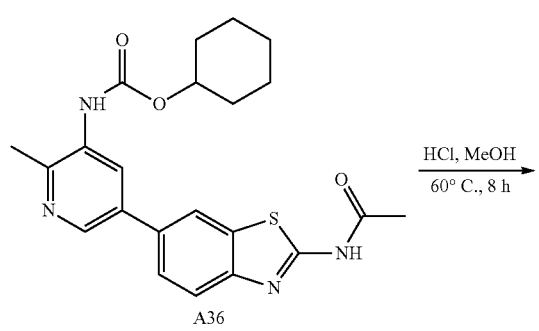

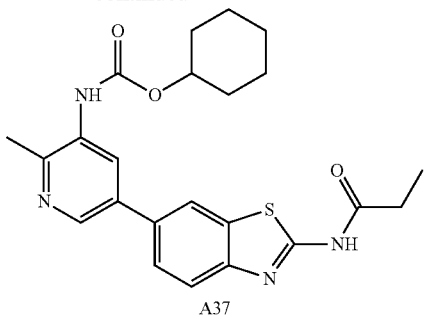

Step 1: Cyclohexyl (5-(2-aminobenzo[d]thiazol-6-yl)-2-methylpyridin-3-yl)carbamate (A70)

A mixture of A36 (300 mg, 0.71 mmol) and one drop of con. HCl in MeOH was heated to 60° C. overnight. After cooled to r.t., the mixture was basified by sat. aq. NaHCO$_3$. The aqueous phase was extracted with ethyl acetate. The combined organic phases were dried over Na$_2$SO$_4$ and the solvent was removed by vacuum to give a white solid (220 mg, 81%). $^1$H NMR (400 MHz, DMSO-d6) δ 9.09 (s, 1H), 8.52 (s, 1H), 8.02 (s, 1H), 8.00 (s, 1H), 7.60 (s, 2H), 7.51 (d, J=8.4 Hz, 1H), 7.40 (d, J=8.4 Hz, 1H), 4.74-4.51 (m, 1H), 2.43 (s, 3H), 1.95-1.87 (m, 2H), 1.78-1.65 (m, 2H), 1.58-1.21 (m, 6H).

Step 2: Cyclohexyl (2-methyl-5-(2-propionamido-benzo[d]thiazol-6-yl)pyridin-3-yl)carbamate (A37)

A mixture of A70 (30 mg, 0.08 mmol), propionic acid (12 mg, 0.16 mmol), HATU (63 mg, 0.16 mmol) and TEA (17 mg, 0.16 mmol) in 1 mL DMF was stirred at r.t. overnight. After that, the mixture was diluted with ethyl acetate. The organic phase was washed with brine. The organic layer was dried with Na$_2$SO$_4$ and the solvent was removed by vacuum. The residue was purified by column chromatography (dichloromethane:methanol=100:2) to give white solid (5 mg, 14%). $^1$H NMR (400 MHz, DMSO-d6) δ 12.37 (s, 1H), 9.80 (s, 1H), 8.63 (s, 1H), 8.31 (s, 1H), 8.15 (s, 1H), 7.80 (d, J=8.0 Hz, 1H), 7.71 (d, J=8.4 Hz, 1H), 7.36 (d, J=10.6 Hz, 4H), 7.26 (s, 1H), 3.75 (s, 2H), 2.50 (q, J=7.6 Hz, 2H) 2.44 (s, 3H), 1.12 (t, J=7.6 Hz, 3H).

Example 4: Compound A81 Made by Method C

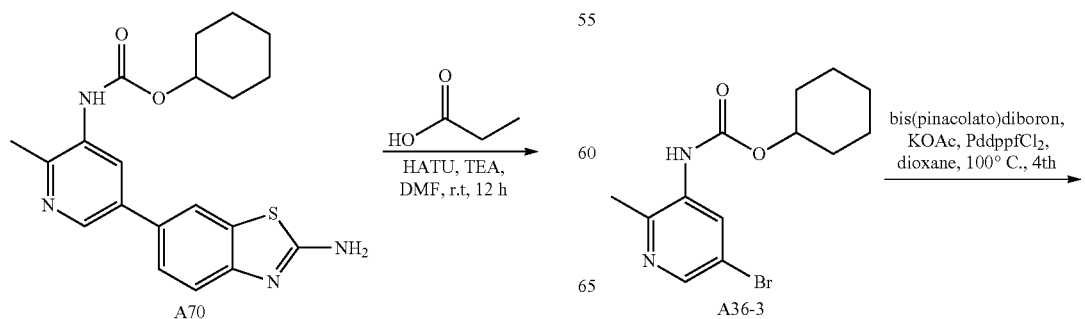

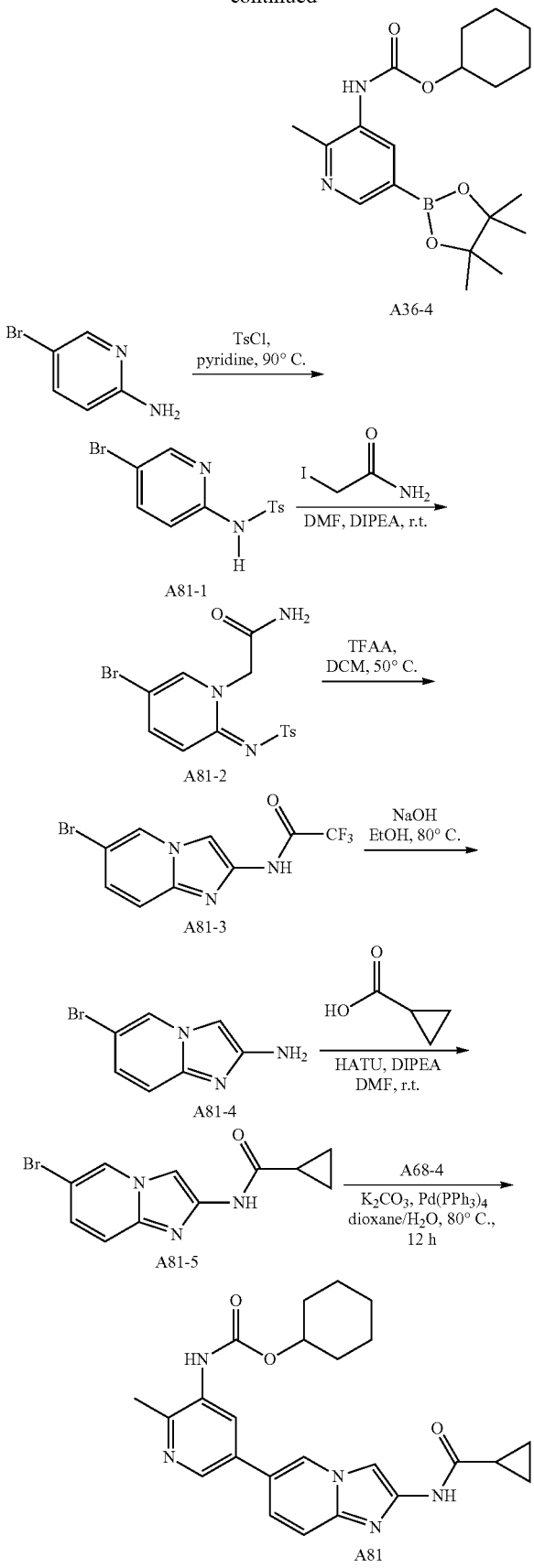

Step 1: Cyclohexyl (2-methyl-5-(4,4,5,5-tetramethyl-1,3,2-dioxaborolan-2-yl)pyridine-3-yl)carbamate A 25 mL flask was charged with A36-3 (80 mg, 0.25 mmol), bis(pinacolato)diboron (95 mg, 0.38 mmol), KOAc (60 mg, 0.63 mmol) and Pd(dppf)Cl$_2$ (18 mg, 0.03 mmol) followed by addition of 3 mL dioxane. The equipment was evacuated and refilled with N$_2$ three times. The reaction was carried out at 100° C. for 3 h. Then the mixture was filtered and the filtrate was concentrated to give a brown oil (200 mg) without further purification for next step.

Step 2: N-(5-bromopyridin-2-yl)-4-methylbenzenesulfonamide

A mixture of 5-bromopyridin-2-amine (20 g, 115.6 mmol) and TsCl (24.2 g, 127.2 mmol) in 80 mL pyridine was heated to 90° C. overnight. After cooled to r.t., the solvent was removed by vacuum. 100 mL was poured into the residue. The resulting precipitate was filtered. The cake was washed with water, dried over vacuum to give a white solid (35.5 g, 93%). $^1$H NMR (400 MHz, DMSO-d6) δ 11.25 (s, 1H), 8.27 (s, 1H), 7.89 (d, J=8.8 Hz, 1H), 7.79 (d, J=8.0 Hz, 2H), 7.37 (d, J=8.0 Hz, 2H), 7.03 (d, J=8.8 Hz, 1H), 2.35 (s, 3H).

Step 3: (Z)-2-(5-bromo-2-(tosylimino)pyridin-1(2H)-yl)acetamide

A mixture of A81-1 (35.5 g, 107.7 mmol), DIPEA (16.7 g, 129.2 mmol) and 2-iodoacetamide (23.9 g, 129.2 mmol) in 80 mL DMF was stirred at r.t. overnight. After that, 1 L water was added. he resulting precipitate was filtered. The cake was washed with water, dried over vacuum to give a grey solid (50.0 g, crude). $^1$H NMR (400 MHz, DMSO-d6) δ 8.37 (s, 1H), 7.87 (d, J=9.6 Hz, 1H), 7.79 (s, 1H), 7.65 (d, J=7.6 Hz, 2H), 7.39 (br s, 1H), 7.30-7.26 (m, 3H), 4.78 (s, 2H), 2.34 (s, 3H).

Step 4: N-(6-bromoimidazo[1,2-a]pyridin-2-yl)-2,2,2-trifluoroacetamide

To a stirred solution of A81-2 (18 g, 46 mmol) in 80 mL CH$_2$Cl$_2$ at r.t., TFAA (48.3 g, 230 mmol) was added. The mixture was stirred at 60° C. overnight. After cooled to r.t., the mixture was basified by sat. aq. NaHCO$_3$ to pH=7. The resulting precipitate was filtered. The cake was washed with water. The filtrate was extracted with dichloromethane. The combined organic phases were dried over Na$_2$SO$_4$ and the solvent was removed by vacuum. The residue was recrystallized in petroleum ether to give a brown solid (15 g, crude). $^1$H NMR (400 MHz, DMSO-d6) δ 12.54 (s, 1H), 8.96 (s, 1H), 8.24 (s, 1H), 7.51 (d, J=9.4 Hz, 1H), 7.42 (d, J=9.4 Hz, 1H).

Step 5: 6-bromoimidazo[1,2-a]pyridin-2-amine

A mixture of A81-3 (15 g, crude, 46 mmol) in 1 N NaOH/EtOH (50 mL/40 mL) was stirred at 80° C. overnight. After cooled to r.t., the aqueous phase was extracted with ethyl acetate. The combined organic phases were dried over Na$_2$SO$_4$ and the solvent was removed by vacuum. The residue was recrystallized in petroleum ether to give a brown solid (8.3 g, 85%). $^1$H NMR (400 MHz, DMSO-d6) δ 8.60 (s, 1H), 7.32-7.05 (m, 2H), 7.00 (s, 1H), 5.22 (s, 2H).

Step 6: N-(6-bromoimidazo[1,2-a]pyridin-2-yl)cyclopropanecarboxamide

A mixture of A81-4 (850 mg, 4.0 mmol), cyclopropanecarboxylic acid (413 mg, 4.8 mmol), DIPEA (774 mg, 6.0 mmol) and HATU (1.8 g, 4.8 mmol) in 10 mL DMF was stirred at r.t. overnight. After 100 mL water was added, the resulting precipitate was filtered. The cake was washed with ethyl acetate, dried under vacuum to give a pink solid (450 mg, 40%). $^1$H NMR (400 MHz, DMSO-d6) δ 11.03 (s, 1H), 8.87 (s, 1H), 8.06 (s, 1H), 7.40 (d, J=9.6 Hz, 1H), 7.31 (d, J=9.6 Hz, 1H), 1.92-1.91 (m, 1H), 0.80-0.76 (m, 4H).

Step 6: Cyclohexyl (5-(2-(cyclopropanecarboxamido)imidazo[1,2-a]pyridin-6-yl)-2-methylpyridin-3-yl)carbamate (A81)

A 25 mL flask was charged with A36-4 (200 mg, crude, 0.25 mmol), A81-5 (70 mg, 0.25 mmol), K$_2$CO$_3$ (69 mg, 0.5 mmol) and Pd(PPh$_3$)$_4$ (29 mg, 0.025 mmol) followed by addition of dioxane/H$_2$O (3 mL/0.3 mL). The equipment was evacuated and refilled with N$_2$ three times. The reaction was carried out at 80° C. for 12 h. After the solvent was removed by vacuum, the residue was purified by column chromatography (dichloromethane:methanol=100:2) to give a white solid (43 mg, 40%). $^1$H NMR (400 MHz, DMSO-d6) δ 10.99 (s, 1H), 9.12 (s, 1H), 8.95 (s, 1H), 8.56 (s, 1H), 8.10-8.02 (m, 2H), 7.52 (s, 2H), 4.70-4.57 (m, 1H), 2.45 (s, 3H), 2.00-1.89 (m, 3H), 1.79-1.68 (m, 2H), 1.58-1.20 (m, 6H), 0.86-0.75 (m, 4H).

Example 5: Compound A50 Made by Method D

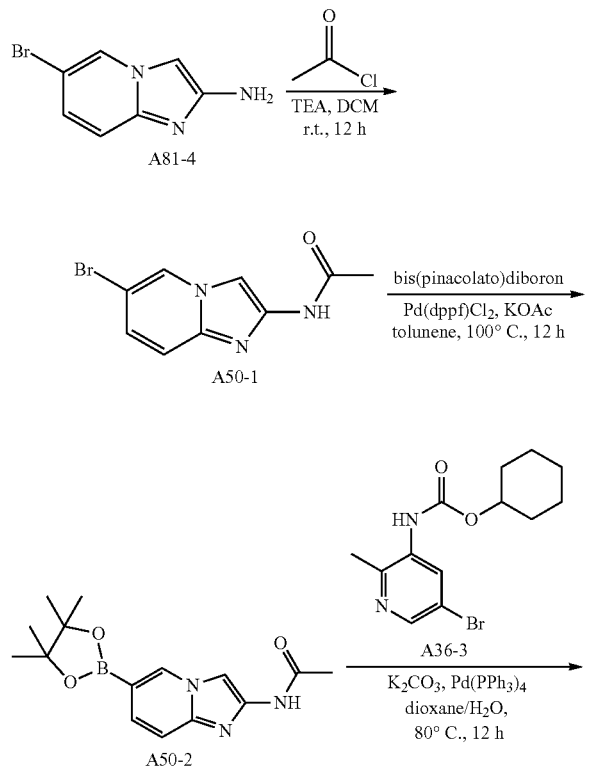

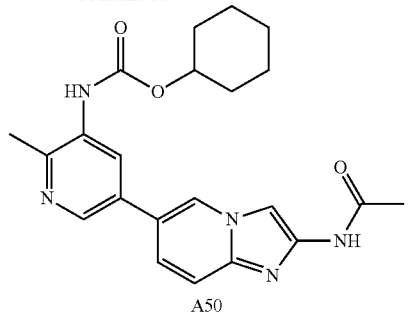

Step 1: N-(6-bromoimidazo[1,2-a]pyridin-2-yl)acetamide

To a stirred solution of A81-4 (850 mg, 4.0 mmol) and TEA (606 mg, 6.0 mmol) in 10 mL dichloromethane at 0° C., acetyl chloride (345 mg, 4.4 mmol) was added dropwise. The reaction was stirred at r.t. overnight. After filtered, the cake was washed with dichloromethane to give A50-1 as a white solid (940 mg, 93%).

Step 2: N-(6-(4,4,5,5-tetramethyl-1,3,2-dioxaborolan-2-yl)imidazo[1,2-a]pyridine-2-yl)acetamide A 25 mL flask was charged with A50-1 (200 mg, 0.94 mmol), bis(pinacolato)diboron (264 mg, 1.04 mmol), KOAc (294 mg, 3.0 mmol) and Pd(dppf)Cl$_2$ (42 mg, 0.05 mmol) followed by addition of 3 mL toluene. The equipment was evacuated and refilled with N$_2$ three times. The reaction was carried out at 100° C. for 12 h. Then the mixture was filtered and the filtrate was concentrated to give A50-2 as a brown solid (260 mg, crude) without further purification for next step.

Step 3: Cyclohexyl (5-(2-acetamidoimidazo[1,2-a]pyridin-6-yl)-2-methylpyridin-3-yl)carbamate (A50)

A 25 mL flask was charged with A36-3 (62 mg, 0.2 mmol), A50-2 (60 mg, 0.2 mmol), K$_2$CO$_3$ (70 mg, 0.5 mmol) and Pd(PPh$_3$)$_4$ (23 mg, 0.02 mmol) followed by addition of dioxane/H$_2$O (4 mL/0.4 mL). The equipment was evacuated and refilled with N$_2$ three times. The reaction was carried out at 80° C. for 12 h. After the solvent was removed by vacuum, the residue was purified by column chromatography (dichloromethane:methanol=100:2) to give A50 as a white solid (12 mg, 15%). $^1$H NMR (400 MHz, DMSO-d6) δ 10.73 (s, 1H), 9.15 (s, 1H), 8.96 (s, 1H), 8.55 (s, 1H), 8.13 (s, 1H), 8.07 (s, 1H), 7.52 (s, 2H), 4.70-4.57 (m, 1H), 2.45 (s, 3H), 2.08 (s, 3H), 1.95-1.90 (m, 2H), 1.80-1.66 (m, 2H), 1.57-1.50 (m, 1H), 1.49-1.26 (m, 5H).

Example 6: Compound A56 Made by Method E

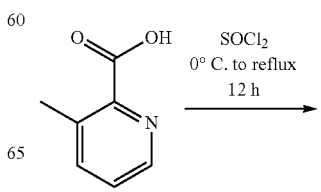

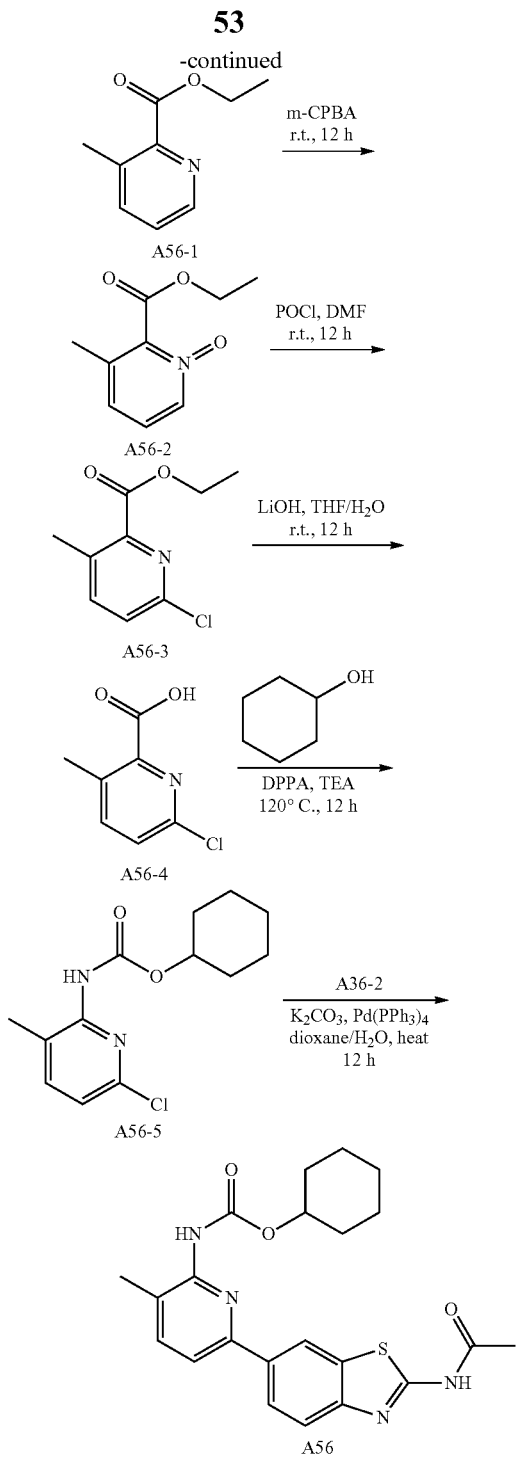

Step 1: ethyl 3-methylpicolinate

To a stirred solution of 3-methylpicolinic acid (2.74 g, 20 mmol) in 50 mL EtOH at 0° C., SOCl₂ (2.60 g, 60 mmol) was added dropwise. After addition, the mixture was stirred at reflux overnight. After cooled to r.t., the mixture was basified with NaHCO₃. The aqueous phase was extracted with ethyl acetate. The combined organic phases were dried over Na₂SO₄ and the solvent was removed by vacuum to give A56-1 as a pail oil (2.60 g, 79%). ¹H NMR (400 MHz, CDCl₃) δ 8.54 (s, 1H), 7.60 (d, J=7.4 Hz, 1H), 7.32 (s, 1H), 4.46 (q, J=6.8 Hz, 2H), 2.58 (s, 3H), 1.44 (t, J=6.8 Hz, 3H).

Step 2: 2-(ethoxycarbonyl)-3-methylpyridine 1-oxide

To a stirred solution of A56-1 (2.60 g, 15.8 mmol) in 50 mL dichloromethane at 0° C., m-CPBA (3.84 g, 18.9 mmol) was added in portions. After stirred at r.t. overnight, the mixture was diluted with dichloromethane. The organic phase was washed with sat. aq. NaHCO₃. The organic phase was dried with Na₂SO₄ and the solvent was removed by vacuum. The residue was purified by column chromatography (dichloromethane:methanol=100:2) to give A56-2 as a brown solid (2.23 g, 78%). ¹H NMR (400 MHz, CDCl₃) δ 8.07 (d, J=4.8 Hz, 1H), 7.21-7.15 (m, 1H), 7.12 (d, J=6.8 Hz, 1H), 4.50 (q, J=6.4 Hz, 2H), 2.29 (s, 3H), 1.41 (t, J=6.4 Hz, 3H).

Step 3: ethyl 6-chloro-3-methylpicolinate

To a stirred 20 mL DMF solution at 0° C., POCl₃ (3.77 g, 24.6 mmol) was added dropwise. After stirred at 0° C. for 30 min, a DMF solution of A56-2 (2.23 g, 12.3 mmol) was added. The reaction was carried out at r.t. overnight. After quenched with water, the mixture was basified by NaHCO₃. The aqueous phase was extracted with petroleum ether:ethyl acetate=1:1. The combined organic phases were dried over Na₂SO₄ and the solvent was removed by vacuum to give A56-3 as a pail oil (1.68 g, 68%). ¹H NMR (400 MHz, CDCl₃) δ 7.56 (d, J=8.0 Hz, 1H), 7.35 (d, J=8.0 Hz, 1H), 4.45 (q J=7.0 Hz, 2H), 2.53 (s, 3H), 1.43 (t, J=7.0 Hz, 3H).

Step 3: 6-chloro-3-methylpicolinic acid

A mixture of A56-3 (800 mg, 4.0 mmol) and LiOH (480 mg, 20.0 mmol) in 7 mL THF/H₂O (6:1) was stirred at r.t. overnight. After acified by 6 N HCl to pH=4. The aqueous phase was extracted with ethyl acetate. The combined organic phases were dried over Na₂SO₄ and the solvent was removed by vacuum to give A56-4 as a white solid (680 mg, 99%). ¹H NMR (400 MHz, CDCl₃) δ 10.97 (br s, 1H), 7.69 (d, J=8.0 Hz, 1H), 7.48 (d, J=8.0 Hz, 1H), 2.75 (s, 3H).

Step 4: Cyclohexyl (6-chloro-3-methylpyridin-2-yl)carbamate

To a stirred solution of A56-4 (172 mg, 1.0 mmol) and TEA (150 mg, 1.5 mmol) in 2 mL cyclohexanol at 120° C., DPPA (413 mg, 1.5 mmol) was added dropwise. After stirred at 120° C. overnight, the solvent was removed by vacuum. The residue was purified by column chromatography (petroleum ether:ethyl acetate=100:4) to give A56-5 as a white solid (170 mg, 63%). ¹H NMR (400 MHz, CDCl₃) δ 7.50 (d, J=8.0 Hz, 1H), 7.09 (d, J=8.0 Hz, 1H), 6.76 (s, 1H), 4.80-4.64 (m, 1H), 2.27 (s, 3H), 1.92-1.90 (m, 2H), 1.80-1.74 (m, 2H), 1.56-1.19 (m, 6H).

Step 5: Cyclohexyl (6-(2-acetamidobenzo[d]thiazol-6-yl)-3-methylpyridin-2-yl) Carbamate (A56)

A 25 mL flask was charged with A56-5 (54 mg, 0.2 mmol), A36-2 (63 mg, 0.2 mmol), K₂CO₃ (70 mg, 0.5 mmol) and Pd(PPh₃)₄ (23 mg, 0.02 mmol) followed by addition of dioxane/H₂O (4 mL/0.4 mL). The equipment was evacuated and refilled with N₂ three times. The reaction was carried out at 80° C. for 12 h. After the solvent was removed by vacuum, the residue was purified by column chromatography (petroleum ether:ethyl acetate=3:2) to give A56 as a white solid (33 mg, 39%). $^1$H NMR (400 MHz, DMSO-d6) δ 12.42 (s, 1H), 9.41 (s, 1H), 8.63 (s, 1H), 8.14 (d, J=8.8 Hz, 1H), 7.79 (d, J=8.4 Hz, 2H), 7.73 (d, J=8.0 Hz, 1H), 4.65-4.60 (m, 1H), 2.23 (s, 3H), 2.22 (s, 3H), 1.90-1.87 (m, 2H), 1.72-1.70 (m, 2H), 1.53-1.21 (m, 6H).

Example 7: Compound A66 Made by Method F

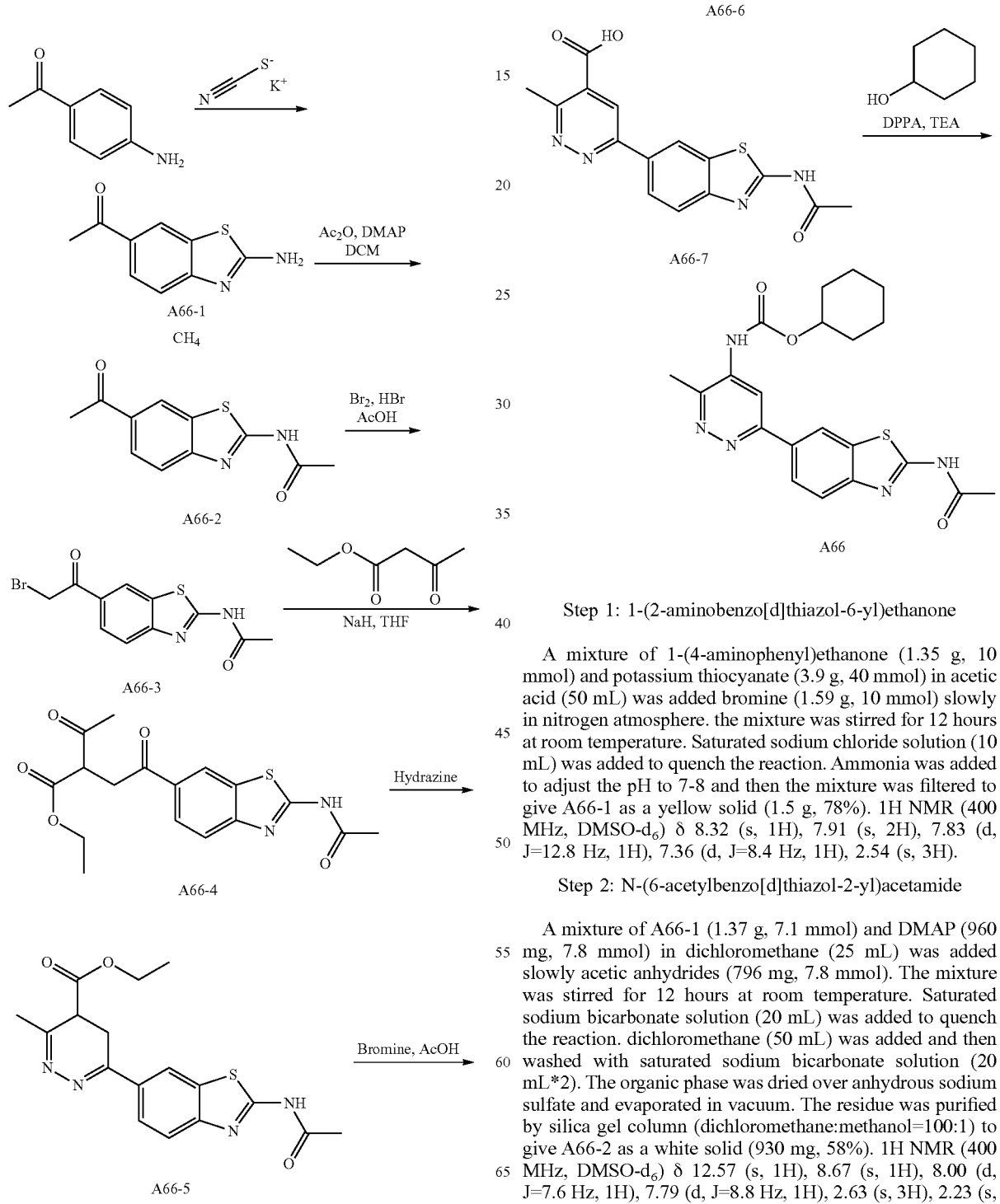

Step 1: 1-(2-aminobenzo[d]thiazol-6-yl)ethanone

A mixture of 1-(4-aminophenyl)ethanone (1.35 g, 10 mmol) and potassium thiocyanate (3.9 g, 40 mmol) in acetic acid (50 mL) was added bromine (1.59 g, 10 mmol) slowly in nitrogen atmosphere. the mixture was stirred for 12 hours at room temperature. Saturated sodium chloride solution (10 mL) was added to quench the reaction. Ammonia was added to adjust the pH to 7-8 and then the mixture was filtered to give A66-1 as a yellow solid (1.5 g, 78%). 1H NMR (400 MHz, DMSO-d$_6$) δ 8.32 (s, 1H), 7.91 (s, 2H), 7.83 (d, J=12.8 Hz, 1H), 7.36 (d, J=8.4 Hz, 1H), 2.54 (s, 3H).

Step 2: N-(6-acetylbenzo[d]thiazol-2-yl)acetamide

A mixture of A66-1 (1.37 g, 7.1 mmol) and DMAP (960 mg, 7.8 mmol) in dichloromethane (25 mL) was added slowly acetic anhydrides (796 mg, 7.8 mmol). The mixture was stirred for 12 hours at room temperature. Saturated sodium bicarbonate solution (20 mL) was added to quench the reaction. dichloromethane (50 mL) was added and then washed with saturated sodium bicarbonate solution (20 mL*2). The organic phase was dried over anhydrous sodium sulfate and evaporated in vacuum. The residue was purified by silica gel column (dichloromethane:methanol=100:1) to give A66-2 as a white solid (930 mg, 58%). 1H NMR (400 MHz, DMSO-d$_6$) δ 12.57 (s, 1H), 8.67 (s, 1H), 8.00 (d, J=7.6 Hz, 1H), 7.79 (d, J=8.8 Hz, 1H), 2.63 (s, 3H), 2.23 (s, 3H).

Step 3: N-(6-(2-bromoacetyl)benzo[d]thiazol-2-yl)acetamide

A mixture of A66-2 (930 mg, 4.0 mmol) in acetic acid (20 mL) was added 48% hydrogen bromide solution (1.5 mL) and bromine (0.21 mL, 4.0 mmol) slowly in nitrogen atmosphere. The mixture was stirred for 12 hours at room temperature. Saturated sodium bicarbonate solution (10 mL) was added to quench the reaction. Dichloromethane (50 mL) was added and then washed with saturated sodium bicarbonate solution (20 mL) and saturated sodium thiosulfate solution (20 mL). The organic phase was dried over anhydrous sodium sulfate and concentrated in vacuum. The residue was poured into petroleum ether (100 mL) to give A66-3 as a brown solid (1.0 g, 80%). 1H NMR (400 MHz, DMSO-$d_6$) δ 12.62 (s, 1H), 8.72 (s, 1H), 8.05 (d, J=8.4 Hz, 1H), 7.83 (d, J=8.4 Hz, 1H), 4.96 (s, 2H), 2.24 (s, 3H).

Step 4: ethyl 4-(2-acetamidobenzo[d]thiazol-6-yl)-2-acetyl-4-oxobutanoate

A suspension of 60% NaH (154 mg, 3.9 mmol) in THF (30 mL) was added ethyl acetoacetate (458 mg, 3.5 mmol) slowly in nitrogen atmosphere. the mixture was stirred for 30 min at room temperature. After the A66-3 (1 g, 3.2 mmol) was added, the mixture was stirred for 2 h at room temperature. Saturated sodium chloride solution (10 mL) was added to quench the reaction and then ethyl acetate (20 ml) was added. The organic phase was washed with saturated sodium chloride solution (20 mL) then dried over anhydrous sodium sulfate and evaporated in vacuum to give A66-4 as a crude product (650 mg, crude). 1H NMR (400 MHz, DMSO-$d_6$) δ 12.59 (s, 1H), 8.73 (s, 1H), 8.02 (d, J=8.4 Hz, 1H), 7.80 (d, J=8.4 Hz, 1H), 4.20 (t, J=6.8 Hz, 1H), 4.16-4.10 (m, 2H), 3.70-3.55 (m, 2H), 2.34 (s, 3H), 2.23 (s, 3H), 1.20 (t, J=6.8 Hz, 3H).

Step 5: ethyl 6-(2-acetamidobenzo[d]thiazol-6-yl)-3-methyl-4,5-dihydropyridazine-4-carboxylate A mixture of A66-4 (650 g, 1.8 mmol) in ethanol and water (ethanol:water=3:1, 25 mL) was added hydrazine hydrate (100 mg, 2.0 mmol). The mixture was stirred for 4 h at 85° C. After the mixture was concentrated, ethyl acetate (20 ml) was added. The organic phase was washed with saturated sodium chloride solution (20 mL*2) then dried over anhydrous sodium sulfate and evaporated in vacuum to give A66-5 as a yellow solid (380 mg, crude).

Step 6: ethyl 6-(2-acetamidobenzo[d]thiazol-6-yl)-3-methylpyridazine-4-carboxylate A mixture of A66-5 (380 mg, 1.06 mmol) in acetic acid (15 mL) was added bromine (220 mg, 1.4 mmol) slowly in nitrogen atmosphere. The mixture was stirred for 4 hours at 100° C. Saturated sodium thiosulfate (5 mL) was added to quench the bromine. ethyl acetate (60 mL) was added and then washed with saturated sodium bicarbonate solution (20 mL) and saturated sodium thiosulfate solution (20 mL). The organic phase was dried over anhydrous sodium sulfate and concentrated in vacuum. The residue was purified by silica gel column (dichloromethane:methanol=100:1) to give A66-6 as a white solid (330 mg, 88%). 1H NMR (400 MHz, DMSO-$d_6$) δ 12.49 (s, 1H), 8.83 (s, 1H), 8.44 (s, 1H), 8.28 (d, J=8.8 Hz, 1H), 7.88 (d, J=8.4 Hz, 1H), 4.45-4.39 (m, 2H), 2.87 (s, 3H), 2.23 (s, 3H), 1.39 (t, J=7.2 Hz, 3H).

Step 7: 6-(2-acetamidobenzo[d]thiazol-6-yl)-3-methylpyridazine-4-carboxylic acid A mixture of A66-6 (165 mg, 0.46 mmol) in THF/$H_2O$ (1:1, 15 mL) was added slowly lithium hydroxide (19 mg, 0.7 mmol). The mixture was stirred for 6 h at room temperature. 1 N HCl was added to adjust the pH to 7 and then the solvent was removed to give the crude product of A66-7 (155 mg, crude). 1H NMR (400 MHz, DMSO-$d_6$) δ 8.72 (s, 1H), 8.18 (d, J=8.4 Hz, 1H), 7.97 (s, 1H), 7.84 (d, J=8.4 Hz, 1H), 2.73 (s, 3H), 2.23 (s, 3H).

Step 8: Cyclohexyl 6-(2-acetamidobenzo[d]thiazol-6-yl)-3-methylpyridazin-4-ylcarbamate (A66)

A mixture of A66-7 (145 mg, 0.44 mmol) and TEA (66.7 mg, 0.66 mmol) in cyclohexanol (5 mL) was added slowly DPPA (182 mg, 0.66 mmol). The mixture was stirred for 5 hours at 110° C. After cool to room temperature, ethyl acetate (40 mL) was added and washed with saturated sodium chloride solution (20 mL). The organic phase was dried over anhydrous sodium sulfate and evaporated in vacuum. The residue was purified by silica gel column (dichloromethane:methanol=50:1) to give A66 as a white solid (7 mg, 4%). 1H NMR (400 MHz, DMSO-$d_6$) δ 12.47 (s, 1H), 9.48 (s, 1H), 8.65 (s, 1H), 8.47 (s, 1H), 8.08 (d, J=8.4 Hz, 1H), 7.86 (d, J=8.4 Hz, 1H), 4.80-4.68 (m, 1H), 2.65 (s, 3H), 2.23 (s, 3H), 2.02-1.91 (m, 2H), 1.81-1.69 (m, 2H), 1.61-1.24 (m, 6H).

TABLE 1

Selected compounds synthesized by Methods A—E

| Compd NO. | Structure | Method | 1H NMR | ESI-MS (m/z): [M + 1]+ |
|---|---|---|---|---|
| A1 | 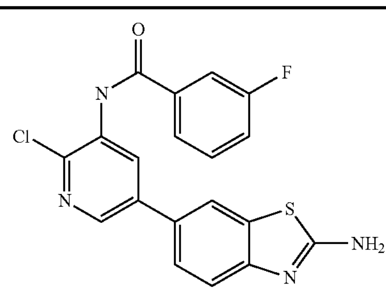 | B | 1H NMR (400 MHz, DMSO-d6) δ 10.19 (s, 1H), 8.62 (s, 1H), 8.52 (s, 1H), 8.12 (s, 1H), 7.85-7.82 (m, 1H), 7.67 (s, 2H), 7.65-7.56 (m, 2H), 7.44 (d, J = 8.4 Hz, 1H), 7.42-7.35 (m, 2H). | |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A2 | 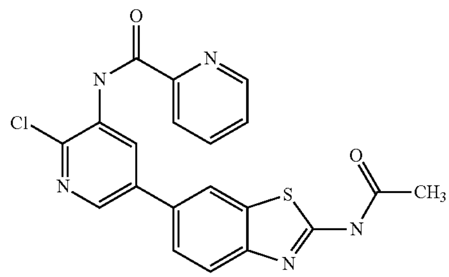 | A | ¹H NMR (400 MHz, DMSO-d6) δ 12.46 (s, 1H), 10.68 (s, 1H), 9.00 (d, J = 2.0 Hz, 1H), 8.80 (d, J = 4.6 Hz, 1H), 8.61 (d, J = 2.0 Hz, 1H), 8.40 (s, 1H), 8.22 (d, J = 8.0 Hz, 1H), 8.16-8.12 (m, 1H), 7.86 (d, J = 8.0 Hz, 1H), 7.78-7.75 (m, 2H), 2.22 (s, 3H). | |
| A3 | 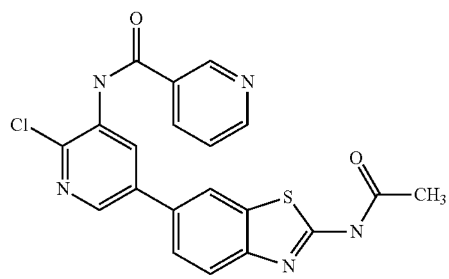 [SMILES: CC(=O)Nc1nc2ccc(-c3cnc(Cl)c(NC(=O)c4cccnc4)c3)cc2s1] | A | ¹H NMR (400 MHz, DMSO-d6) δ 12.46 (s, 1H), 10.60 (s, 1H), 9.18 (s, 1H), 8.82 (d, J = 4.2 Hz, 1H), 8.74 (d, J = 1.8 Hz, 1H), 8.50-8.41 (m, 2H), 8.36 (d. J = 7.6 Hz, 1H), 7.91-7.81 (m, 2H), 7.64-7.61 (m, 1H), 2.22 (s, 3H). | |
| A4 | 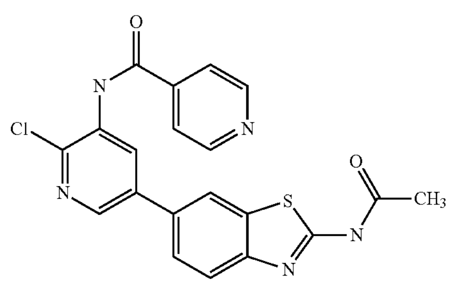 [SMILES: CC(=O)Nc1nc2ccc(-c3cnc(Cl)c(NC(=O)c4ccncc4)c3)cc2s1] | A | ¹H NMR (400 MHz, DMSO-d6) δ 12.47 (s, 1H), 10.69 (s, 1H), 8.84 (d, J = 5.2 Hz, 2H), 8.76 (s, 1H), 8.45 (s, 2H), 7.93 (d, J = 5.2 Hz, 2H), 7.89-7.82 (m, 2H), 2.22 (s, 3H). | |
| A5 | 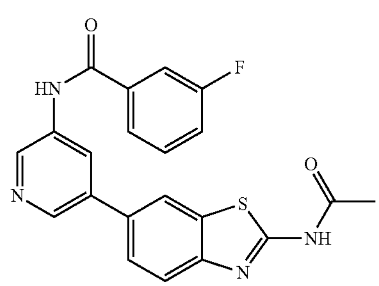 [SMILES: CC(=O)Nc1nc2ccc(-c3cncc(NC(=O)c4cccc(F)c4)c3)cc2s1] | A | ¹H NMR (400 MHz, DMSO-d6) δ 12.45 (s, 1H), 10.75 (s, 1H), 8.86 (s, 1H), 8.71 (s, 1H), 8.51 (s, 1H), 8.36 (s, 1H), 7.86 (d, J = 8.4 Hz, 1H), 7.75 (d, J = 7.6 Hz, 2H), 7.65-7.60 (m, 1H), 7.42-7.35 (m, 2H), 2.22 (s, 3H). | 406.9 |
| A6 | 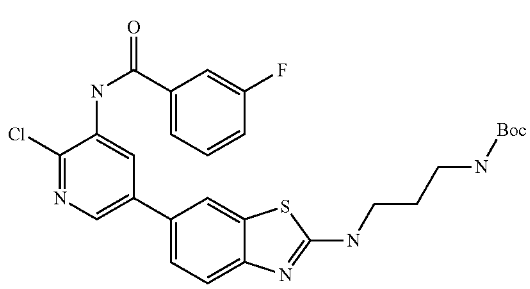 [SMILES: CC(C)(C)OC(=O)NCCCNc1nc2ccc(-c3cnc(Cl)c(NC(=O)c4cccc(F)c4)c3)cc2s1] | D | ¹H NMR (400 MHz, CDCl₃) δ 9.27 (d, J = 17.2 Hz, 1H), 9.22 (s, 1H), 8.40 (s, 1H), 8.24-8.20 (m, 1H), 7.85 (s, 1H), 7.65-7.53 (m, 3H), 7.39-7.35 (m, 1H), 7.29-7.24 (m, 1H), 6.15 (s, 1H), 4.98 (s, 1H), 3.63-3.53 (m, 2H), 3.33-3.25 (m, 2H), 1.87-1.82 (m, 2H), 1.48 (s, 9H). | |

TABLE 1-continued

Selected compounds synthesized by Methods A—E

| Compd NO. | Structure | Method | $^1$H NMR | ESI-MS (m/z): [M + 1]$^+$ |
|---|---|---|---|---|
| A7 | 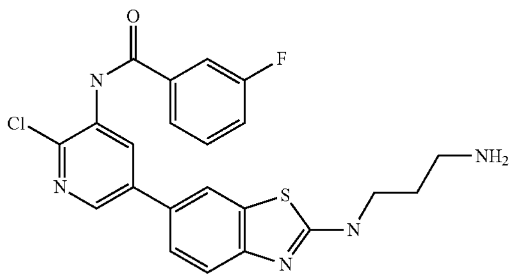 [SMILES: NCCCNc1nc2ccc(-c3cnc(Cl)c(NC(=O)c4cccc(F)c4)c3)cc2s1] | D | $^1$H NMR (400 MHz, DMSO-d6) δ 8.53 (s, 2H), 8.46 (s, 1H), 8.09 (s, 1H), 7.84-7.81 (m, 1H), 7.63-7.58 (m, 2H), 7.47 (d, J = 8.4 Hz, 1H), 7.38-7.33 (m, 2H), 6.04-5.70 (m, 1H), 3.35-3.33 (m, 1H) 3.02 (d, J = 4.6 Hz, 2H), 2.63 (t, J = 6.4 Hz, 1H), 1.70-1.65 (m, 2H). | 455.9 |
| A8 | See Table 1A | A | $^1$H NMR (400 MHz, DMSO-d6) δ 12.44 (s, 1H), 10.16 (s, 1H), 8.79 (s, 1H), 8.38 (s, 1H), 8.19 (s, 1H), 7.85-7.82 (m, 4H), 7.75-7.12 (m, 1H), 7.65-7.60 (m, 1H), 7.41-7.36 (m, 2H), 6.42 (s, 1H), 6.36 (s, 1H), 4.36-4.21 (m, 1H), 4.17-4.05 (m, 1H), 3.14-3.05 (m, 3H), 3.01-2.96 (m, 2H), 2.88-2.76 (m, 3H), 2.56 (d, J = 12.4 Hz, 1H), 2.22 (s, 3H), 2.02 (t, J = 7.4 Hz, 4H), 1.91-1.80 (m, 2H), 1.64-1.55 (m, 1H), 1.54-1.39 (m, 5H), 1.39-1.13 (m, 6H). | 802.9 |
| A9 | See Table 1A | D | $^1$H NMR (400 MHz, DMSO-d6) δ 10.20 (s, 1H), 8.62 (s, 1H), 8.53 (s, 1H), 8.20 (s, 1H), 8.13 (s, 1H), 7.85-7.82 (m, 2H), 7.75-7.73 (m, 1H), 7.68-7.61 (m, 2H), 7.49 (d, J = 8.4 Hz, 1H), 7.43-7.37 (m, 2H), 6.42 (s, 1H), 6.36 (s, 1H), 4.35-4.22 (m, 1H), 4.12-4.11 (m, 1H), 3.40-3.37 (m, 2H), 3.19-3.11 (m, 2H), 3.07-3.06 (m, 1H), 3.04-2.95 (m, 2H), 2.82-2.78 (m, 1H), 2.56 (d, J = 12.4 Hz, 1H), 2.11-2.00 (m, 4H), 1.79-1.67 (m, 2H), 1.65-1.54 (m, 1H), 1.54-1.43 (m, 5H), 1.41-1.32 (m, 2H), 1.32-1.20 (m, 4H), 1.19-1.15 (m, 2H), 1.09 (t, J = 7.0 Hz, 1H). | |
| A10 | 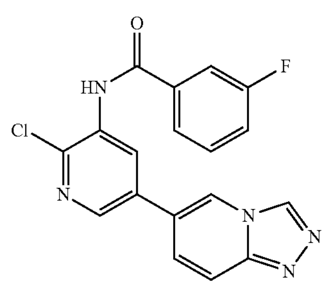 [SMILES: O=C(Nc1cc(-c2ccc3nncn3c2)cnc1Cl)c1cccc(F)c1] | D | $^1$H NMR (400 MHz, CDCl$_3$) δ 9.35 (d, J = 17.6 Hz, 1H), 9.30 (d, J = 2.2 Hz, 1H), 8.91 (s, 1H), 8.43 (s, 1H), 8.41 (d, J = 2.2 Hz, 1H), 8.23-8.20 (m, 1H), 7.91 (d, J = 9.2 Hz, 1H), 7.82 (d, J = 10.6 Hz, 1H), 7.62 (dd, J = 13.9, 6.8 Hz, 1H), 7.40-7.36 (m, 1H), 7.29 (d, J = 8.6 Hz, 1H). | 367.9 |
| A11 | 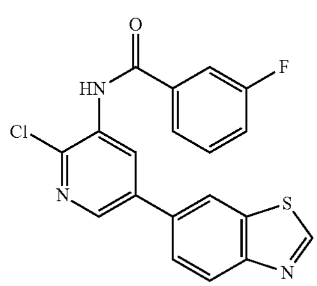 [SMILES: O=C(Nc1cc(-c2ccc3ncsc3c2)cnc1Cl)c1cccc(F)c1] | D | $^1$H NMR (400 MHz, DMSO-d6) δ 10.27 (s, 1H), 9.48 (s, 1H), 8.73 (d, J = 2.4 Hz, 1H), 8.65 (s, 2H), 8.23 (d, J = 8.4 Hz, 1H), 7.94 (d, J = 9.6 Hz, 1H), 7.86-7.82 (m, 1H), 7.68-7.64 (m, 1H), 7.41 (dd, J = 15.6, 8.4 Hz, 2H). | |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A12 | 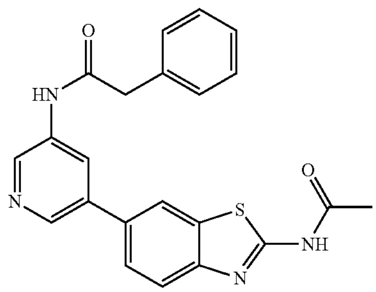 [SMILES: CC(=O)Nc1nc2ccc(-c3cncc(NC(=O)Cc4ccccc4)c3)cc2s1] | A | ¹H NMR (400 MHz, DMSO-d6) δ 12.44 (s, 1H), 10.53 (s, 1H), 8.71 (s, 1H), 8.63 (s, 1H), 8.39 (s, 1H), 8.31 (s, 1H), 7.83 (d, J = 8.4 Hz, 1H), 7.71 (d, J = 8.1 Hz, 1H), 7.41-7.30 (m, 4H), 7.27 (d, J = 6.3 Hz, 1H), 3.72 (s, 2H), 2.22 (s, 3H). | 403.0 |
| A13 | 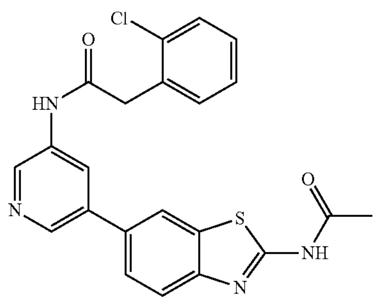 [SMILES: CC(=O)Nc1nc2ccc(-c3cncc(NC(=O)Cc4ccccc4Cl)c3)cc2s1] | A | ¹H NMR (400 MHz, DMSO-d6) δ 10.59 (s, 1H), 8.71 (s, 1H), 8.62 (s, 1H), 8.37 (s, 1H), 8.20 (s, 1H), 7.72 (d, J = 8.0 Hz, 1H), 7.63 (d, J = 8.0 Hz, 1H), 7.52-7.40 (m, 2H), 7.37-7.27 (m, 2H), 3.92 (s, 2H), 2.14 (s, 3H). | 436.9 |
| A14 | 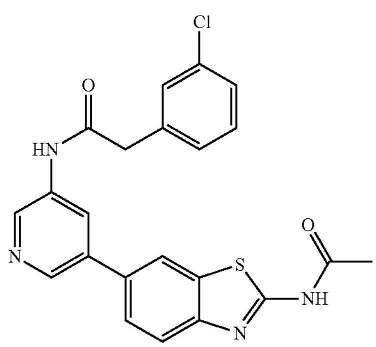 [SMILES: CC(=O)Nc1nc2ccc(-c3cncc(NC(=O)Cc4cccc(Cl)c4)c3)cc2s1] | A | ¹H NMR (400 MHz, DMSO-d6) δ 12.44 (s, 1H), 10.55 (s, 1H), 8.70 (s, 1H), 8.64 (s, 1H), 8.39 (s, 1H), 8.31 (s, 1H), 7.83 (d, J = 8.4 Hz, 1H), 7.71 (d, J = 8.4 Hz, 1H), 7.44 (s, 1H), 7.40-7.31 (m, 3H), 3.76 (s, 2H), 2.22 (s, 3H). | 436.9 |
| A15 | 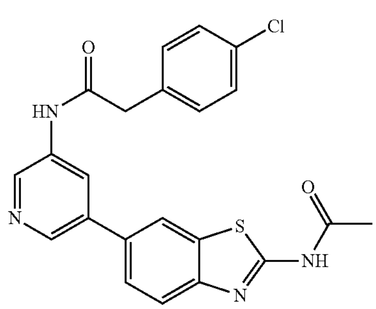 | A | ¹H NMR (400 MHz, DMSO-d6) δ 12.44 (s, 1H), 10.54 (s, 1H), 8.70 (s, 1H), 8.63 (s, 1H), 8.38 (s, 1H), 8.31 (s, 1H), 7.83 (d, J = 8.4 Hz, 1H), 7.70 (d, J = 8.4 Hz, 1H), 7.46-7.30 (m, 4H), 3.73 (s, 2H), 2.22 (s, 3H). | 436.9 |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A16 | 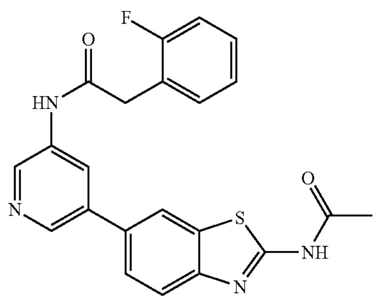 [SMILES: CC(=O)Nc1nc2ccc(-c3cncc(NC(=O)Cc4ccccc4F)c3)cc2s1] | A | ¹H NMR (400 MHz, DMSO-d6) δ 12.44 (s, 1H), 10.58 (s, 1H), 8.71 (s, 1H), 8.64 (s, 1H), 8.40 (s, 1H), 8.31 (s, 1H), 7.83 (d, J = 8.4 Hz, 1H), 7.71 (d, J = 8.4 Hz, 1H), 7.44-7.40 (m, 1H), 7.36-7.31 (m, 1H), 7.22-7.21 (m, 2H), 3.82 (s, 2H), 2.22 (s, 3H). | 420.9 |
| A17 | 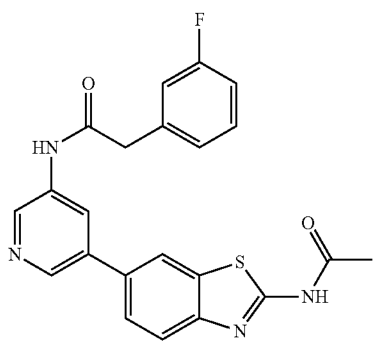 | A | ¹H NMR (400 MHz, DMSO-d6) δ 12.44 (s, 1H), 10.55 (s, 1H), 8.71 (s, 1H), 8.63 (s, 1H), 8.39 (s, 1H), 8.31 (s, 1H), 7.83 (d, J = 8.4 Hz, 1H), 7.71 (d, J = 8.0 Hz, 1H), 7.42-7.34 (m, 1H), 7.20 (d, J = 7.6 Hz, 2H), 7.13-7.07 (m, 1H), 3.76 (s, 2H), 2.22 (s, 3H). | 420.9 |
| A18 | 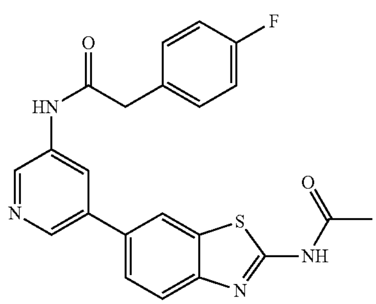 [SMILES: CC(=O)Nc1nc2ccc(-c3cncc(NC(=O)Cc4ccc(F)cc4)c3)cc2s1] | A | ¹H NMR (400 MHz, DMSO-d6) δ 12.44 (s, 1H), 10.53 (s, 1H), 8.70 (s, 1H), 8.63 (s, 1H), 8.38 (s, 1H), 8.31 (s, 1H), 7.83 (d, J = 8.4 Hz, 1H), 7.71 (d, J = 9.0 Hz, 1H), 7.40-7.37 (m, 2H), 7.19-7.14 (m, 2H), 3.72 (s, 2H), 2.22 (s, 3H). | 420.9 |
| A19 | 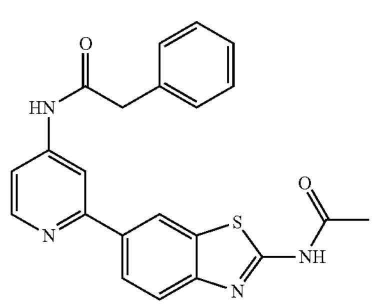 [SMILES: CC(=O)Nc1nc2ccc(-c3cc(NC(=O)Cc4ccccc4)ccn3)cc2s1] | A | ¹H NMR (400 MHz, DMSO-d6) δ 12.44 (s, 1H), 10.66 (s, 1H), 8.57 (s, 1H), 8.52 (d, J = 5.4 Hz, 1H), 8.19 (s, 1H), 8.02 (d, J = 8.4 Hz, 1H), 7.81 (d, J = 8.4 Hz, 1H), 7.51 (d, J = 4.6 Hz, 1H), 7.40-7.31 (m, 4H), 7.27 (d, J = 5.4 Hz, 1H), 3.73 (s, 2H), 2.21 (s, 3H). | 403.0 |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A20 | 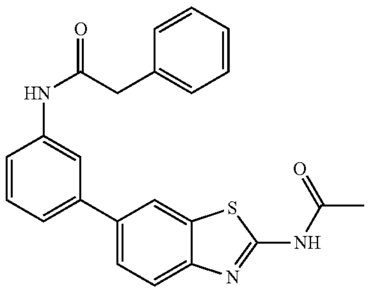 [SMILES: CC(=O)Nc1nc2ccc(-c3cccc(NC(=O)Cc4ccccc4)c3)cc2s1] | A | ¹H NMR (400 MHz, DMSO-d6) δ 12.40 (s, 1H), 10.30 (s, 1H), 8.21 (s, 1H), 7.98 (s, 1H), 7.80 (d, J = 8.4 Hz, 1H), 7.65 (d, J = 8.4 Hz, 1H), 7.57 (d, J = 6.4 Hz, 1H), 7.45-7.30 (m, 6H), 7.27-7.23 (m, 1H), 3.67 (s, 2H), 2.22 (s, 3H). | 401.9 |
| A21 | 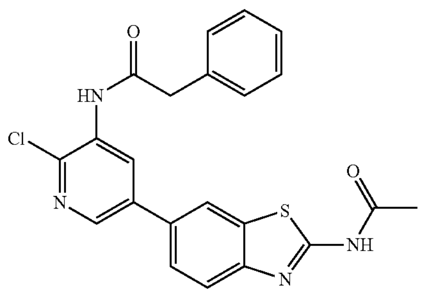 [SMILES: CC(=O)Nc1nc2ccc(-c3cnc(Cl)c(NC(=O)Cc4ccccc4)c3)cc2s1] | B | ¹H NMR (400 MHz, DMSO-d6) δ 9.94 (s, 1H), 8.55 (s, 1H), 8.46 (s, 1H), 8.09 (s, 1H), 7.60 (s, 2H), 7.41-7.30 (m, 5H), 7.30-7.22 (m, 1H), 3.81 (s, 2H). | |
| A22-Pk-52 | 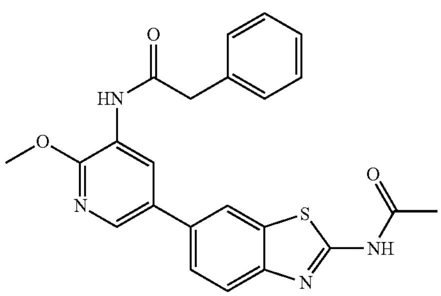 [SMILES: COc1ncc(-c2ccc3nc(NC(C)=O)sc3c2)cc1NC(=O)Cc1ccccc1] | A | ¹H NMR (400 MHz, DMSO-d6) δ 12.38 (s, 1H), 9.70 (s, 1H), 8.67 (s, 1H), 8.23 (s, 1H), 8.21 (s, 1H), 7.78 (d, J = 8.4 Hz, 1H), 7.63 (d, J = 8.4 Hz, 1H), 7.41-7.29 (m, 4H), 7.27-7.23 (m, 1H), 4.01 (s, 3H), 3.82 (s, 2H), 2.21 (s, 3H). | 433.0 |
| A23 | 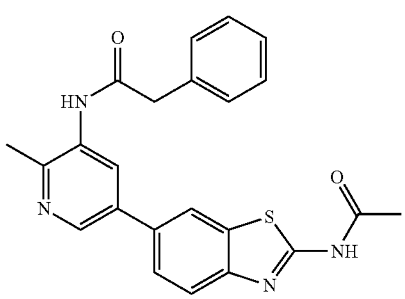 [SMILES: CC(=O)Nc1nc2ccc(-c3cnc(C)c(NC(=O)Cc4ccccc4)c3)cc2s1] | A | ¹H NMR (400 MHz, DMSO-d6) δ 9.84 (s, 1H), 8.62 (s, 1H), 8.29 (s, 1H), 8.14 (s, 1H), 7.79 (d, J = 8.4 Hz, 1H), 7.70 (d, J = 8.4 Hz, 1H), 7.40-7.33 (m, 4H), 7.28-7.24 (m, 1H), 3.76 (s, 2H), 2.44 (s, 3H), 2.20 (s, 3H). | 416.9 |
| A24 | 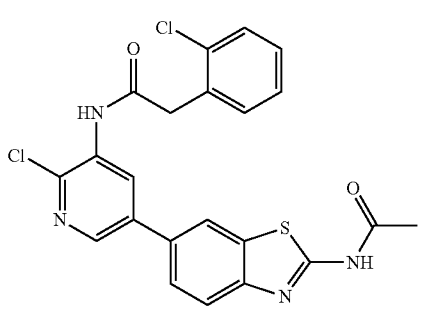 [SMILES: CC(=O)Nc1nc2ccc(-c3cnc(Cl)c(NC(=O)Cc4ccccc4Cl)c3)cc2s1] | A | ¹H NMR (400 MHz, DMSO-d6) δ 12.45 (s, 1H), 10.08 (s, 1H), 8.58 (s, 1H), 8.51 (s, 1H), 8.35 (s, 1H), 7.82 (d, J = 8.4 Hz, 1H), 7.73 (d, J = 8.4 Hz, 1H), 7.53-7.40 (m, 2H), 7.35-7.30 (m, 2H), 4.01 (s, 2H), 2.21 (s, 3H). | |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A25 | 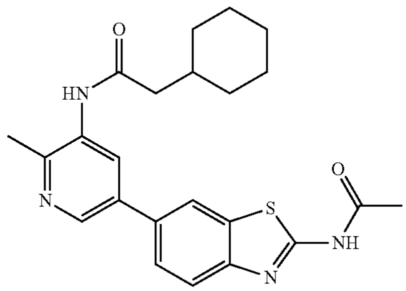 [SMILES: CC(=O)Nc1nc2ccc(-c3cnc(C)c(NC(=O)CC4CCCCC4)c3)cc2s1] | A | ¹H NMR (400 MHz, DMSO-d6) δ 12.41 (s, 1H), 9.51 (s, 1H), 8.62 (s, 1H), 8.31 (s, 1H), 8.12 (s, 1H), 7.82 (d, J = 8.4 Hz, 1H), 7.72 (d, J = 8.4 Hz, 1H), 2.45 (s, 3H), 2.29 (d, J = 6.8 Hz, 2H), 2.22 (s, 3H), 1.84-1.59 (m, 5H), 1.31-1.12 (m, 3H), 1.06-0.92 (m, 2H). | 423.0 |
| A26 | 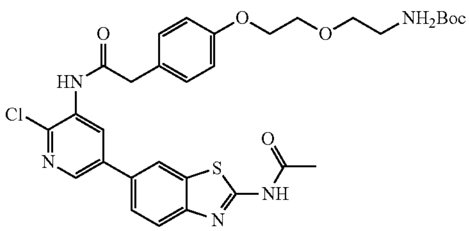 | A | ¹H NMR (400 MHz, DMSO-d6) δ 12.44 (s, 1H), 9.89 (s, 1H), 8.57 (s, 1H), 8.50 (s, 1H), 8.35 (s, 1H), 7.83 (d, J = 8.4 Hz, 1H), 7.74 (d, J = 8.4 Hz, 1H), 7.28 (d, J = 8.2 Hz, 2H), 6.91 (d, J = 8.2 Hz, 2H), 6.81 (d, J = 14.6 Hz, 1H), 4.11-4.00 (m, 2H), 3.74 (s, 2H), 3.72-3.70 (m, 2H), 3.44 (t, J = 6.0 Hz, 3H), 3.10-3.06 (m, 2H), 2.22 (s, 3H). 1.36 (s, 9H). | 661.9 |
| A27 | See Table 1A | A | ¹H NMR (400 MHz, DMSO-d6) δ 12.45 (s, 1H), 9.90 (s, 1H), 8.57 (s, 1H), 8.50 (s, 1H), 8.35 (s, 1H), 7.83 (d, J = 8.4 Hz, 2H), 7.74 (d, J = 8.4 Hz, 2H), 7.28 (d, J = 8.4 Hz, 2H), 6.91 (d, J = 8.4 Hz, 2H), 6.42 (s, 1H), 6.35 (s, 1H), 4.38-4.23 (m, 1H), 4.14-4.09 (m, 1H), 4.09-4.05 (m, 2H), 3.74 (s, 2H), 3.72-3.71 (m, 2H), 3.46 (t, J = 5.6 Hz, 2H), 3.22-3.18 (m, 2H), 3.08-3.06 (m, 1H), 2.99-2.96 (m, 2H), 2.80 (dd, J = 12.6, 5.0 Hz, 1H), 2.56 (d, J = 12.6 Hz, 1H), 2.22 (s, 3H), 2.06-2.00 (m, 4H), 1.62-1.59 (m, 1H), 1.48-1.42 (m, 5H), 1.39-1.19 (m, 5H). | |
| A28 | 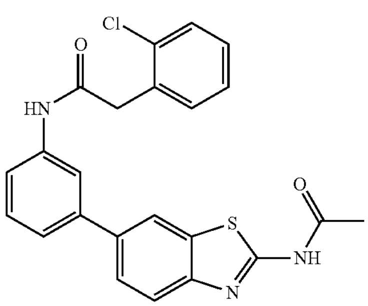 [SMILES: CC(=O)Nc1nc2ccc(-c3cccc(NC(=O)Cc4ccccc4Cl)c3)cc2s1] | A | ¹H NMR (400 MHz, DMSO-d6) δ 12.39 (s, 1H), 10.35 (s, 1H), 8.21 (s, 1H), 8.01 (s, 1H), 7.79 (d, J = 8.4 Hz, 1H), 7.65 (d, J = 8.0 Hz, 1H), 7.57-7.53 (m, 1H), 7.44 (s, 2H), 7.42-7.38 (m, 2H), 7.35-7.27 (m, 2H), 3.87 (s, 2H), 2.21 (s, 3H). | |
| A29 | 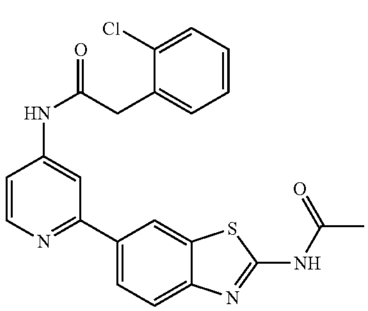 [SMILES: CC(=O)Nc1nc2ccc(-c3cc(NC(=O)Cc4ccccc4Cl)ccn3)cc2s1] | A | ¹H NMR (400 MHz, DMSO-d6) δ 12.44 (s, 1H), 10.74 (s, 1H), 8.57 (s, 1H), 8.53 (s, 1H), 8.22 (s, 1H), 8.03 (d, J = 8.4 Hz, 1H), 7.81 (d, J = 8.4 Hz, 1H), 7.48 (s, 1H), 7.48-7.43 (m, 2H), 7.36-7.31 (m, 2H), 3.94 (s, 2H), 2.21 (s, 3H). | |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A30 | 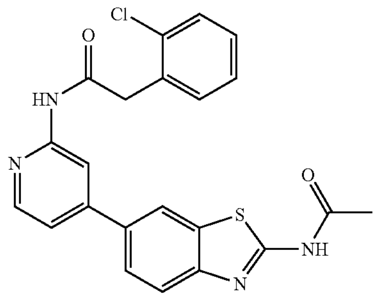 [SMILES: CC(=O)Nc1nc2ccc(-c3ccnc(NC(=O)Cc4ccccc4Cl)c3)cc2s1] | A | ¹H NMR (400 MHz, DMSO-d6) δ 10.88 (s, 1H), 8.43 (s, 1H), 8.39 (d, J = 5.2 Hz, 1H), 8.36 (s, 1H), 7.81 (d, J = 8.4 Hz, 1H), 7.75 (d, J = 8.3 Hz, 1H), 7.50-7.43 (m, 3H), 7.33-7.29 (m, 2H), 3.97 (s, 2H), 2.21 (s, 3H). | |
| A31 | 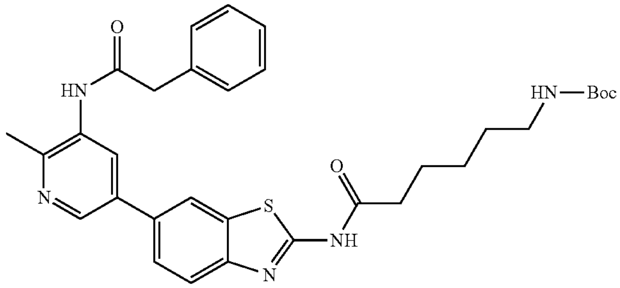 [SMILES: Cc1ncc(-c2ccc3nc(NC(=O)CCCCCNC(=O)OC(C)(C)C)sc3c2)cc1NC(=O)Cc1ccccc1] | D | ¹H NMR (400 MHz, DMSO-d6) δ 12.39 (s, 1H), 9.82 (s, 1H), 8.62 (s, 1H), 8.30 (s, 1H), 8.14 (s, 1H), 7.80 (d, J = 8.4 Hz, 1H), 7.71 (d, J = 8.4 Hz, 1H), 7.39-7.33 (m, 4H), 7.28-7.24 (m, 1H), 6.79-6.76 (m, 1H), 3.75 (s, 2H), 3.49 (s, 2H), 2.90 (dd, J = 12.2, 6.0 Hz, 2H), 2.43 (s, 3H), 1.67-1.55 (m, 2H), 1.37 (s, 9H), 1.40-1.36 (m, 2H), 1.30-1.26 (m, 2H). | |
| A32 | See Table 1A | A | ¹H NMR (400 MHz, DMSO-d6) δ 12.37 (s, 1H), 9.83 (s, 1H), 8.62 (s, 1H), 8.30 (s, 1H), 8.14 (s, 1H), 7.81-7.70 (m, 4H), 7.39-7.33 (m, 4H), 7.26-7.24 (m, 1H), 6.42 (s, 1H), 6.36 (s, 1H), 4.34-4.25 (m, 1H), 4.12-4.11 (m, 1H), 3.75 (s, 2H), .3.50 (s, 2H), 3.11-3.05 (m, 1H), 3.02-2.97 (m, 4H), 2.80 (dd, J = 12.4, 5.0 Hz, 1H), 2.56 (d, J = 12.4 Hz, 1H), 2.43 (s, 3H), 2.02 (dd, J = 11.0. 6.6 Hz, 4H), 1.67-1.53 (m, 3H), 1.52-1.37 (m, 7H), 1.38-1.24 (m, 6H), 1.17-1.19 (m, 2H). | |
| A33 | 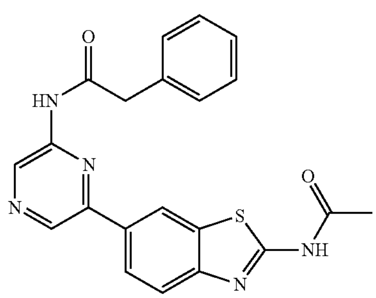 [SMILES: CC(=O)Nc1nc2ccc(-c3cncc(NC(=O)Cc4ccccc4)n3)cc2s1] | A | ¹H NMR (400 MHz, DMSO-d6) δ 12.52 (s, 1H), 11.10 (s, 1H), 9.25 (s, 1H), 9.00 (s, 1H), 8.73 (s, 1H), 8.21 (d, J = 8.4 Hz, 1H), 7.87 (d, J = 8.4 Hz, 1H), 7.39-7.32 (m, 4H), 7.28-7.24 (m, 1H), 3.82 (s, 2H), 2.23 (s, 3H). | 403.9 |
| A34 | 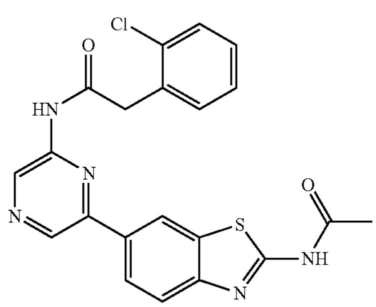 [SMILES: CC(=O)Nc1nc2ccc(-c3cncc(NC(=O)Cc4ccccc4Cl)n3)cc2s1] | A | ¹H NMR (400 MHz, DMSO-d6) δ 12.51 (s, 1H), 11.16 (s, 1H), 9.23 (s, 1H), 9.01 (s, 1H), 8.74 (s, 1H), 8.22 (d, J = 8.4 Hz, 1H), 7.88 (d, J = 8.4 Hz, 1H), 7.51-7.43 (m, 2H), 7.38-7.23 (m, 2H), 4.03 (s, 3H), 2.23 (s, 3H). | |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A35 | 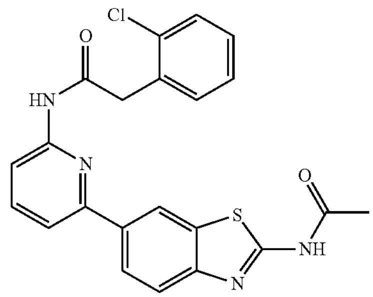 [SMILES: CC(=O)Nc1nc2ccc(-c3cccc(NC(=O)Cc4ccccc4Cl)n3)cc2s1] | A | ¹H NMR (400 MHz, DMSO-d6) δ 12.45 (s, 1H), 10.80 (s, 1H), 8.68 (s, 1H), 8.19 (d, J = 8.6 Hz, 1H), 7.99 (d, J = 7.6 Hz, 1H), 7.89-7.82 (m, 2H), 7.73 (d, J = 7.6 Hz, 1H), 7.46-7.44 (m, 2H), 7.33-7.31 (m, 2H), 3.99 (s, 2H), 2.22 (s, 3H). | 436.8 |
| A36 | 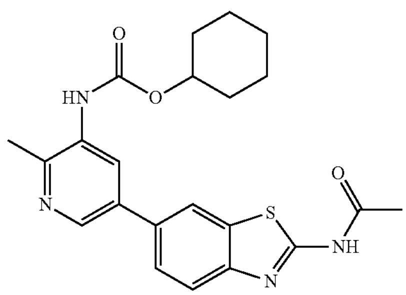 [SMILES: CC(=O)Nc1nc2ccc(-c3cnc(C)c(NC(=O)OC4CCCCC4)c3)cc2s1] | D | ¹H NMR (400 MHz, DMSO-d6) δ 12.41 (s, 1H), 9.12 (s, 1H), 8.59 (s, 1H), 8.31 (s, 1H), 8.10 (s, 1H), 7.82 (d, J = 8.4 Hz, 1H), 7.72 (d, J = 8.4 Hz, 1H), 4.74-4.56 (m, 1H), 2.46 (s, 3H), 2.22 (s, 3H), 1.92-1.89 (m, 2H), 1.75-1.67 (m, 2H), 1.56-1.25 (m, 6H). | 424.9 |
| A37 | 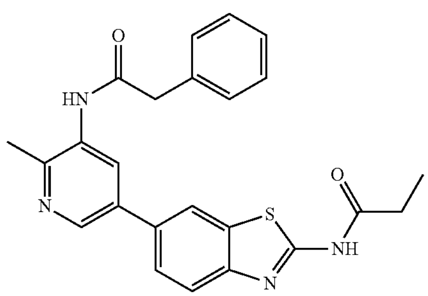 [SMILES: CCC(=O)Nc1nc2ccc(-c3cnc(C)c(NC(=O)Cc4ccccc4)c3)cc2s1] | B | ¹H NMR (400 MHz, DMSO-d6) δ 12.37 (s, 1H), 9.80 (s, 1H), 8.63 (s, 1H), 8.31 (s, 1H), 8.15 (s, 1H), 7.80 (d, J = 8.0 Hz, 1H), 7.71 (d, J = 8.4 Hz, 1H), 7.36 (d, J = 10.6 Hz, 4H), 7.26 (s, 1H), 3.75 (s, 2H), 2.50 (q, J = 7.6 Hz, 2H), 2.44 (s, 3H), 1.12 (t, J = 7.6 Hz, 3H). | |
| A38 | 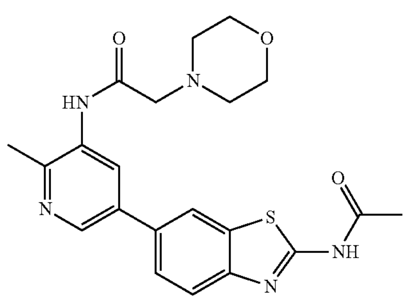 [SMILES: CC(=O)Nc1nc2ccc(-c3cnc(C)c(NC(=O)CN4CCOCC4)c3)cc2s1] | A | ¹H NMR (400 MHz, DMSO-d6) δ 12.41 (s, 1H), 9.60 (s, 1H), 8.62 (s, 1H), 8.36 (s, 1H), 8.31 (s, 1H), 7.83 (d, J = 8.4 Hz, 1H), 7.72 (d, J = 8.4 Hz, 1H), 3.80-3.60 (m, 4H), 3.20 (s, 2H), 2.60-2.50 (m, 4H), 2.49 (s, 3H), 2.22 (s, 3H). | 426.0 |
| A39 | 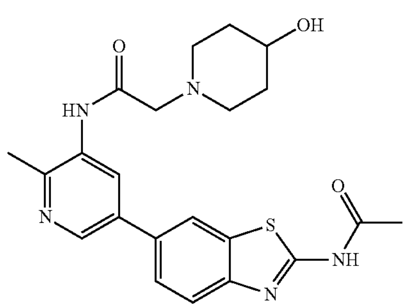 [SMILES: CC(=O)Nc1nc2ccc(-c3cnc(C)c(NC(=O)CN4CCC(O)CC4)c3)cc2s1] | A | ¹H NMR (400 MHz, DMSO-d6) δ 12.41 (s, 1H), 9.61 (s, 1H), 8.60 (s, 1H), 8.44 (s, 1H), 8.31 (s, 1H), 7.83 (d, J = 8.4 Hz, 1H), 7.71 (d, J = 8.4 Hz, 1H), 4.65 (d, J = 2.8 Hz, 1H), 3.52 (s, 1H), 3.15 (s, 2H), 2.84-2.82 (m, 2H), 2.47 (s, 3H), 2.35-2.30 (m, 2H), 2.22 (s, 3H), 1.81-1.78 (m, 2H), 1.58-1.49 (m, 2H). | |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A40 | 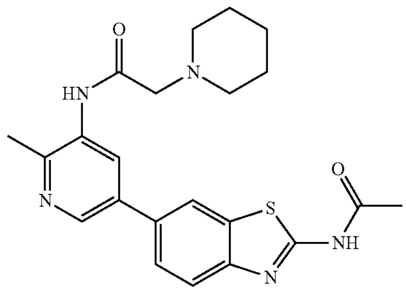 | A | ¹H NMR (400 MHz, DMSO-d6) δ 12.41 (s, 1H), 9.62 (s, 1H), 8.60 (s, 1H), 8.45 (s, 1H), 8.31 (s, 1H), 7.83 (d, J = 8.4 Hz, 1H), 7.71 (d, J = 8.4 Hz, 1H), 3.13 (s, 2H), 2.60-2.53 (m, 4H), 2.47 (s, 3H), 2.22 (s, 3H), 1.69-1.53 (m, 4H), 1.44-1.43 (m, 2H). | 424.0 |
| A41 | 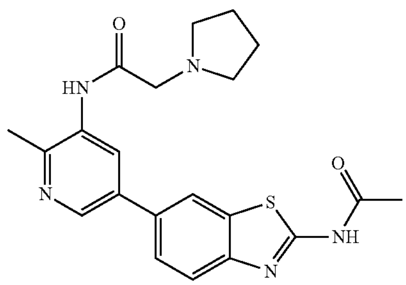 | A | ¹H NMR (400 MHz, DMSO-d6) δ 12.41 (s, 1H), 9.59 (s, 1H), 8.62 (s, 1H), 8.31 (d, J = 3.8 Hz, 2H), 7.83 (d, J = 8.4 Hz, 1H), 7.72 (d, J = 8.4 Hz, 1H), 3.33 (s, 2H), 2.70-2.65 (m, 4H), 2.45 (s, 3H), 2.22 (s, 3H), 1.83-1.72 (m, 4H). | 408.0 (M − H) |
| A42 | 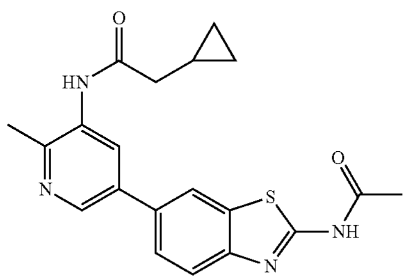 [SMILES: CC(=O)Nc1nc2ccc(-c3cnc(C)c(NC(=O)CC4CC4)c3)cc2s1] | A | ¹H NMR (400 MHz, DMSO-d6) δ 12.41 (s, 1H), 9.44 (s, 1H), 8.62 (s, 1H), 8.32 (s, 1H), 8.16 (s, 1H), 7.82 (d, J = 8.4 Hz, 1H), 7.72 (d, J = 8.4 Hz, 1H), 2.46 (s, 3H), 2.31 (d, J = 7.0 Hz, 2H), 2.22 (s, 3H), 1.13-1.09 (m, 1H), 0.52-0.51 (m, 2H), 0.25-0.24 (m, 2H). | 379.0 [M − H]⁻ |
| A43 | 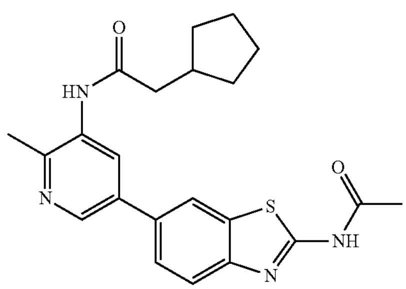 [SMILES: CC(=O)Nc1nc2ccc(-c3cnc(C)c(NC(=O)CC4CCCC4)c3)cc2s1] | A | ¹H NMR (400 MHz, DMSO-d6) δ 12.41 (s, 1H), 9.52 (s, 1H), 8.62 (s, 1H), 8.31 (s, 1H), 8.11 (s, 1H), 7.82 (d, J = 8.4 Hz, 1H), 7.72 (d, J = 8.3 Hz, 1H), 2.45 (s, 3H), 2.40 (d, J = 7.2 Hz, 2H), 2.22 (s, 3H), 1.86-1.74 (m, 2H), 1.70-1.47 (m, 4H), 1.31-1.16 (m, 3H). | 407.0 [M − H]⁻ |
| A44 | 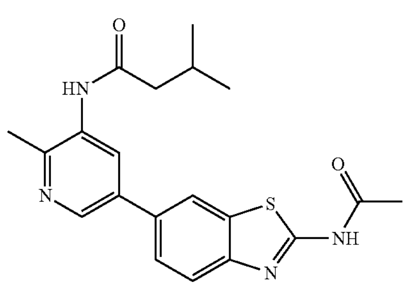 | A | ¹H NMR (400 MHz, DMSO-d6) δ 12.41 (s, 1H), 9.53 (s, 1H), 8.62 (s, 1H), 8.31 (s, 1H), 8.11 (s, 1H), 7.82 (d, J = 8.4 Hz, 1H), 7.72 (d, J = 8.4 Hz, 1H), 2.45 (s, 3H), 2.28 (d, J = 7.2 Hz, 2H), 2.22 (s, 3H), 2.14-2.05 (m, 1H), 0.98 (d, J = 6.4 Hz, 6H). | |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A45 | 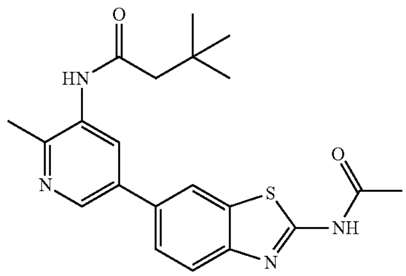 [SMILES: CC(=O)Nc1nc2ccc(-c3cnc(C)c(NC(=O)CC(C)(C)C)c3)cc2s1] | A | ¹H NMR (400 MHz, DMSO-d6) δ 12.41 (s, 1H), 9.48 (s, 1H), 8.62 (s, 1H), 8.31 (s, 1H), 8.11 (s, 1H), 7.82 (d, J = 8.4 Hz, 1H), 7.72 (d, J = 8.4 Hz, 1H), 2.47 (s, 4H), 2.29 (s, 2H), 2.22 (s, 3H), 1.07 (s, 9H). | |
| A46 | 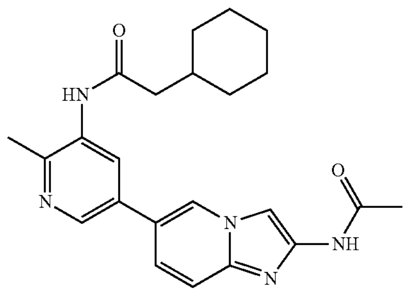 [SMILES: CC(=O)Nc1cn2cc(-c3cnc(C)c(NC(=O)CC4CCCCC4)c3)ccc2n1] | D | ¹H NMR (400 MHz, DMSO-d6) δ 12.41 (s, 1H), 9.51 (s, 1H), 8.62 (s, 1H), 8.31 (s, 1H), 8.12 (s, 1H), 7.82 (d, J = 8.4 Hz, 1H), 7.72 (d, J = 8.4 Hz, 1H), 2.45 (s, 3H), 2.29 (d, J = 6.8 Hz, 2H), 2.22 (s, 3H), 1.84-1.59 (m, 5H), 1.31-1.12 (m, 3H), 1.06-0.92 (m, 2H). | 406.1 |
| A47 | 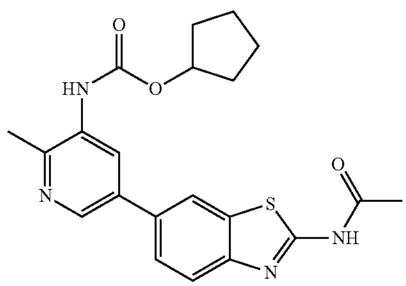 [SMILES: CC(=O)Nc1nc2ccc(-c3cnc(C)c(NC(=O)OC4CCCC4)c3)cc2s1] | A | ¹H NMR (400 MHz, DMSO-d6) δ 12.41 (s, 1H), 9.09 (s, 1H), 8.59 (s, 1H), 8.31 (s, 1H), 8.10 (s, 1H), 7.82 (d, J = 8.4 Hz, 1H), 7.72 (d, J = 8.4 Hz, 1H), 5.19-5.04 (m, 1H), 2.46 (s, 3H), 2.22 (s, 3H), 1.97-1.82 (m, 2H), 1.75-1.67 (m, 4H), 1.63-1.52 (m, 2H). | 411.0 |
| A48 | 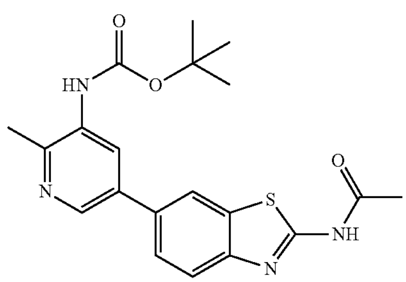 [SMILES: CC(=O)Nc1nc2ccc(-c3cnc(C)c(NC(=O)OC(C)(C)C)c3)cc2s1] | D | ¹H NMR (400 MHz, DMSO-d6) δ 12.40 (s, 1H), 8.87 (s, 1H), 8.57 (s, 1H), 8.31 (s, 1H), 8.06 (s, 1H), 7.82 (d, J = 8.4 Hz, 1H), 7.71 (d, J = 8.4 Hz, 1H), 2.45 (s, 3H), 2.22 (s, 3H), 1.49 (s, 9H). | 399.0 |
| A49 | 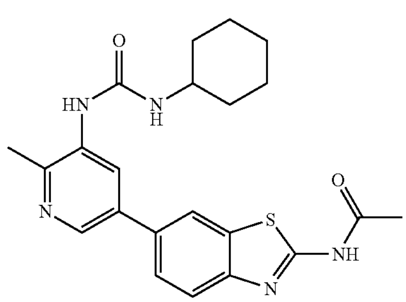 [SMILES: CC(=O)Nc1nc2ccc(-c3cnc(C)c(NC(=O)NC4CCCCC4)c3)cc2s1] | A | ¹H NMR (400 MHz, DMSO-d6) δ 8.60 (s, 1H), 8.37 (s, 1H), 8.17 (s, 1H), 7.81 (s, 1H), 7.74 (d, J = 8.4 Hz, 1H), 7.62 (d, J = 8.4 Hz, 1H), 6.71 (d, J = 7.4 Hz, 1H), 3.51-4.89 (m, 1H), 2.43 (s, 3H), 2.17 (s, 3H), 1.88-1.80 (m, 2H), 1.73-1.63 (m, 2H), 1.56-1.53 (m, 1H), 1.39-1.26 (m, 2H), 1.19 (dd, J = 20.1, 10.1 Hz, 3H). | |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A50 | 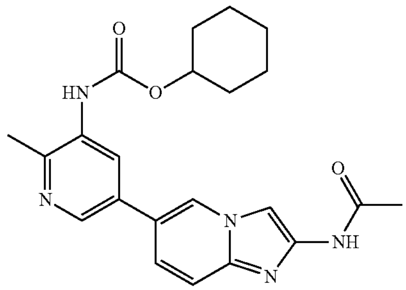 [SMILES: CC(=O)Nc1cn2cc(-c3cnc(C)c(NC(=O)OC4CCCCC4)c3)ccc2n1] | D | ¹H NMR (400 MHz, DMSO-d6) δ 10.73 (s, 1H), 9.15 (s, 1H), 8.96 (s, 1H), 8.55 (s, 1H), 8.13 (s, 1H), 8.07 (s, 1H), 7.52 (s, 2H), 4.70-4.57 (m, 1H), 2.45 (s, 3H), 2.08 (s, 3H), 1.95-1.90 (m, 2H), 1.80-1.66 (m, 2H), 1.57-1.50 (m, 1H), 1.49-1.26 (m, 5H). | 408.3 |
| A51 | 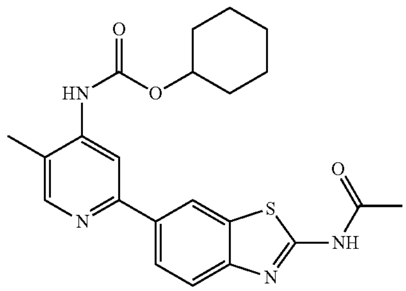 | D | ¹H NMR (400 MHz, DMSO-d6) δ 12.42 (s, 1H), 9.18 (s, 1H), 8.57 (s, 1H), 8.38 (s, 1H), 8.29 (s, 1H), 8.04 (d, J = 8.4 Hz, 1H), 7.80 (d, J = 8.4 Hz, 1H), 4.78-4.60 (m, 1H), 2.26 (s, 3H), 2.22 (s, 3H), 2.00-1.90 (m, 2H), 1.82-1.71 (m, 2H), 1.62-1.16 (m, 6H). | 425.1 |
| A52 | 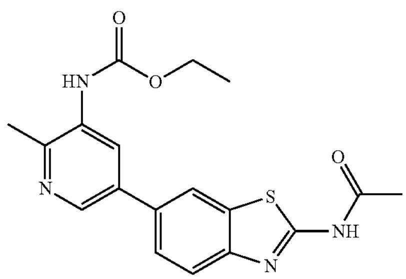 [SMILES: CCOC(=O)Nc1cc(-c2ccc3nc(NC(C)=O)sc3c2)cnc1C] | D | ¹H NMR (400 MHz, DMSO-d6) δ 12.42 (s, 1H), 9.18 (s, 1H), 8.59 (s, 1H), 8.31 (s, 1H), 8.11 (s, 1H), 7.82 (d, J = 8.4 Hz, 1H), 7.72 (d, J = 8.4 Hz, 1H), 4.16 (q, J = 7.0 Hz, 2H), 2.46 (s, 3H), 2.22 (s, 3H), 1.27 (t, J = 7.0 Hz, 3H). | 371.0 |
| A53 | 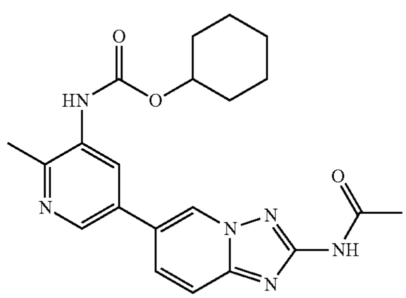 [SMILES: CC(=O)Nc1nc2ccc(-c3cnc(C)c(NC(=O)OC4CCCCC4)c3)cn2n1] | D | ¹H NMR (400 MHz, DMSO-d6) δ 10.83 (s, 1H), 9.28 (s, 1H), 9.17 (s, 1H), 8.65 (s, 1H), 8.15 (s, 1H), 7.95 (d, J = 9.2 Hz, 1H), 7.77 (d, J = 9.2 Hz, 1H), 4.74-4.59 (m, 1H), 2.46 (s, 3H), 2.16 (s, 3H), 1.95-1.90 (m, 2H), 1.80-1.66 (m, 2H), 1.57-1.50 (m, 1H), 1.49-1.26 (m, 5H). | 409.1 |
| A54 | 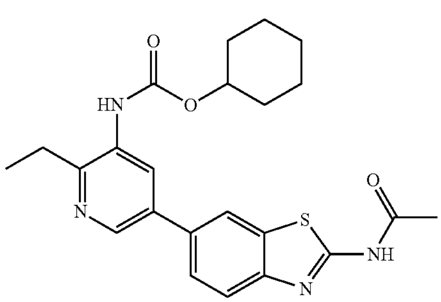 [SMILES: CCc1ncc(-c2ccc3nc(NC(C)=O)sc3c2)cc1NC(=O)OC1CCCCC1] | D | ¹H NMR (400 MHz, DMSO-d6) δ 12.41 (s, 1H), 9.11 (s, 1H), 8.66 (s, 1H), 8.32 (s, 1H), 8.06 (s, 1H), 7.82 (d, J = 8.4 Hz, 1H), 7.73 (d, J = 8.4 Hz, 1H), 4.72-4.55 (m, 1H), 2.81 (q, J = 7.4 Hz, 2H), 2.22 (s, 3H), 1.92-1.89 (m, 2H), 1.72-1.70 (m, 2H), 1.61-1.28 (m, 4H), 1.20 (t, J = 7.4 Hz, 3H). | 439.0 |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A55 | 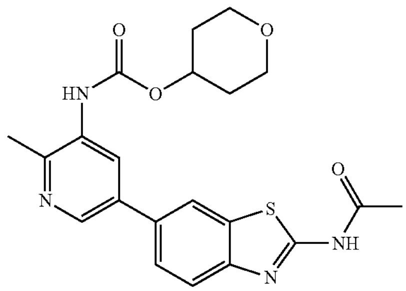 [SMILES: CC(=O)Nc1nc2ccc(-c3cnc(C)c(NC(=O)OC4CCOCC4)c3)cc2s1] | D | ¹H NMR (400 MHz, DMSO-d6) δ 12.41 (s, 1H), 9.21 (s, 1H), 8.60 (s, 1H), 8.31 (s, 1H), 8.10 (s, 1H), 7.82 (d, J = 8.4 Hz, 1H), 7.72 (d, J = 8.4 Hz, 1H), 4.93-4.77 (m, 1H), 3.87-3.83 (m, 2H), 3.46 (t, J = 10.0 Hz, 2H), 2.46 (s, 3H), 2.22 (s, 3H), 2.00-1.90 (d, J = 11.3 Hz, 2H), 1.62 (dd, J = 18.2, 8.9 Hz, 2H). | 427.0 |
| A56 | 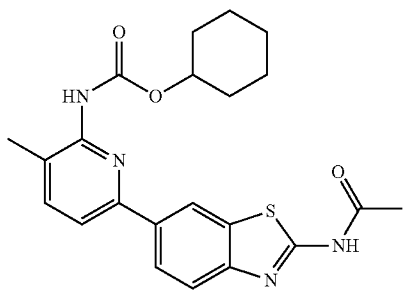 [SMILES: CC(=O)Nc1nc2ccc(-c3ccc(C)c(NC(=O)OC4CCCCC4)n3)cc2s1] | E | ¹H NMR (400 MHz, DMSO-d6) δ 12.42 (s, 1H), 9.41 (s, 1H), 8.63 (s, 1H), 8.14 (d, J = 8.8 Hz, 1H), 7.79 (d, J = 8.4 Hz, 2H), 7.73 (d, J = 8.0 Hz, 1H), 4.65-4.60 (m, 1H), 2.23 (s, 3H), 2.22 (s, 3H), 1.90-1.87 (m, 2H), 1.72-1.70 (m, 2H), 1.53-1.21 (m, 6H). | 425.1 |
| A57 | 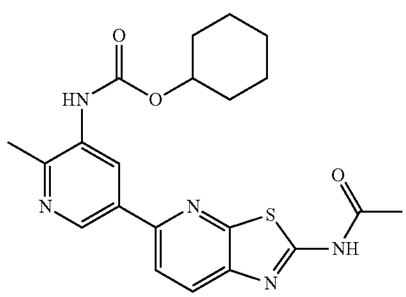 [SMILES: CC(=O)Nc1nc2ccc(-c3cnc(C)c(NC(=O)OC4CCCCC4)c3)nc2s1] | C | ¹H NMR (400 MHz, DMSO-d6) δ 12.54 (s, 1H), 9.13 (s, 1H), 8.94 (s, 1H), 8.50 (s, 1H), 8.18 (d, J = 8.4 Hz, 1H), 8.09 (d, J = 8.4 Hz, 1H), 4.78-4.59 (m, 1H), 2.48 (s, 3H), 2.24 (s, 3H), 1.95-1.87 (m, 2H), 1.79-1.68 (m, 2H), 1.58-1.17 (m, 6H). | 426.1 |
| A58 | 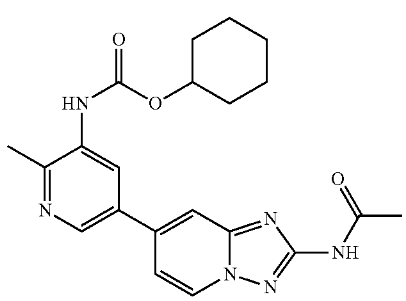 [SMILES: CC(=O)Nc1nc2cc(-c3cnc(C)c(NC(=O)OC4CCCCC4)c3)ccn2n1] | D | ¹H NMR (400 MHz, DMSO-d6) δ 10.82 (s, 1H), 9.19 (s, 1H), 8.92 (d, J = 6.8 Hz, 1H), 8.73 (s, 1H), 8.23 (s, 1H), 8.01 (s, 1H), 7.46 (d, J = 6.8 Hz, 1H), 4.73-4.56 (m, 1H), 2.48 (s, 3H), 2.15 (s, 3H), 1.95-1.90 (m, 2H), 1.81-1.64 (m, 2H), 1.61-1.15 (m, 6H). | 409.2 |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A59 | 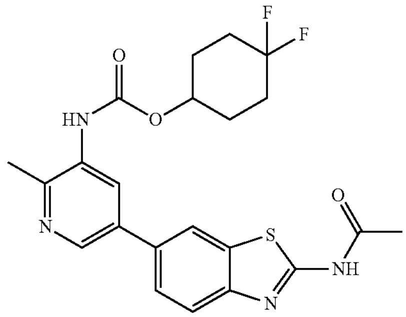 [SMILES: CC(=O)Nc1nc2ccc(-c3cnc(C)c(NC(=O)OC4CCC(F)(F)CC4)c3)cc2s1] | D | ¹H NMR (400 MHz, DMSO-d6) δ 12.42 (s, 1H), 9.20 (s, 1H), 8.60 (s, 1H), 8.31 (s, 1H), 8.13 (s, 1H), 7.82 (d, J = 8.4 Hz, 1H), 7.72 (d, J = 8.6 Hz, 1H), 4.93-4.84 (m, 1H), 2.47 (s, 3H), 2.22 (s, 3H), 2.14-1.88 (m, 6H), 1.85-1.75 (m, 2H). | 461.1 |
| A60 | 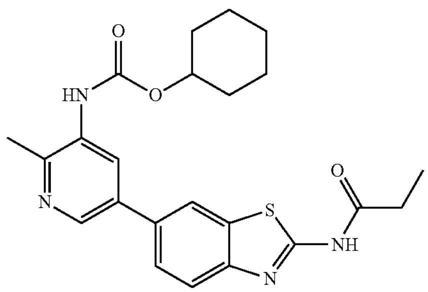 [SMILES: CCC(=O)Nc1nc2ccc(-c3cnc(C)c(NC(=O)OC4CCCCC4)c3)cc2s1] | B | ¹H NMR (400 MHz, DMSO-d6) δ 12.38 (s, 1H), 9.12 (s, 1H), 8.59 (s, 1H), 8.32 (s, 1H), 8.11 (s, 1H), 7.81 (d, J = 8.4 Hz, 1H), 7.72 (d, J = 8.4 Hz, 1H), 4.65 (s, 1H), 2.54 (q, J = 7.4 Hz, 2H), 2.46 (s, 3H), 1.91 (s, 2H), 1.71 (s, 2H), 1.52 (s, 1H), 1.47-1.29 (m, 4H), 1.23 (s, 1H), 1.12 (t, J = 7.4 Hz, 3H). | |
| A61 | 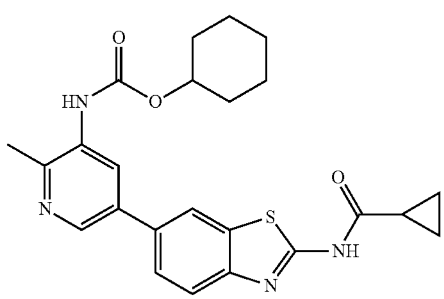 [SMILES: Cc1ncc(-c2ccc3nc(NC(=O)C4CC4)sc3c2)cc1NC(=O)OC1CCCCC1] | D | ¹H NMR (400 MHz, DMSO-d6) δ 12.72 (s, 1H), 9.12 (s, 1H), 8.59 (s, 1H), 8.31 (s, 1H), 8.11 (s, 1H), 7.82 (d, J = 8.4 Hz, 1H), 7.73 (d, J = 8.4 Hz, 1H), 4.65 (s, 1H), 2.46 (s, 3H), 2.04-1.97 (m, 1H), 1.96-1.88 (m, 2H), 1.76-1.67 (m, 2H), 1.58-1.49 (m, 1H), 1.47-1.31 (m, 4H), 1.25-1.20 (m, 1H), 1.02-0.94 (m, 4H). | |
| A62 | 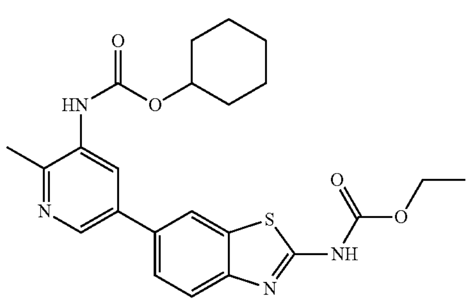 [SMILES: CCOC(=O)Nc1nc2ccc(-c3cnc(C)c(NC(=O)OC4CCCCC4)c3)cc2s1] | D | ¹H NMR (400 MHz, DMSO-d6) δ 12.11 (s, 1H), 9.12 (s, 1H), 8.58 (s, 1H), 8.30 (s, 1H), 8.09 (s, 1H), 7.73 (dd, J = 27.8, 8.1 Hz, 2H), 4.65 (s, 1H), 4.26 (q, J = 7.0 Hz, 2H), 2.45 (s, 3H), 1.91 (s, 2H), 1.72 (s, 2H), 1.52 (s, 1H), 1.49-1.32 (m, 4H), 1.29 (t, J = 7.0 Hz, 3H), 1.24 (s, 1H). | |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A63 | 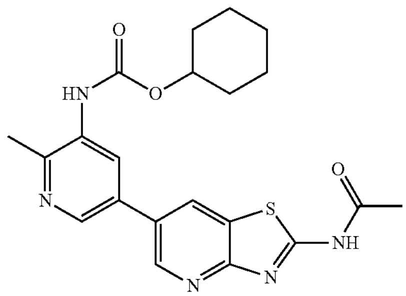 [SMILES: CC(=O)Nc1nc2ncc(-c3cnc(C)c(NC(=O)OC4CCCCC4)c3)cc2s1] | D | ¹H NMR (400 MHz, DMSO-d6) δ 12.69 (s, 1H), 9.16 (s, 1H), 8.83 (s, 1H), 8.76 (s, 1H), 8.62 (s, 1H), 8.14 (s, 1H), 4.71-4.57 (m, 1H), 2.47 (s, 3H), 2.25 (s, 3H), 2.00-1.86 (m, 2H), 1.77-1.67 (m, 2H), 1.60-1.19 (m, 6H). | 426.1 |
| A64 | 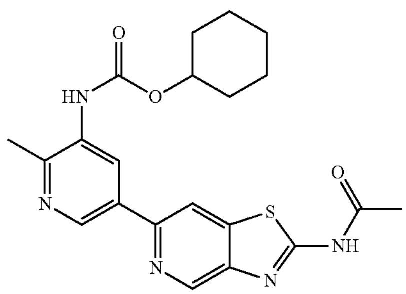 [SMILES: CC(=O)Nc1nc2cnc(-c3cnc(C)c(NC(=O)OC4CCCCC4)c3)cc2s1] | C | ¹H NMR (400 MHz, DMSO-d6) δ 12.62 (s, 1H), 9.12 (s, 1H), 9.06 (s, 1H), 8.92 (s, 1H), 8.68 (s, 1H), 8.49 (s, 1H), 4.69-4.60 (m, 1H), 2.47 (s, 3H), 2.24 (s, 3H), 1.97-1.86 (m, 2H), 1.79-1.67 (m, 2H), 1.60-1.17 (m, 6H). | 426.1 |
| A65 | 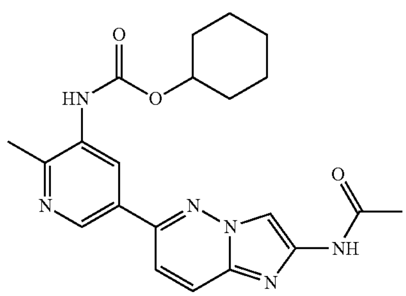 [SMILES: CC(=O)Nc1cn2nc(-c3cnc(C)c(NC(=O)OC4CCCCC4)c3)ccc2n1] | C | ¹H NMR (400 MHz, DMSO-d6) δ 10.95 (s, 1H), 9.21 (s, 1H), 8.88 (s, 1H), 8.45 (s, 1H), 8.31 (s, 1H), 8.09 (d, J = 9.2 Hz, 1H), 7.81 (d, J = 9.2 Hz, 1H), 4.68 (s, 1H), 2.50 (s, 3H), 2.12 (s, 3H), 1.93 (s, 2H), 1.73 (s, 2H), 1.52 (s, 1H), 1.49-1.31 (m, 4H), 1.24 (s, 1H). | |
| A66 | 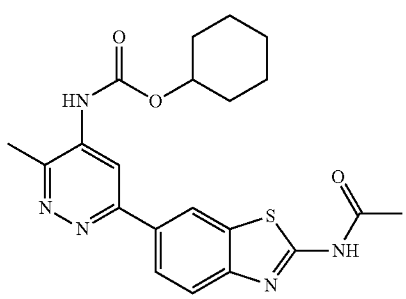 [SMILES: CC(=O)Nc1nc2ccc(-c3cc(NC(=O)OC4CCCCC4)c(C)nn3)cc2s1] | F | ¹H NMR (400 MHz, DMSO-d6) δ 12.47 (s, 1H), 9.48 (s, 1H), 8.65 (s, 1H), 8.47 (s, 1H), 8.08 (d, J = 8.4 Hz, 1H), 7.86 (d, J = 8.4 Hz, 1H), 4.80-4.68 (m, 1H), 2.65 (s, 3H), 2.23 (s, 3H), 2.02-1.91 (m, 2H), 1.81-1.69 (m, 2H), 1.61-1.24 (m, 6H). | |
| A67 | 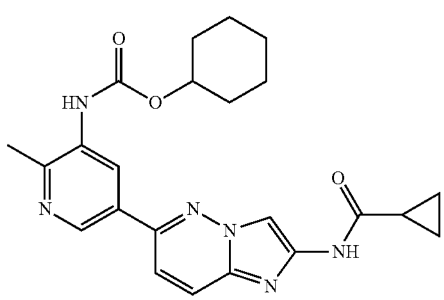 [SMILES: Cc1ncc(-c2ccc3nc(NC(=O)C4CC4)cn3n2)cc1NC(=O)OC1CCCCC1] | C | ¹H NMR (400 MHz, DMSO-d6) δ 11.23 (s, 1H), 9.20 (s, 1H), 8.87 (s, 1H), 8.43 (s, 1H), 8.28 (s, 1H), 8.09 (d, J = 9.4 Hz, 1H), 7.80 (d, J = 9.4 Hz, 1H), 4.67 (s, 1H), 2.50 (s, 3H), 2.01-1.89 (m, 3H), 1.72 (s, 2H), 1.51 (s, 1H), 1.48-1.32 (m, 4H), 1.23 (s, 1H), 0.84 (d, J = 7.6 Hz, 4H). | |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A68 | 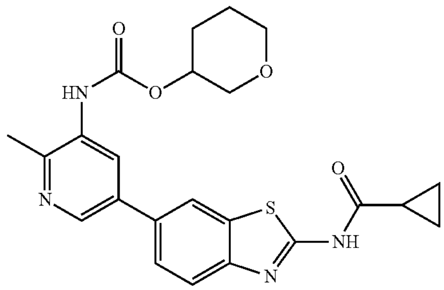 [SMILES: Cc1ncc(-c2ccc3nc(NC(=O)C4CC4)sc3c2)cc1NC(=O)OC1CCCOC1] | D | ¹H NMR (400 MHz, DMSO-d6) δ 12.72 (s, 1H), 9.26 (s, 1H), 8.61 (s, 1H), 8.32 (s, 1H), 8.11 (s, 1H), 7.82 (d, J = 8.4 Hz, 1H), 7.74 (d, J = 8.4 Hz, 1H), 4.75-4.60 (m, 1H), 3.77 (d, J = 10.8 Hz, 1H), 3.68-3.48 (m, 3H), 2.47 (s, 3H), 2.06-1.90 (m, 2H), 1.83-1.77 (m, 2H), 1.58-1.47 (m, 1H), 1.00-0.96 (m, 4H). | 453.1 |
| A69 | 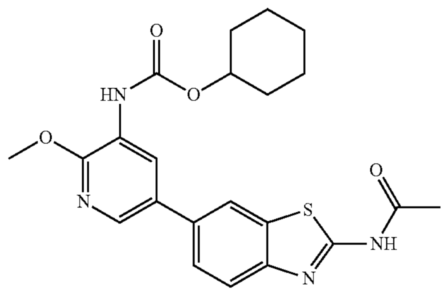 [SMILES: COc1ncc(-c2ccc3nc(NC(C)=O)sc3c2)cc1NC(=O)OC1CCCCC1] | D | ¹H NMR (400 MHz, DMSO-d6) δ 12.40 (s, 1H), 8.75 (s, 1H), 8.35 (s, 1H), 8.24 (d, J = 6.6 Hz, 2H), 7.81 (d, J = 8.4 Hz, 1H), 7.67 (d, J = 8.4 Hz, 1H), 4.75-4.61 (m, 1H), 3.95 (s, 3H), 2.22 (s, 3H), 1.95-1.83 (m, 2H), 1.77-1.68 (m, 2H), 1.58-1.19 (m, 6H). | 441.1 |
| A70 | 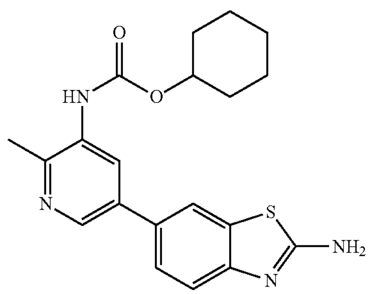 [SMILES: Cc1ncc(-c2ccc3nc(N)sc3c2)cc1NC(=O)OC1CCCCC1] | B | ¹H NMR (400 MHz, DMSO-d6) δ 9.09 (s, 1H), 8.52 (s, 1H), 8.02 (s, 1H), 8.00 (s, 1H), 7.60 (s, 2H), 7.51 (d, J = 8.4 Hz, 1H), 7.40 (d, J = 8.4 Hz, 1H), 4.74-4.51 (m, 1H), 2.43 (s, 3H), 1.95-1.87 (m, 2H), 1.78-1.65 (m, 2H), 1.58-1.21 (m, 6H). | 383.1 |
| A71 | 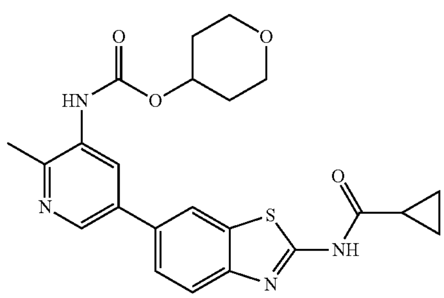 | D | ¹H NMR (400 MHz, DMSO-d6) δ 12.73 (s, 1H), 9.23 (s, 1H), 8.60 (s, 1H), 8.32 (s, 1H), 8.11 (s, 1H), 7.82 (d, J = 8.4 Hz, 1H), 7.73 (d, J = 8.4 Hz, 1H), 4.92-4.77 (m, 1H), 3.91-3.84 (m, 2H), 3.46 (t, J = 10.8 Hz, 2H), 2.46 (s, 3H), 2.05-1.89 (m, 3H), 1.63-1.54 (m, 2H), 1.04-0.89 (m, 4H). | 453.1 |
| A72 | 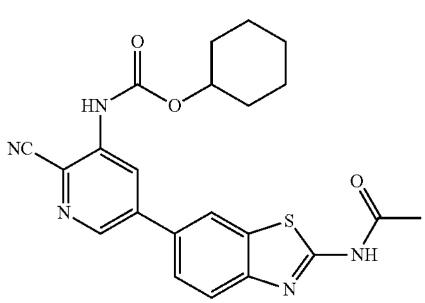 [SMILES: CC(=O)Nc1nc2ccc(-c3cnc(C#N)c(NC(=O)OC4CCCCC4)c3)cc2s1] | D | ¹H NMR (400 MHz, DMSO-d6) δ 12.50 (s, 1H), 10.05 (s, 1H), 8.90 (s, 1H), 8.46 (s, 1H), 8.31 (s, 1H), 7.97-7.80 (m, 2H), 4.69 (s, 1H), 2.22 (s, 3H), 1.91 (s, 2H), 1.71 (s, 2H), 1.46 (dd, J = 20.7, 9.8 Hz, 3H), 1.42-1.30 (m, 2H), 1.25 (s, 1H). | |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A73 | 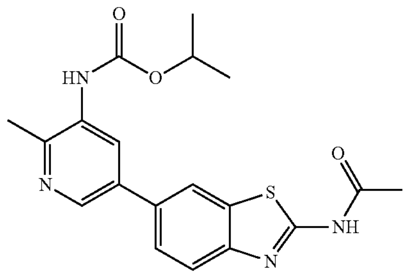 [SMILES: CC(=O)Nc1nc2ccc(-c3cnc(C)c(NC(=O)OC(C)C)c3)cc2s1] | D | ¹H NMR (400 MHz, DMSO-d6) δ 12.41 (s, 1H), 9.10 (s, 1H), 8.59 (s, 1H), 8.31 (s, 1H), 8.10 (s, 1H), 7.82 (d, J = 8.4 Hz, 1H), 7.72 (d, J = 8.4 Hz, 1H), 4.99-4.81 (m, 1H), 2.46 (s, 3H), 2.22 (s, 3H), 1.28 (d, J = 6.0 Hz, 6H). | 385.1 |
| A74 | 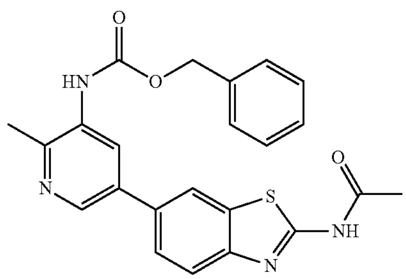 [SMILES: CC(=O)Nc1nc2ccc(-c3cnc(C)c(NC(=O)OCc4ccccc4)c3)cc2s1] | D | ¹H NMR (400 MHz, DMSO-d6) δ 12.40 (s, 1H), 9.33 (s, 1H), 8.60 (s, 1H), 8.30 (s, 1H), 8.12 (s, 1H), 7.82 (d, J = 8.4 Hz, 1H), 7.71 (d, J = 8.4 Hz, 1H), 7.47-7.33 (m, 5H), 5.19 (s, 2H), 2.46 (s, 3H), 2.22 (s, 3H). | 433.1 |
| A75 | 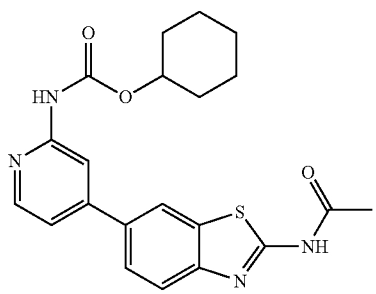 [SMILES: CC(=O)Nc1nc2ccc(-c3ccnc(NC(=O)OC4CCCCC4)c3)cc2s1] | D | ¹H NMR (400 MHz, DMSO-d6) δ 12.44 (s, 1H), 10.08 (s, 1H), 8.38 (s, 1H), 8.32 (d, J = 4.8 Hz, 1H), 8.18 (s, 1H), 7.85 (d, J = 8.4 Hz, 1H), 7.77 (d, J = 8.4 Hz, 1H), 7.40 (d, J = 4.7 Hz, 1H), 4.77-4.60 (m, 1H), 2.22 (s, 3H), 1.92-1.87 (m, 2H), 1.82-1.64 (m, 2H), 1.58-1.20 (m, 6H). | 411.1 |
| A76 | 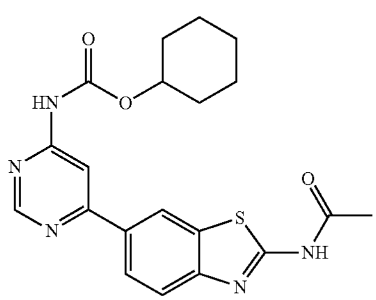 [SMILES: CC(=O)Nc1nc2ccc(-c3cc(NC(=O)OC4CCCCC4)ncn3)cc2s1] | D | ¹H NMR (400 MHz, DMSO-d6) δ 12.50 (s, 1H), 10.68 (s, 1H), 8.86 (s, 1H), 8.73 (s, 1H), 8.39 (s, 1H), 8.13 (d, J = 8.4 Hz, 1H), 7.86 (d, J = 8.4 Hz, 1H), 4.80-4.68 (m, 1H), 2.23 (s, 3H), 2.00-1.84 (m, 2H), 1.80-1.68 (m, 2H), 1.59-1.22 (m, 6H). | 412.1 |

TABLE 1-continued

Selected compounds synthesized by Methods A—E

| Compd NO. | Structure | Method | $^1$H NMR | ESI-MS (m/z): [M + 1]$^+$ |
|---|---|---|---|---|
| A77 | 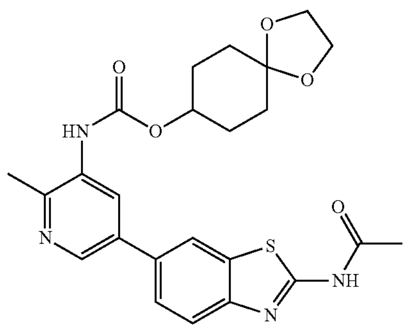 [SMILES: CC(=O)Nc1nc2ccc(-c3cnc(C)c(NC(=O)OC4CCC5(CC4)OCCO5)c3)cc2s1] | D | $^1$H NMR (400 MHz, DMSO-d6) δ 12.42 (s, 1H), 9.16 (s, 1H), 8.59 (s, 1H), 8.31 (s, 1H), 8.10 (s, 1H), 7.82 (d, J = 8.4 Hz, 1H), 7.72 (d, J = 8.4 Hz, 1H), 4.83-4.73 (m, 1H), 3.89-3.87 (m, 4H), 2.46 (s, 4H), 2.22 (s, 3H), 1.94-1.83 (m, 2H), 1.80-1.67 (m, 4H), 1.66-1.55 (m, 2H). | 483.2 |
| A78 | 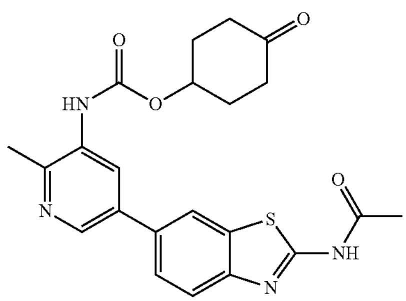 [SMILES: CC(=O)Nc1nc2ccc(-c3cnc(C)c(NC(=O)OC4CCC(=O)CC4)c3)cc2s1] | D | $^1$H NMR (400 MHz, DMSO-d6) δ 12.42 (s, 1H), 9.23 (s, 1H), 8.61 (s, 1H), 8.32 (s, 1H), 8.14 (s, 1H), 7.82 (d, J = 8.4 Hz, 1H), 7.73 (d, J = 8.4 Hz, 1H), 5.14-5.04 (m, 1H), 2.48 (s, 3H), 2.41 (t, J = 6.0 Hz, 4H), 2.22 (s, 3H), 2.19-2.08 (m, 2H), 2.07-1.95 (m, 2H). | 439.1 |
| A79 | 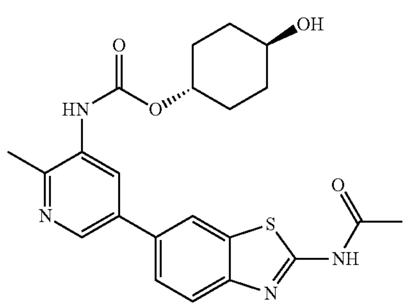 [SMILES: CC(=O)Nc1nc2ccc(-c3cnc(C)c(NC(=O)O[C@H]4CC[C@H](O)CC4)c3)cc2s1] | D | $^1$H NMR (400 MHz, DMSO-d6) δ 12.42 (s, 1H), 9.13 (s, 1H), 8.59 (s, 1H), 8.31 (s, 1H), 8.09 (s, 1H), 7.82 (d, J = 8.4 Hz, 1H), 7.72 (d, J = 8.4 Hz, 1H), 4.69-4.53 (m, 2H), 3.55-3.44 (br s, 1H), 2.45 (s, 3H), 2.22 (s, 3H), 2.04-1.96 (m, 2H), 1.89-1.79 (m, 2H), 1.48-1.39 (m, 2H), 1.37-1.22 (m, 2H). | 440.8 |
| A80 | 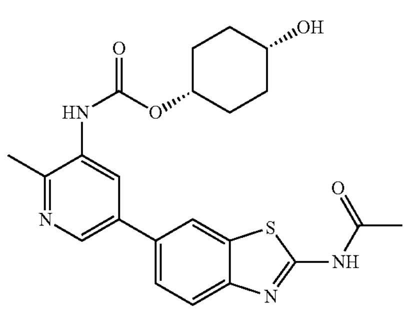 | D | $^1$H NMR (400 MHz, DMSO-d6) δ 12.41 (s, 1H), 9.11 (s, 1H), 8.59 (s, 1H), 8.32 (s, 1H), 8.10 (s, 1H), 7.82 (d, J = 8.4 Hz, 1H), 7.73 (d, J = 8.4 Hz, 1H), 4.76-4.67 (m, 1H), 4.54 (br s, 1H), 3.70-3.56 (m, 1H), 2.46 (s, 3H), 2.22 (s, 3H), 1.83-1.81 (m, 2H), 1.71-1.49 (m, 6H). | 440.8 |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A81 | 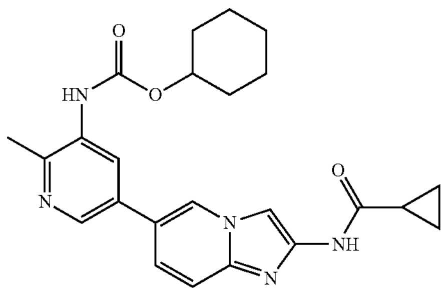 [SMILES: Cc1ncc(-c2ccc3nc(NC(=O)C4CC4)cn3c2)cc1NC(=O)OC1CCCCC1] | C | ¹H NMR (400 MHz, DMSO-d6) δ 10.99 (s, 1H), 9.12 (s, 1H), 8.95 (s, 1H), 8.56 (s, 1H), 8.10-8.02 (m, 2H), 7.52 (s, 2H), 4.70-4.57 (m, 1H), 2.45 (s, 3H), 2.00-1.89 (m, 3H), 1.79-1.68 (m, 2H), 1.58-1.20 (m, 6H), 0.86-0.75 (m, 4H). | |
| A82 | 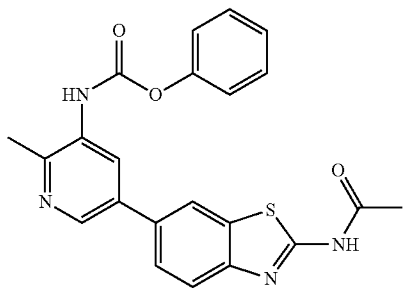 [SMILES: CC(=O)Nc1nc2ccc(-c3cnc(C)c(NC(=O)Oc4ccccc4)c3)cc2s1] | A | ¹H NMR (400 MHz, DMSO-d6) δ 12.42 (s, 1H), 9.84 (s, 1H), 8.66 (s, 1H), 8.34 (s, 1H), 8.20 (s, 1H), 7.82 (d, J = 8.4 Hz, 1H), 7.74 (d, J = 8.4 Hz, 1H), 7.46-7.42 (m, 2H), 7.30-7.24 (m, 3H), 2.55 (s, 3H), 2.21 (s, 3H). | |
| A83 | 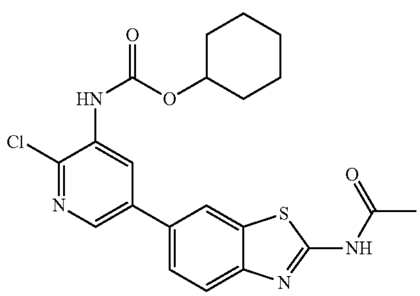 [SMILES: CC(=O)Nc1nc2ccc(-c3cnc(Cl)c(NC(=O)OC4CCCCC4)c3)cc2s1] | D | ¹H NMR (400 MHz, DMSO-d6) δ 12.46 (s, 1H), 9.31 (s, 1H), 8.56 (s, 1H), 8.37 (s, 2H), 7.84 (d, J = 8.0 Hz, 1H), 7.77 (d, J = 8.0 Hz, 1H), 4.74-4.62 (m, 1H), 2.22 (s, 3H), 1.95-1.86 (m, 2H), 1.79-1.66 (m, 2H), 1.53-1.27 (m, 6H). | |
| A84 | 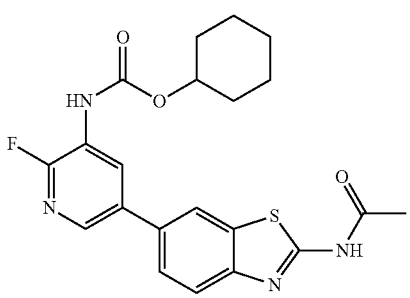 [SMILES: CC(=O)Nc1nc2ccc(-c3cnc(F)c(NC(=O)OC4CCCCC4)c3)cc2s1] | D | ¹H NMR (400 MHz, DMSO-d6) δ 12.44 (s, 1H), 9.67 (s, 1H), 8.51 (d, J = 8.4 Hz, 1H), 8.31 (s, 1H), 8.25 (s, 1H), 7.83 (d, J = 8.4 Hz, 1H), 7.71 (d, J = 8.4 Hz, 1H), 4.74-4.62 (m, 1H), 2.22 (s, 3H), 1.96-1.83 (m, 2H), 1.79-1.65 (m, 2H), 1.58-1.22 (m, 6H). | |
| A85 | 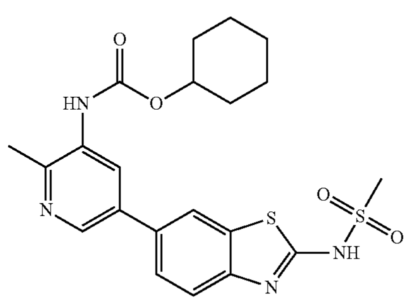 [SMILES: Cc1ncc(-c2ccc3nc(NS(C)(=O)=O)sc3c2)cc1NC(=O)OC1CCCCC1] | D | ¹H NMR (400 MHz, DMSO-d6) δ 13.08 (s, 1H), 9.13 (s, 1H), 8.53 (s, 1H), 8.14 (s, 1H), 8.06 (s, 1H), 7.69 (d, J = 8.4 Hz, 1H), 7.40 (d, J = 8.4 Hz, 1H), 4.64 (s, 1H), 3.02 (s, 3H), 2.45 (s, 3H), 1.90 (s, 2H), 1.71 (s, 2H), 1.52 (s, 1H), 1.48-1.29 (m, 4H), 1.23 (s, 1H). | |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A86 | 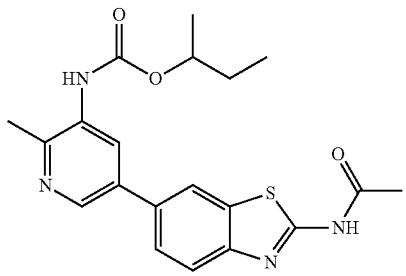 [SMILES: CCC(C)OC(=O)Nc1cc(-c2ccc3nc(NC(C)=O)sc3c2)cnc1C] | D | ¹H NMR (400 MHz, DMSO-d6) δ 12.42 (s, 1H), 9.12 (s, 1H), 8.59 (s, 1H), 8.32 (s, 1H), 8.10 (s, 1H), 7.82 (d, J = 8.4 Hz, 1H), 7.72 (d, J = 8.5 Hz, 1H), 4.77-4.71 (m, 1H), 2.46 (s, 3H), 2.22 (s, 3H), 1.68-1.53 (m, 2H), 1.25 (d, J = 6.0 Hz, 3H), 0.92 (t, J = 7.4 Hz, 3H). | 398.8 |
| A87 | 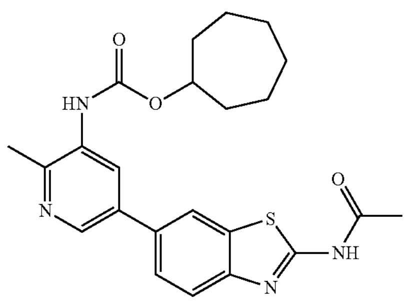 [SMILES: CC(=O)Nc1nc2ccc(-c3cnc(C)c(NC(=O)OC4CCCCCC4)c3)cc2s1] | D | ¹H NMR (400 MHz, DMSO-d6) δ 12.41 (s, 1H), 9.09 (s, 1H), 8.58 (s, 1H), 8.31 (s, 1H), 8.10 (s, 1H), 7.82 (d, J = 8.4 Hz, 1H), 7.72 (d, J = 8.4 Hz, 1H), 4.90-4.75 (m, 1H), 2.45 (s, 3H), 2.22 (s, 3H), 2.02-1.90 (m, 2H), 1.73-1.65 (m, 4H), 1.62-1.50 (m, 4H), 1.50-1.37 (m, 2H). | 438.8 |
| A88 | 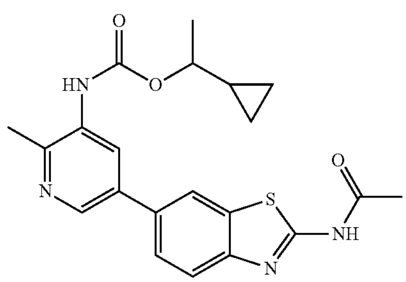 [SMILES: CC(=O)Nc1nc2ccc(-c3cnc(C)c(NC(=O)OC(C)C4CC4)c3)cc2s1] | D | ¹H NMR (400 MHz, DMSO-d6) δ 12.42 (s, 1H), 9.15 (s, 1H), 8.59 (s, 1H), 8.31 (s, 1H), 8.09 (s, 1H), 7.82 (d, J = 8.4 Hz, 1H), 7.72 (d, J = 8.4 Hz, 1H), 4.35-4.22 (m, 1H), 2.46 (s, 3H), 2.22 (s, 3H), 1.32 (d, J = 6.4 Hz, 3H), 1.15-0.99 (m, 1H), 0.59-0.46 (m, 2H), 0.46-0.37 (m, 1H), 0.37-0.28 (m, 1H). | 410.8 |
| A89 | 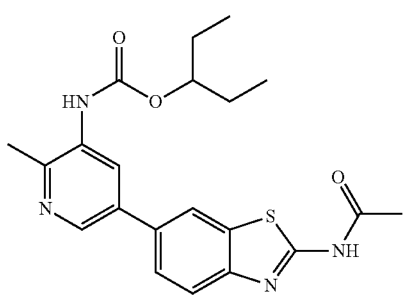 [SMILES: CCC(CC)OC(=O)Nc1cc(-c2ccc3nc(NC(C)=O)sc3c2)cnc1C] | D | ¹H NMR (400 MHz, DMSO-d6) δ 12.41 (s, 1H), 9.13 (s, 1H), 8.59 (s, 1H), 8.32 (s, 1H), 8.08 (s, 1H), 7.82 (d, J = 8.4 Hz, 1H), 7.72 (d, J = 8.4 Hz, 1H), 4.70-4.58 (m, 1H), 2.46 (s, 3H), 2.22 (s, 3H), 1.72-1.50 (m, 4H), 0.92 (t, J = 6.8 Hz, 6H). | 412.8 |
| A90 | 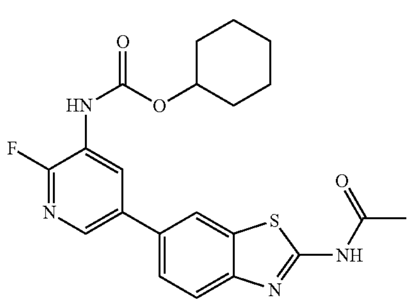 [SMILES: CC(=O)Nc1nc2ccc(-c3cnc(F)c(NC(=O)OC4CCCCC4)c3)cc2s1] | D | ¹H NMR (400 MHz, DMSO-d6) δ 12.44 (s, 1H), 10.06 (s, 1H), 8.54 (s, 2H), 8.51 (d, J = 5.6 Hz, 1H), 8.00 (d, J = 8.4 Hz, 1H), 7.81 (d, J = 8.4 Hz, 1H), 4.79-4.65 (m, 1H), 2.22 (s, 3H), 2.00-1.84 (m, 2H), 1.80-1.68 (m, 2H), 1.58-1.24 (m, 6H). | |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A91 | 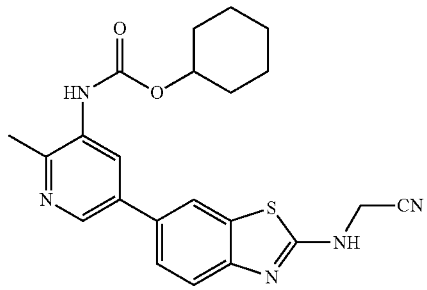 [SMILES: Cc1ncc(-c2ccc3nc(NCC#N)sc3c2)cc1NC(=O)OC1CCCCC1] | D | ¹H NMR (400 MHz, DMSO-d6) δ 9.09 (s, 1H), 8.71 (s, 1H), 8.54 (s, 1H), 8.11 (s, 1H), 8.05 (s, 1H), 7.60 (s, 2H), 4.63 (s, 1H), 4.53 (s, 2H), 2.44 (s, 3H), 1.90 (s, 2H), 1.71 (s, 2H), 1.51 (s, 1H), 1.45-1.31 (m, 4H), 1.23 (s, 1H). | |
| A92 | 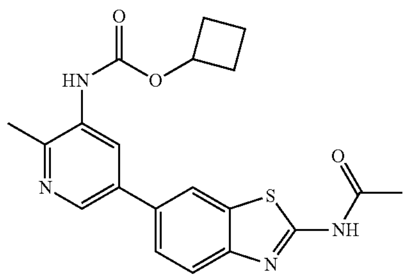 | D | ¹H NMR (400 MHz, DMSO-d6) δ 12.41 (s, 1H), 9.19 (s, 1H), 8.59 (s, 1H), 8.31 (s, 1H), 8.10 (s, 1H), 7.82 (d, J = 8.4 Hz, 1H), 7.72 (d, J = 8.4 Hz, 1H), 5.03-4.89 (m, 1H), 2.46 (s, 3H), 2.36-2.27 (m, 2H), 2.22 (s, 3H), 2.15-2.03 (m, 2H), 1.83-1.70 (m, 1H), 1.67-1.53 (m, 1H). | 396.8 |
| A93 | 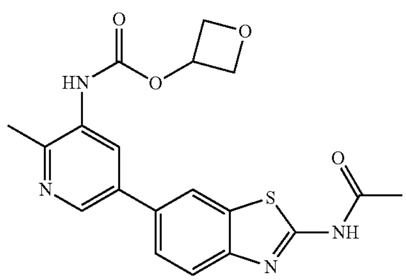 [SMILES: CC(=O)Nc1nc2ccc(-c3cnc(C)c(NC(=O)OC4COC4)c3)cc2s1] | D | ¹H NMR (400 MHz, DMSO-d6) δ 12.41 (s, 1H), 9.48 (s, 1H), 8.62 (s, 1H), 8.31 (s, 1H), 8.10 (s, 1H), 7.82 (d, J = 8.4 Hz, 1H), 7.72 (d, J = 8.4 Hz, 1H), 5.49-5.39 (m, 1H), 4.83 (t, J = 6.8 Hz, 2H), 4.65-4.53 (m, 2H), 2.48 (s, 3H), 2.22 (s, 3H). | 398.8 |
| A94 | 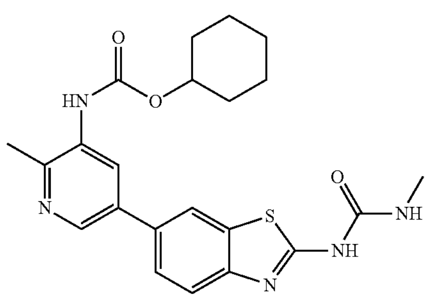 | D | ¹H NMR (400 MHz, DMSO-d6) δ 10.89 (s, 1H), 9.11 (s, 1H), 8.57 (s, 1H), 8.22 (s, 1H), 8.08 (s, 1H), 7.69 (d, J = 8.0 Hz, 1H), 7.65 (d, J = 8.0 Hz, 1H), 6.65 (s, 1H), 4.65 (s, 1H), 2.73 (d, J = 4.0 Hz, 3H), 2.45 (s, 3H), 1.91 (s, 2H), 1.73 (s, 2H), 1.52 (s, 1H), 1.49-1.31 (m, 4H), 1.24 (s, 1H). | |
| A95 | 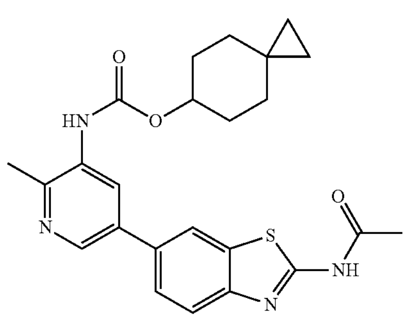 [SMILES: CC(=O)Nc1nc2ccc(-c3cnc(C)c(NC(=O)OC4CCC5(CC4)CC5)c3)cc2s1] | D | ¹H NMR (400 MHz, DMSO-d6) δ 12.41 (s, 1H), 9.13 (s, 1H), 8.59 (s, 1H), 8.31 (s, 1H), 8.11 (s, 1H), 7.82 (d, J = 8.4 Hz, 1H), 7.72 (d, J = 8.4 Hz, 1H), 4.81-4.71 (m, 1H), 2.46 (s, 3H), 2.22 (s, 3H), 1.96-1.84 (m, 2H), 1.68-1.45 (m, 4H), 1.30-1.18 (m, 2H), 0.36-0.18 (m, 4H). | 450.8 |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A96 | 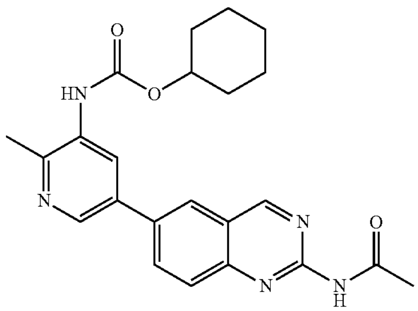 [SMILES: CC(=O)Nc1ncc2cc(-c3cnc(C)c(NC(=O)OC4CCCCC4)c3)ccc2n1] | D | ¹H NMR (400 MHz, DMSO-d6) δ 10.77 (s, 1H), 9.55 (s, 1H), 9.19 (s, 1H), 8.70 (s, 1H), 8.40 (s, 1H), 8.28 (d, J = 8.8 Hz, 1H), 8.23 (s, 1H), 7.90 (d, J = 8.8 Hz, 1H), 4.70-4.60 (m, 1H), 2.50 (s, 3H), 2.29 (s, 3H), 1.98-1.90 (m, 2H), 1.79-1.70 (m, 2H), 1.57-1.24 (m, 6H). | |
| A97 | 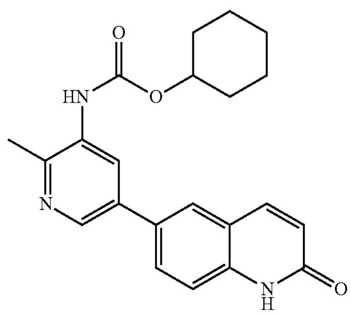 [SMILES: Cc1ncc(-c2ccc3[nH]c(=O)ccc3c2)cc1NC(=O)OC1CCCCC1] | D | ¹H NMR (400 MHz, DMSO-d6) δ 11.85 (s, 1H), 9.12 (s, 1H), 8.57 (s, 1H), 8.01 (dd, J = 25.4, 17.9 Hz, 3H), 7.83 (d, J = 8.6 Hz, 1H), 7.40 (d, J = 8.6 Hz, 1H), 6.55 (d, J = 9.6 Hz, 1H), 4.64 (s, 1H), 2.45 (s, 3H), 1.90 (s, 2H), 1.71 (s, 2H), 1.57-1.11 (m, 7H). | |
| A98 | 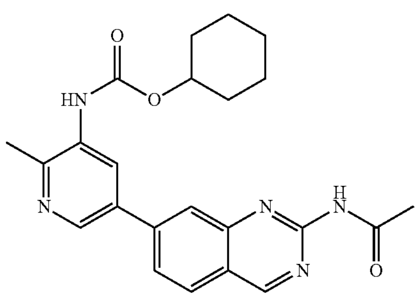 [SMILES: CC(=O)Nc1ncc2ccc(-c3cnc(C)c(NC(=O)OC4CCCCC4)c3)cc2n1] | D | ¹H NMR (400 MHz, DMSO-d6) δ 10.76 (s, 1H), 9.55 (s, 1H), 9.19 (s, 1H), 8.69 (s, 1H), 8.40 (s, 1H), 830-8.16 (m, 2H), 7.89 (d, J = 8.8 Hz, 1H), 4.66 (s, 1H), 2.54 (s, 2H), 2.29 (s, 3H), 1.92 (s, 3H), 1.72 (s, 3H), 1.38 (ddd, J = 53.6, 38.2, 29.1 Hz, 9H). | |
| A99 | 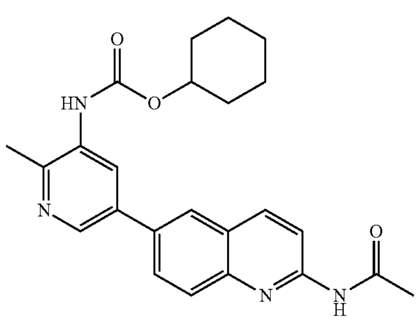 [SMILES: CC(=O)Nc1ccc2cc(-c3cnc(C)c(NC(=O)OC4CCCCC4)c3)ccc2n1] | C | ¹H NMR (400 MHz, DMSO-d6) δ 10.88 (s, 1H), 9.16 (s, 1H), 8.67 (s, 1H), 8.41 (d, J = 8.6 Hz, 1H), 8.34 (s, 1H), 8.21 (d, J = 17.2 Hz, 2H), 8.03 (d, J = 8.6 Hz, 1H), 7.88 (d, J = 8.6 Hz, 1H), 4.65 (s, 1H), 2.45 (m, 3H), 2.16 (s, 3H), 1.91 (s, 2H), 1.72 (s, 2H), 1.56 (m, 8H) | |

TABLE 1-continued

Selected compounds synthesized by Methods A—E

| Compd NO. | Structure | Method | ¹H NMR | ESI-MS (m/z): [M + 1]⁺ |
|---|---|---|---|---|
| A100 | 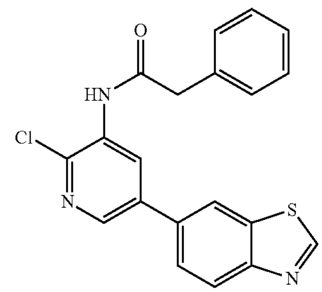 [SMILES: O=C(Cc1ccccc1)Nc1cc(-c2ccc3ncsc3c2)cnc1Cl] | D | ¹H NMR (400 MHz, CDCl₃) δ 9.08 (d, J = 2.0 Hz, 1H), 9.06 (s, 1H), 8.37 (d, J = 2.0 Hz, 1H), 8.22 (d, J = 8.4 Hz, 1H), 8.18 (s, 1H), 7.74 (d, J = 8.4 Hz, 2H), 7.51-7.44 (m, 2H), 7.42-7.38 (m, 3H), 3.86 (s, 2H). | 379.9 |
| A101 | 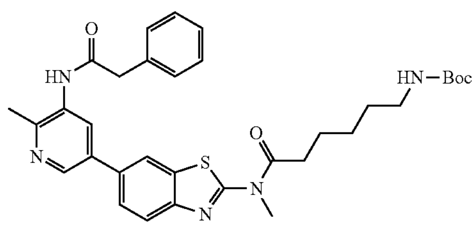 [SMILES: Cc1ncc(-c2ccc3nc(N(C)C(=O)CCCCCNC(=O)OC(C)(C)C)sc3c2)cc1NC(=O)Cc1ccccc1] | D | ¹H NMR (400 MHz, CDCl₃) δ 8.63 (s, 1H), 8.52 (s, 1H), 7.99 (s, 1H), 7.88 (d, J = 8.4 Hz, 1H), 7.64 (d, J = 8.4 Hz, 1H), 7.51-7.44 (m, 2H), 7.45-7.37 (m, 3H), 7.00 (s, 1H), 4.58 (br s, 1H), 3.85 (s, 2H), 3.83 (s, 3H), 3.16 (d, J = 5.8 Hz, 2H), 2.71 (t, J = 7.0 Hz, 2H), 2.18 (s, 3H), 1.84-1.77 (m, 2H), 1.59-1.53 (m, 4H), 1.45 (s, 9H). | |
| A102 | See Table 1A | D | ¹H NMR (400 MHz, DMSO-d6) δ 9.81 (s, 1H), 8.64 (s, 1H), 8.30 (s, 1H), 8.16 (s, 1H), 7.87 (d, J = 7.6 Hz, 1H), 7.73 (s, 3H), 7.38-7.35 (m, 4H), 7.27 (s, 1H), 6.43 (s, 1H), 6.36 (s, 1H), 4.28 (s, 1H), 4.10 (s, 1H), 3.75 (s, 6H), 3.10-2.97 (m, 4H), 2.78 (s, 3H), 2.57 (s, 1H), 2.44 (s, 3H), 2.08-1.96 (m, 4H), 1.77-1.10 (m, 18H). | 841.7 |
| A103 | 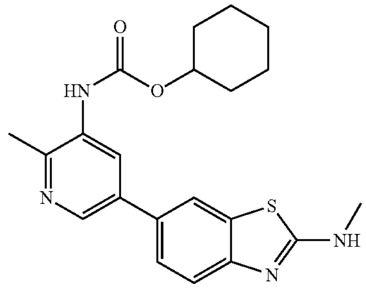 | D | ¹H NMR (400 MHz, DMSO) δ 9.08 (s, 1H), 8.53 (s, 1H), 8.06 (d, J = 4.3 Hz, 1H), 8.02 (d, J = 5.0 Hz, 2H), 7.52 (d. J = 8.5 Hz, 1H), 7.46 (d, J = 8.2 Hz, 1H), 4.64 (s, 1H), 2.96 (d, J = 4.3 Hz, 3H), 2.44 (s, 3H), 2.09 (s. 1H), 1.91 (s, 2H), 1.72 (s, 2H), 1.56-1.50 (m, 1H), 1.47-1.31 (m, 4H), 1.26-1.22 (m, 1H). | |
| A104 | 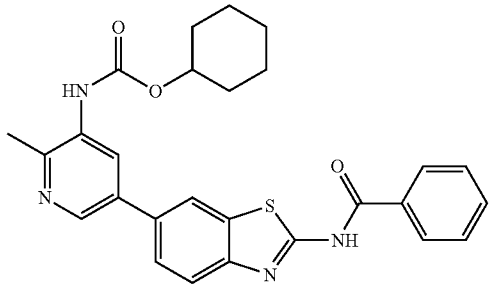 [SMILES: Cc1ncc(-c2ccc3nc(NC(=O)c4ccccc4)sc3c2)cc1NC(=O)OC1CCCCC1] | C | ¹H NMR (400 MHz, DMSO) δ 12.97 (s, 1H), 9.14 (s, 1H), 8.62 (s, 1H), 8.38 (s, 1H), 8.24-8.03 (m, 3H), 7.88 (d. J = 8.3 Hz, 1H), 7.77 (d, J = 8.3 Hz, 1H), 7.68 (t, J = 7.1 Hz, 1H), 7.58 (t, J = 7.5 Hz, 2H), 4.65 (s. 1H), 2.47 (s, 3H), 1.91 (s, 2H), 1.72 (s, 2H), 1.52 (s, 1H), 1.41 (dt, J = 24.6, 11.9 Hz, 4H), 1.23 (s, 1H). | |

TABLE 1A

Structures of selected compounds.

| Compd NO. | structure |
|---|---|
| A8 | 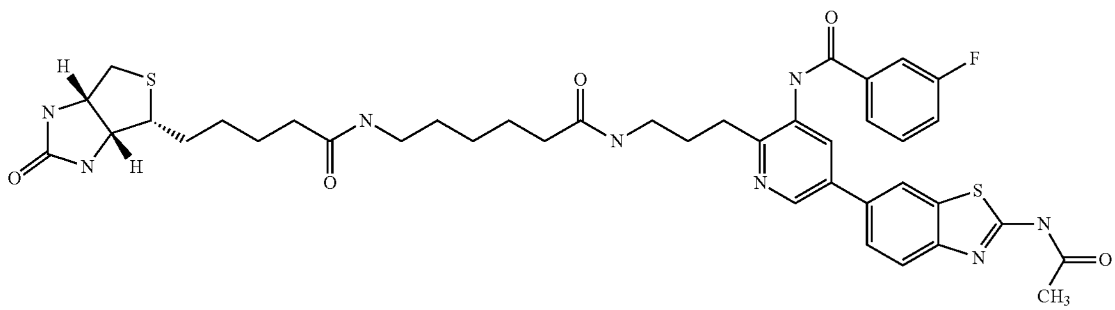 [SMILES: CC(=O)Nc1nc2ccc(-c3cnc(CCCNC(=O)CCCCCNC(=O)CCCC[C@H]4SC[C@H]5NC(=O)N[C@H]54)c(NC(=O)c4cccc(F)c4)c3)cc2s1] |
| A9 | 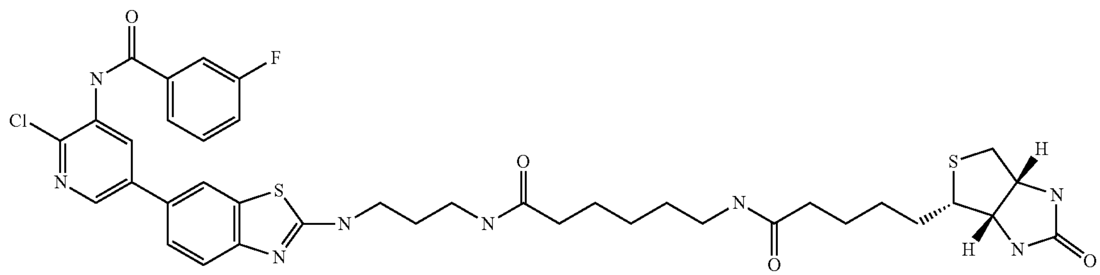 [SMILES: O=C(CCCC[C@@H]1SC[C@@H]2NC(=O)N[C@@H]21)NCCCCCC(=O)NCCCNc1nc2ccc(-c3cnc(Cl)c(NC(=O)c4cccc(F)c4)c3)cc2s1] |
| A27 | 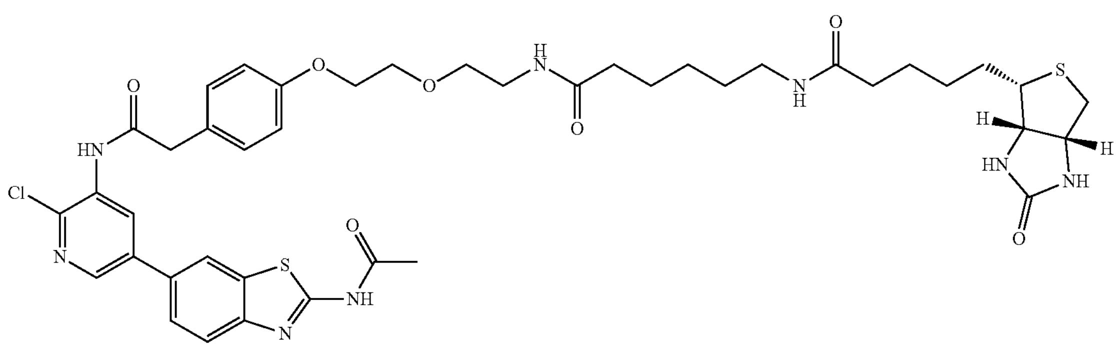 [SMILES: CC(=O)Nc1nc2ccc(-c3cnc(Cl)c(NC(=O)Cc4ccc(OCCOCCNC(=O)CCCCCNC(=O)CCCC[C@@H]5SC[C@@H]6NC(=O)N[C@@H]65)cc4)c3)cc2s1] |
| A32 | 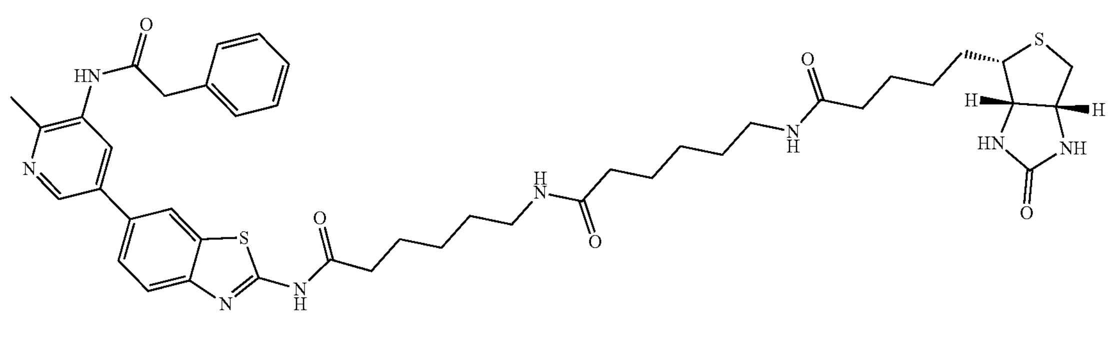 [SMILES: Cc1ncc(-c2ccc3nc(NC(=O)CCCCCNC(=O)CCCCCNC(=O)CCCC[C@@H]4SC[C@@H]5NC(=O)N[C@@H]54)sc3c2)cc1NC(=O)Cc1ccccc1] |

TABLE 1A-continued

Structures of selected compounds.

| Compd NO. | structure |
|---|---|
| A102 | (structure of compound A102) |

Biological Activities

Biological in Vitro HT29 Cell Assay.

Figure 3:
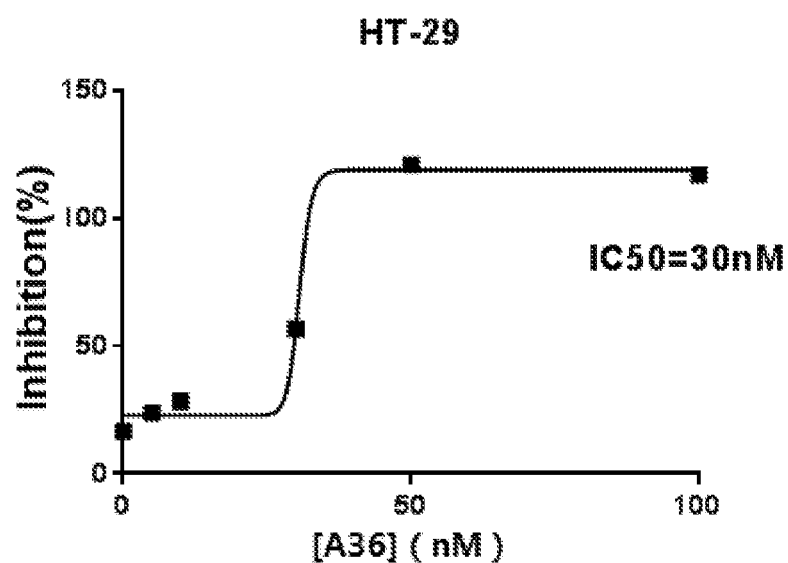
FIG. 3 depicts the inhibition of TNF-α induced-necrosis in HT29 cells by compound A36 in Example 55 and FIG. 4 depicts the inhibition of TNF-α induced-necrosis in L929 cells by compound A36 in Example 55.

The efficacies of RIP1 inhibitors were tested in vitro using human colon cancer TH29 cells in a necroptosis assay. For the assay, Cells were added to 96-well plates and then 10 μM of the test compound was pretreated for one hour. Then the cells were treated with TNF-α (40 ng/mL), Smacmimetic (100 nM) and z-VAD (20 μM) for 48 hours, and the viability was quantified. DMSO pretreatment group was negative control, Nec-1 pretreatment group was positive control. The compounds A5 and A36 were taken as an example, and the results are shown in FIGS. 1 and 3, respectively.

Biological In Vitro L929 Cell Assay.

Figure 2:
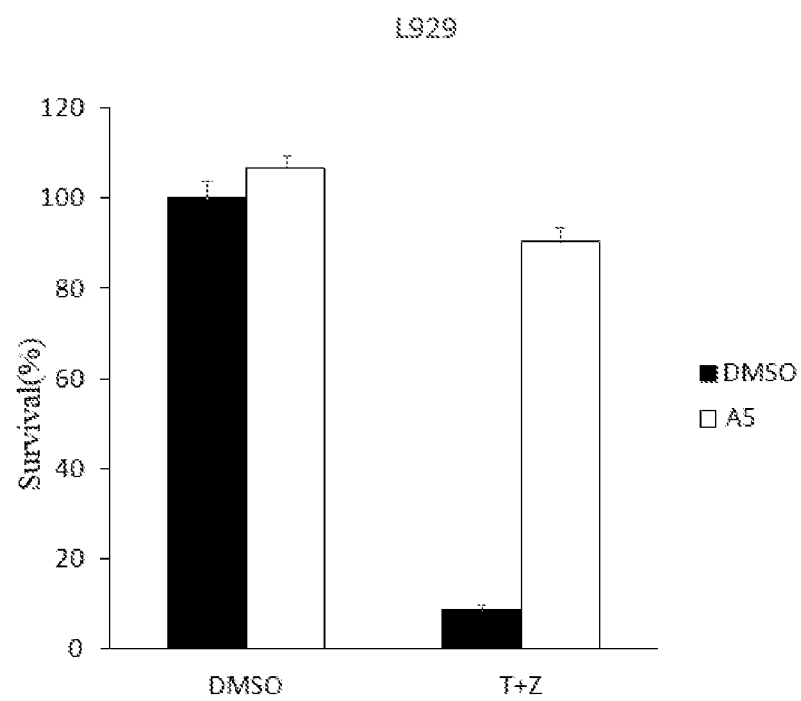
FIG. 2 depicts the inhibition of TNF-α induced-necrosis in L929 cells by compound A5 in Example 55.
Figure 4:
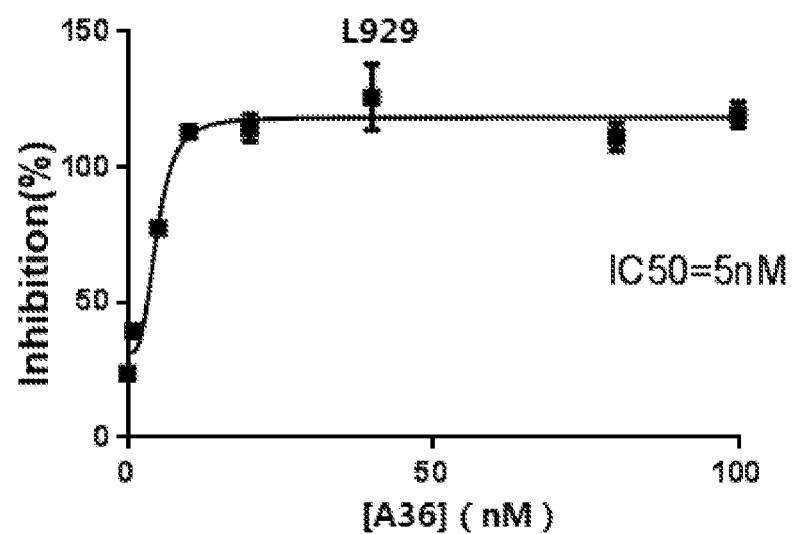

Mouse L-cells NCTC 929 (L929) were acquired from ATCC (cat. no. ATCC CCL-1) and banked in liquid nitrogen. The assay protocol was the same as described for the HT29 cell assay. The compounds A5 and A36 were taken as an example, and the results are shown in FIGS. 2 and 4, respectively.

TABLE 2

Biological activities of selected compounds

| Compound Number | HT29 Inhibition (10 μM) | HT29 $IC_{50}$ | L929 Inhibition (10 μM) | L929 $IC_{50}$ |
|---|---|---|---|---|
| A1 | 112% | ND | 48% | ND |
| A2 | 8% | ND | ND | ND |
| A3 | 7% | ND | 1% | ND |
| A4 | 25% | ND | 1% | ND |
| A5 | 50% | ND | 90% | ND |
| A6 | 5% | ND | ND | ND |
| A7 | 8% | ND | ND | ND |
| A8 | 10% | ND | ND | ND |
| A9 | 8% | ND | ND | ND |
| A10 | 1% | ND | ND | ND |
| A11 | 8% | ND | ND | ND |
| A12 | 11% | 2.56 μM | 80% | ND |
| A13 | 80% | 5.24 μM | 94% | ND |
| A14 | 71% | ND | 95% | ND |
| A15 | 95% | ND | 87% | ND |
| A16 | 36% | ND | 86% | ND |
| A17 | 45% | ND | ND | ND |
| A18 | 24% | ND | 51% | ND |
| A19 | 1% | ND | 22% | ND |
| A20 | 11% | ND | 69% | ND |
| A21 | 28% | 16.5 μM | 42% | ND |
| A22 | 66% | ND | 42% | ND |
| A23 | 104% | 670 nM | 42% | ND |
| A24 | 113% | 527 nM | 42% | ND |
| A25 | 68% | 255 nM | ND | ND |
| A26 | 30% | ND | 42% | ND |
| A27 | 48% | ND | 42% | ND |
| A28 | 34% | ND | 45% | ND |
| A29 | 81% | ND | 45% | ND |
| A30 | 38% | ND | 45% | ND |
| A31 | 87% | 3.4 μM | ND | ND |
| A32 | 21% | ND | ND | ND |
| A33 | 1% | ND | ND | ND |
| A34 | 1% | ND | ND | ND |
| A35 | 1% | ND | ND | ND |
| A36 | ND | 30 nM | ND | 5 nM |
| A37 | ND | 815 nM | ND | ND |
| A38 | 33% | ND | ND | ND |
| A39 | 9% | ND | ND | ND |
| A40 | 79% | 1.1 μM | ND | ND |
| A41 | 14% | ND | ND | ND |
| A42 | 22% | ND | ND | ND |
| A43 | 78% | 431 nM | ND | ND |
| A44 | 47% | 2.69 μM | ND | ND |
| A45 | ND | 430 nM | ND | 1.01 μM |
| A46 | ND | 900 nM | ND | 2.48 μM |
| A47 | ND | 124 nM | ND | ND |
| A48 | ND | 500 nM | ND | ND |
| A49 | ND | 357 nM | ND | ND |
| A50 | ND | 97 nM | ND | ND |
| A51 | ND | 73 nM | ND | ND |
| A52 | 10% | ND | ND | ND |
| A53 | ND | 2.19 μM | ND | ND |
| A54 | ND | 75 nM | ND | 200 nM |
| A55 | ND | 253 nM | ND | ND |
| A56 | ND | 700 nM | ND | 500 nM |
| A57 | ND | 92 nM | ND | 30 nM |
| A58 | ND | 1 μM | ND | 1 μM |
| A59 | ND | 689 nM | ND | ND |
| A60 | ND | 53 nM | ND | ND |
| A61 | ND | 1.2 nM | ND | 3 nM |
| A62 | ND | 63 nM | ND | ND |
| A63 | 9% | ND | ND | ND |
| A64 | ND | 1 μM | ND | ND |
| A65 | ND | 167 nM | ND | ND |
| A66 | ND | 247 nM | ND | ND |
| A67 | ND | 31 nM | ND | ND |
| A68 | ND | 31 nM | ND | ND |
| A69 | ND | 107 nM | ND | ND |
| A70 | ND | 93 nM | ND | ND |

TABLE 2-continued

Biological activities of selected compounds

| Compound Number | HT29 Inhibition (10 µM) | HT29 IC$_{50}$ | L929 Inhibition (10 µM) | L929 IC$_{50}$ |
|---|---|---|---|---|
| A71 | ND | 12 nM | ND | ND |
| A72 | ND | 534 nM | ND | ND |
| A73 | ND | 287 nM | ND | ND |
| A74 | 8% | ND | ND | ND |
| A75 | 6% | ND | ND | ND |
| A76 | 5% | ND | ND | ND |
| A77 | 60% | ND | ND | ND |
| A78 | ND | 867 nM | ND | ND |
| A79 | 35% | ND | ND | ND |
| A80 | ND | 653 nM | ND | ND |
| A81 | ND | 9 nM | ND | ND |
| A82 | 7% | ND | ND | ND |
| A83 | ND | 45 nM | ND | ND |
| A84 | ND | 31 nM | ND | ND |
| A85 | 7% | ND | ND | ND |
| A86 | ND | 87 nM | ND | ND |
| A87 | ND | 9 nM | ND | ND |
| A88 | ND | 40 nM | ND | ND |
| A89 | ND | 51 nM | ND | ND |
| A90 | ND | 300 nM | ND | ND |
| A91 | 40% | ND | ND | ND |
| A92 | ND | 121 nM | ND | ND |
| A93 | 8% | ND | ND | ND |
| A94 | ND | 10 nM | ND | ND |
| A95 | ND | 53 nM | ND | ND |
| A96 | 8% | ND | ND | ND |
| A97 | 7% | ND | ND | ND |
| A98 | 50% | ND | ND | ND |
| A99 | ND | 441 nM | ND | ND |
| A100 | 9% | ND | ND | ND |
| A101 | 5% | ND | ND | ND |
| A102 | 5% | ND | ND | ND |
| A103 | 20% | ND | ND | ND |
| A104 | ND | 60 nM | ND | ND |

What is claimed is:

1. A compound selected from the group consisting of:

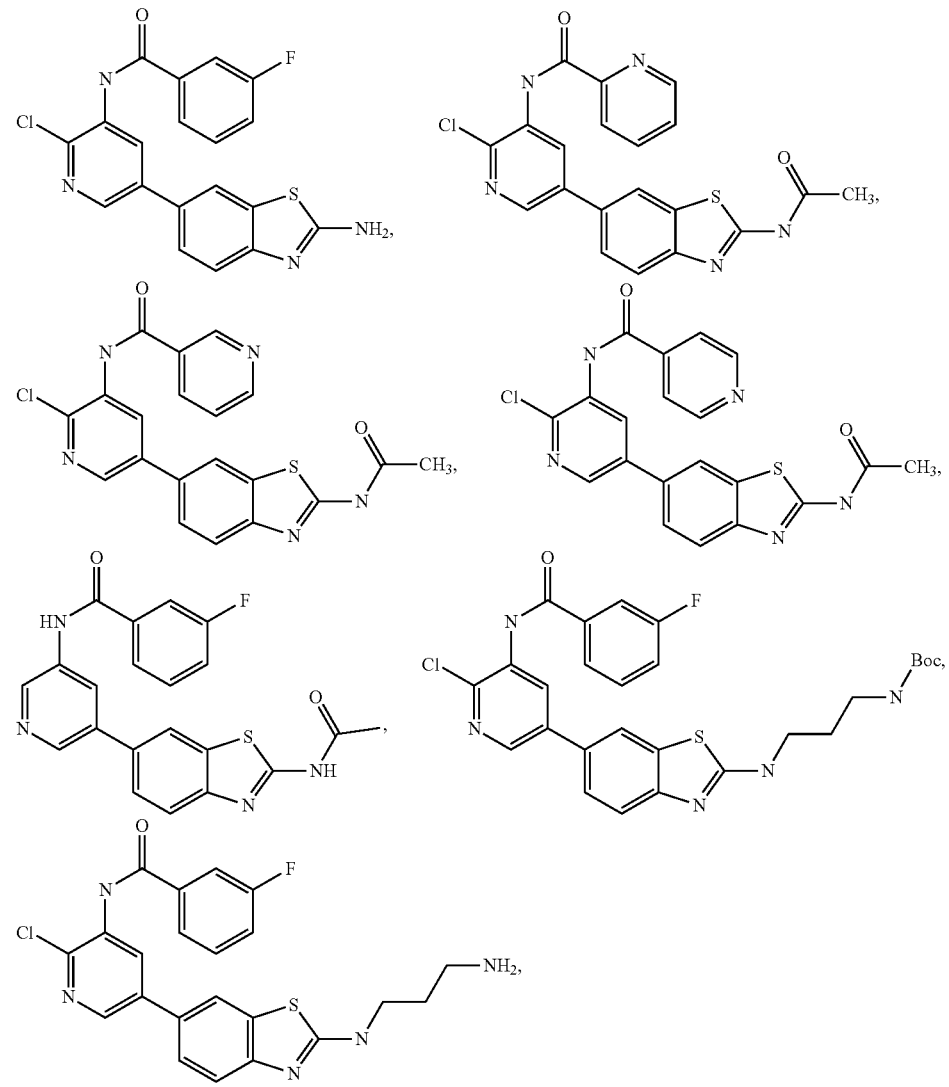

-continued
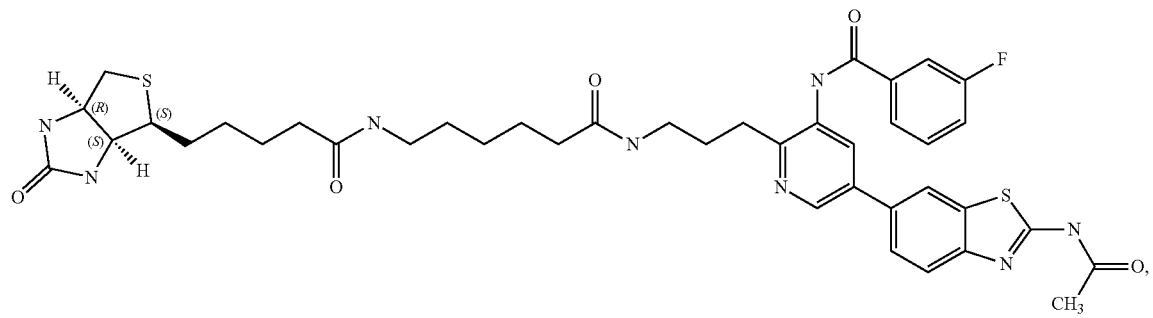
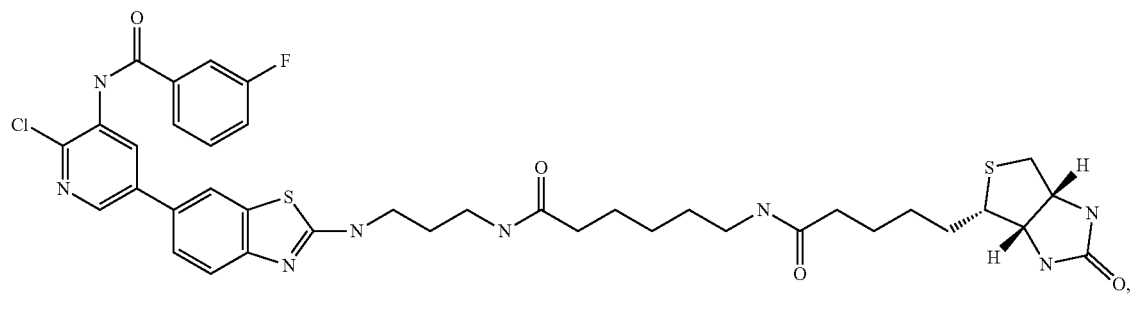
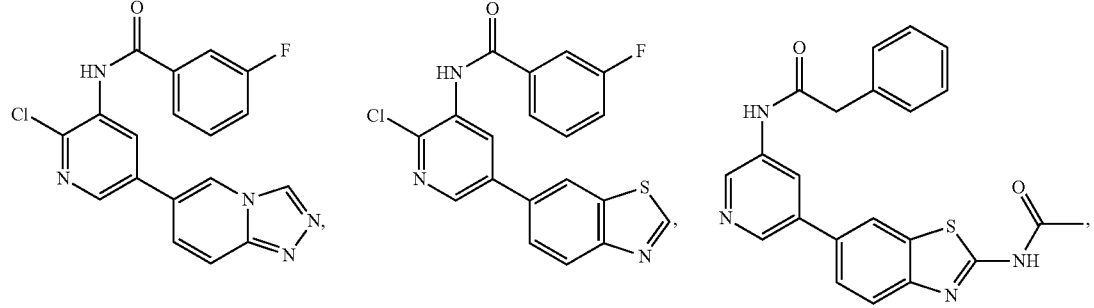
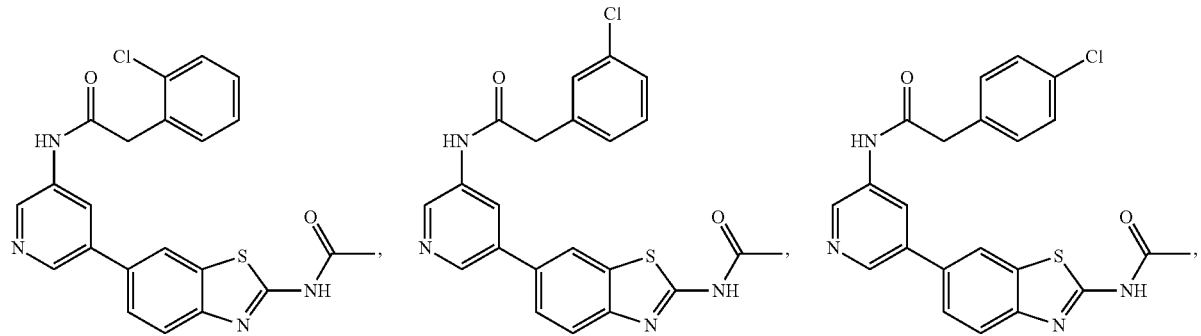
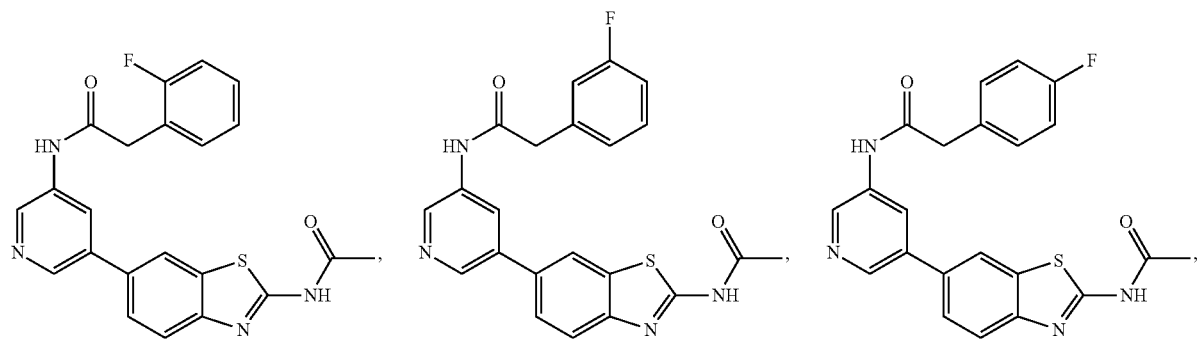

111
112
-continued
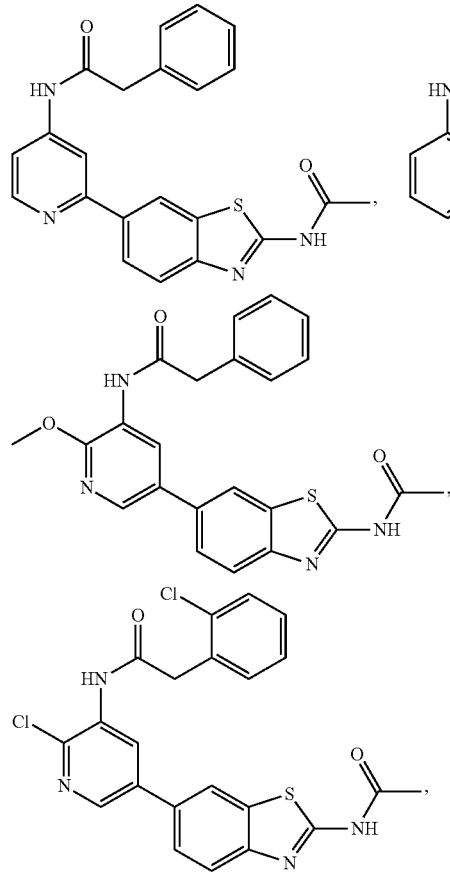
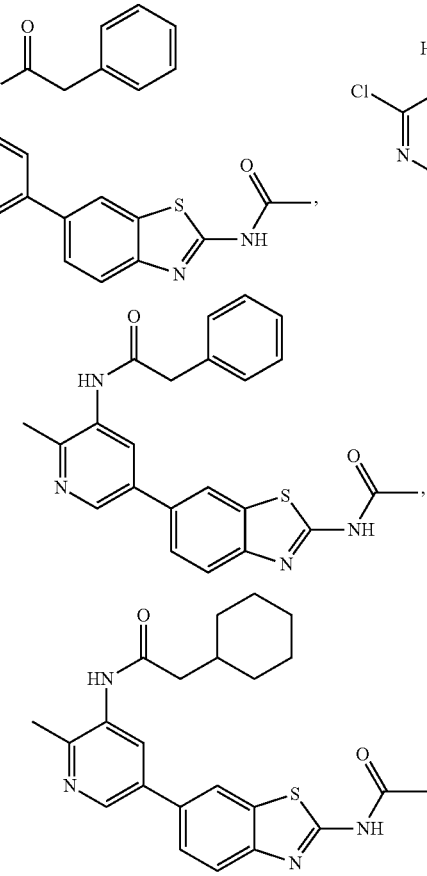
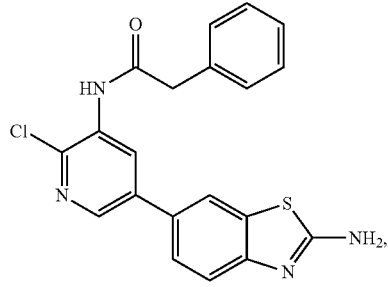
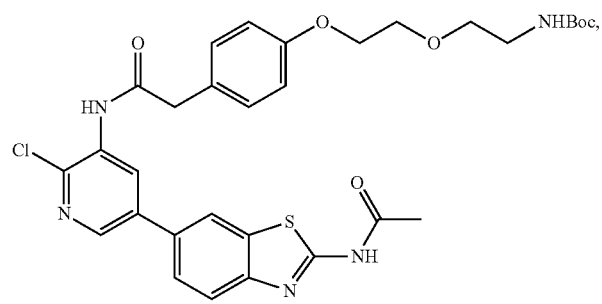
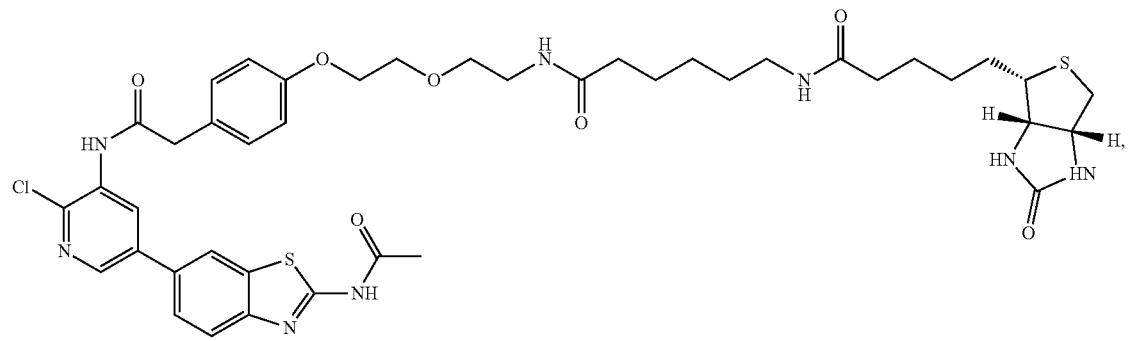

-continued
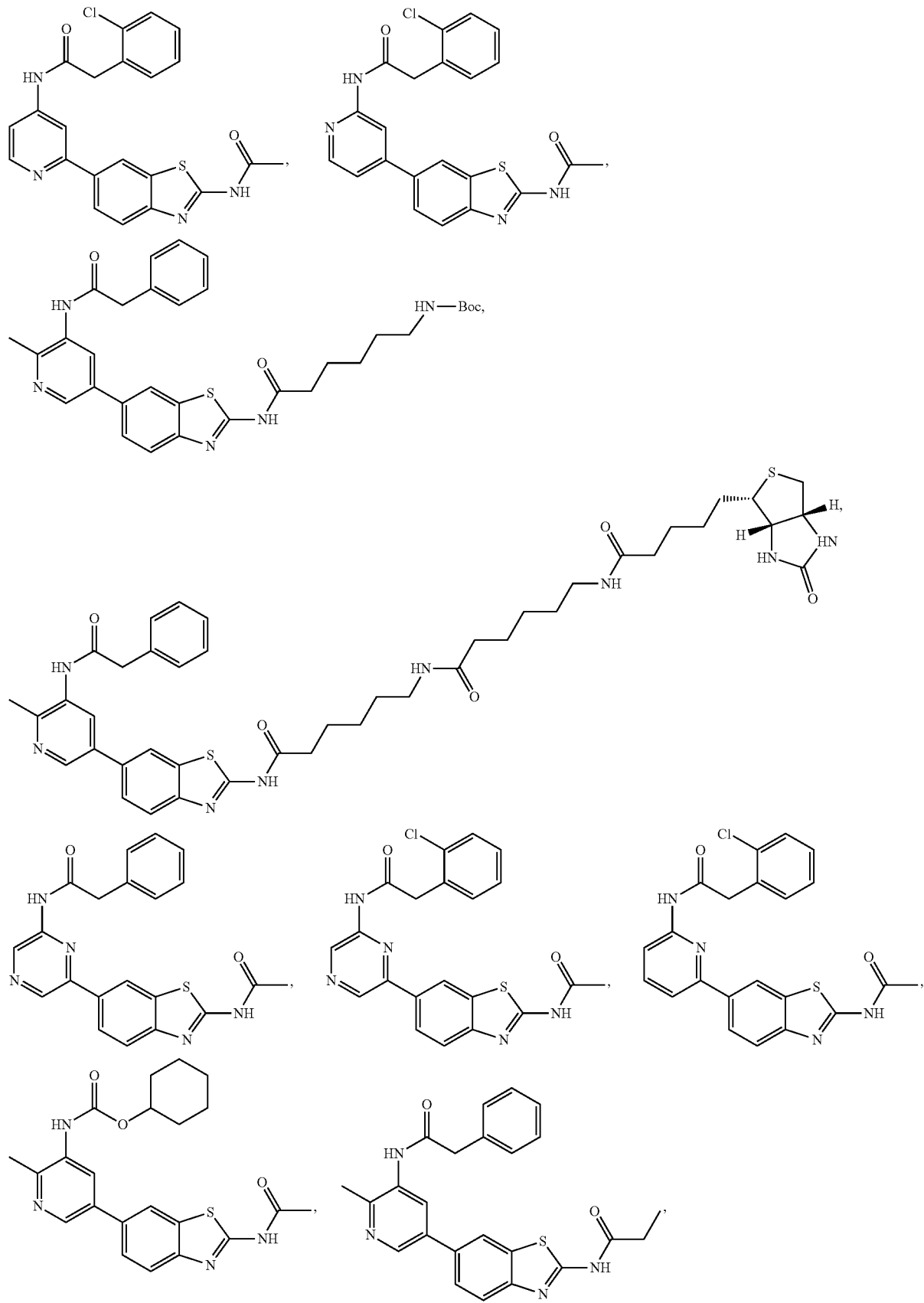

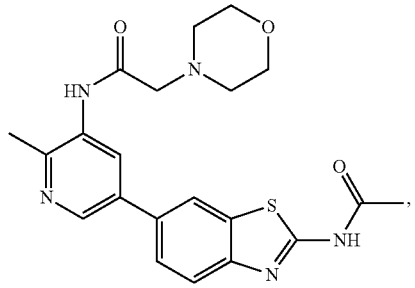
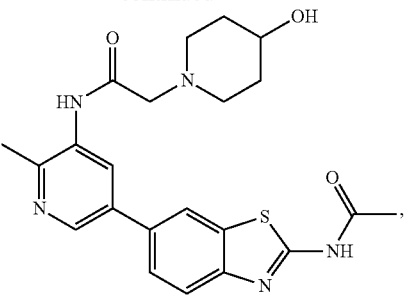
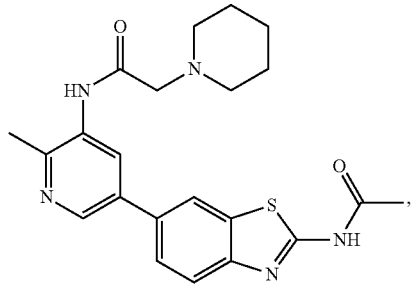
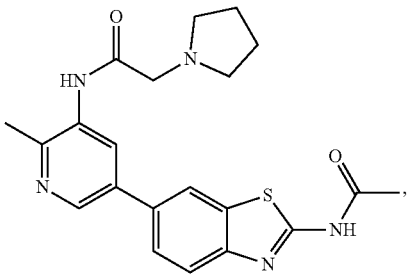
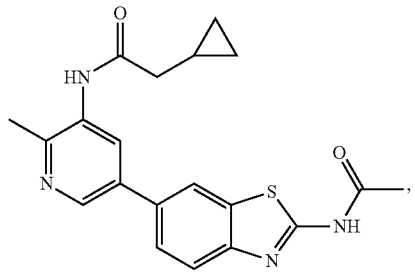
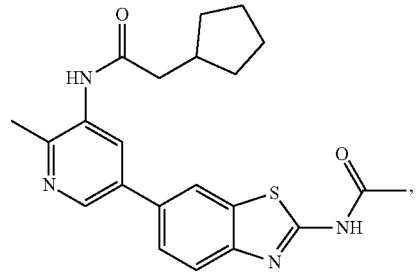
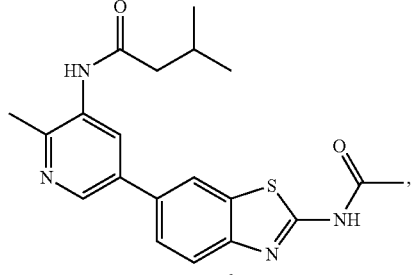
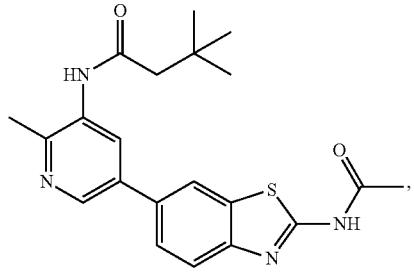
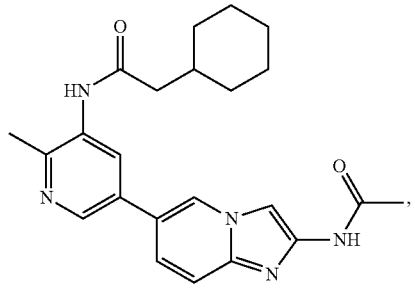
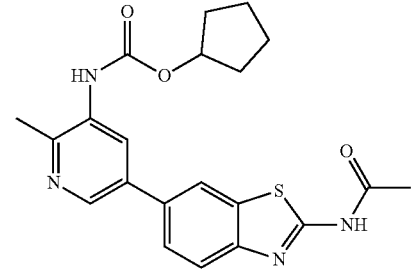
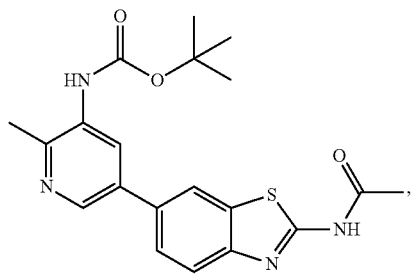
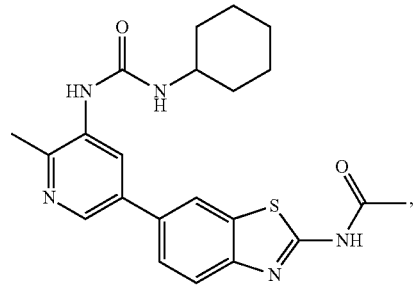

-continued
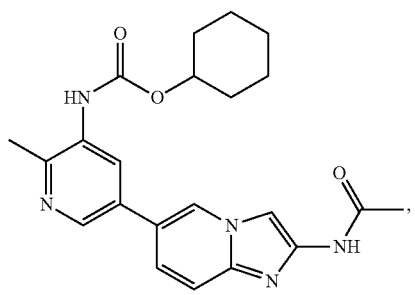
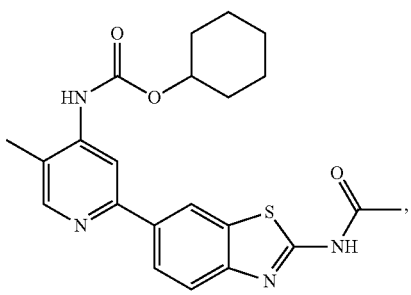
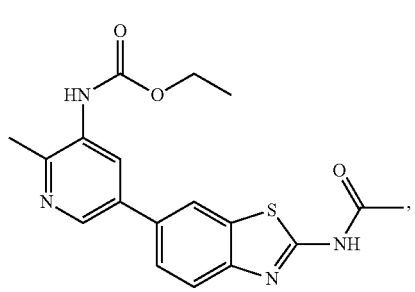
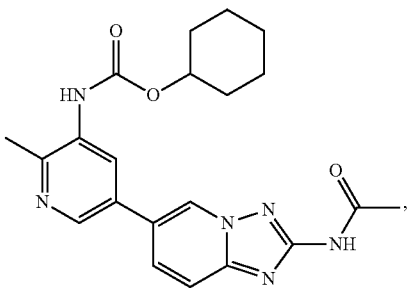
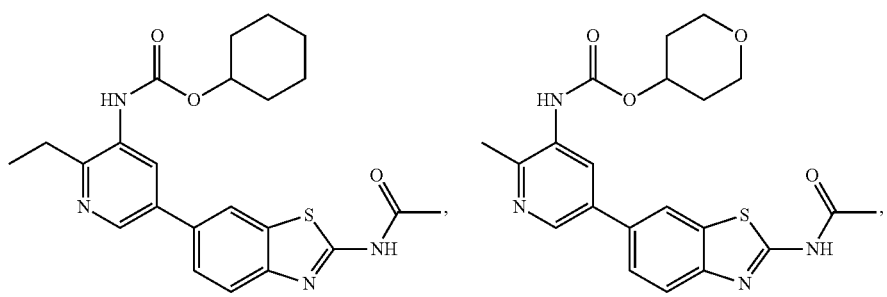
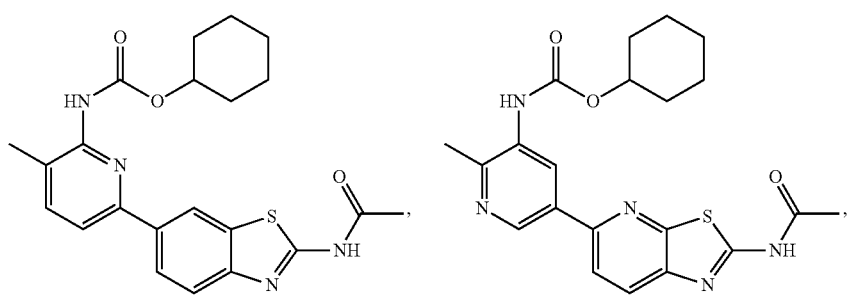
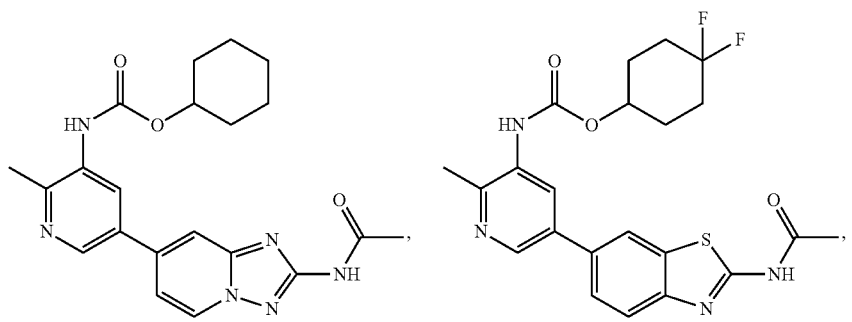

-continued
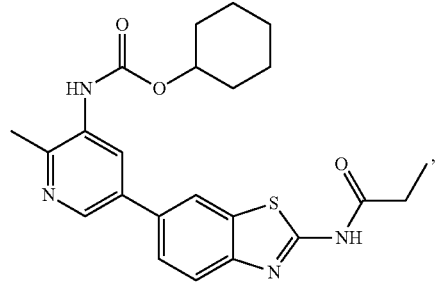
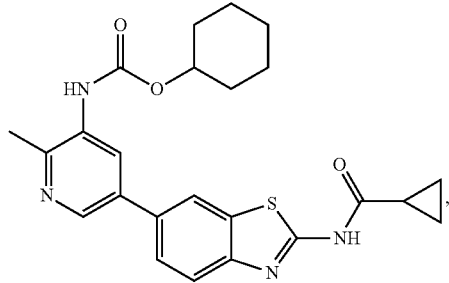
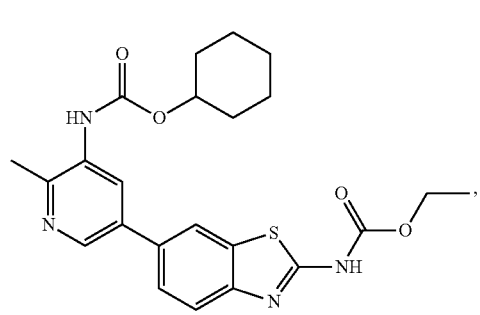
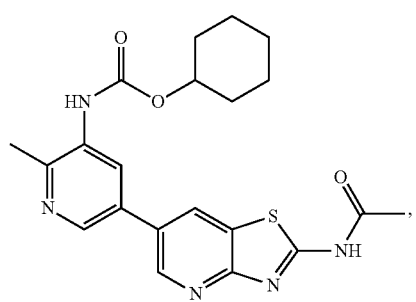
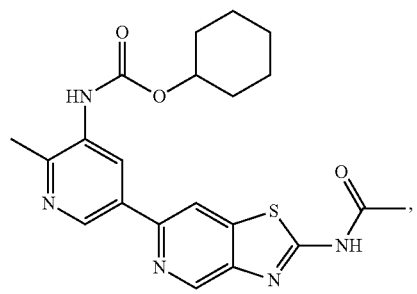
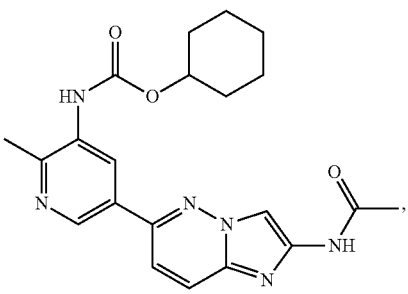
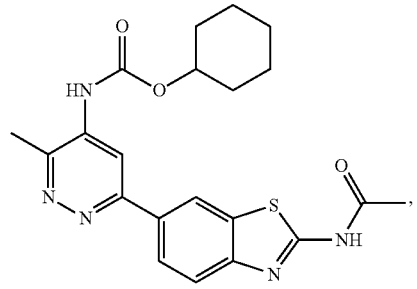
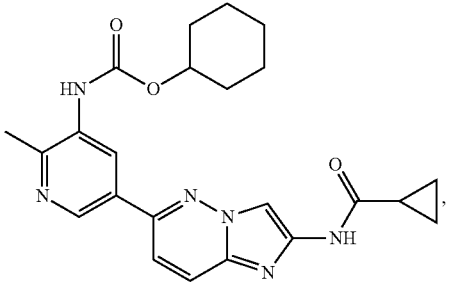
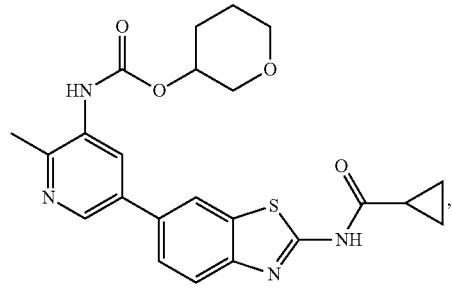
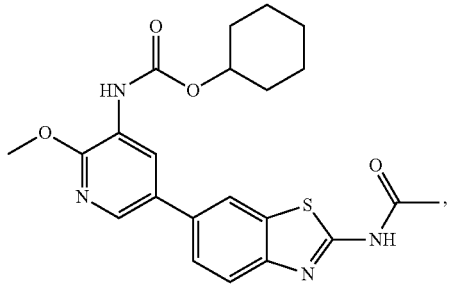

-continued
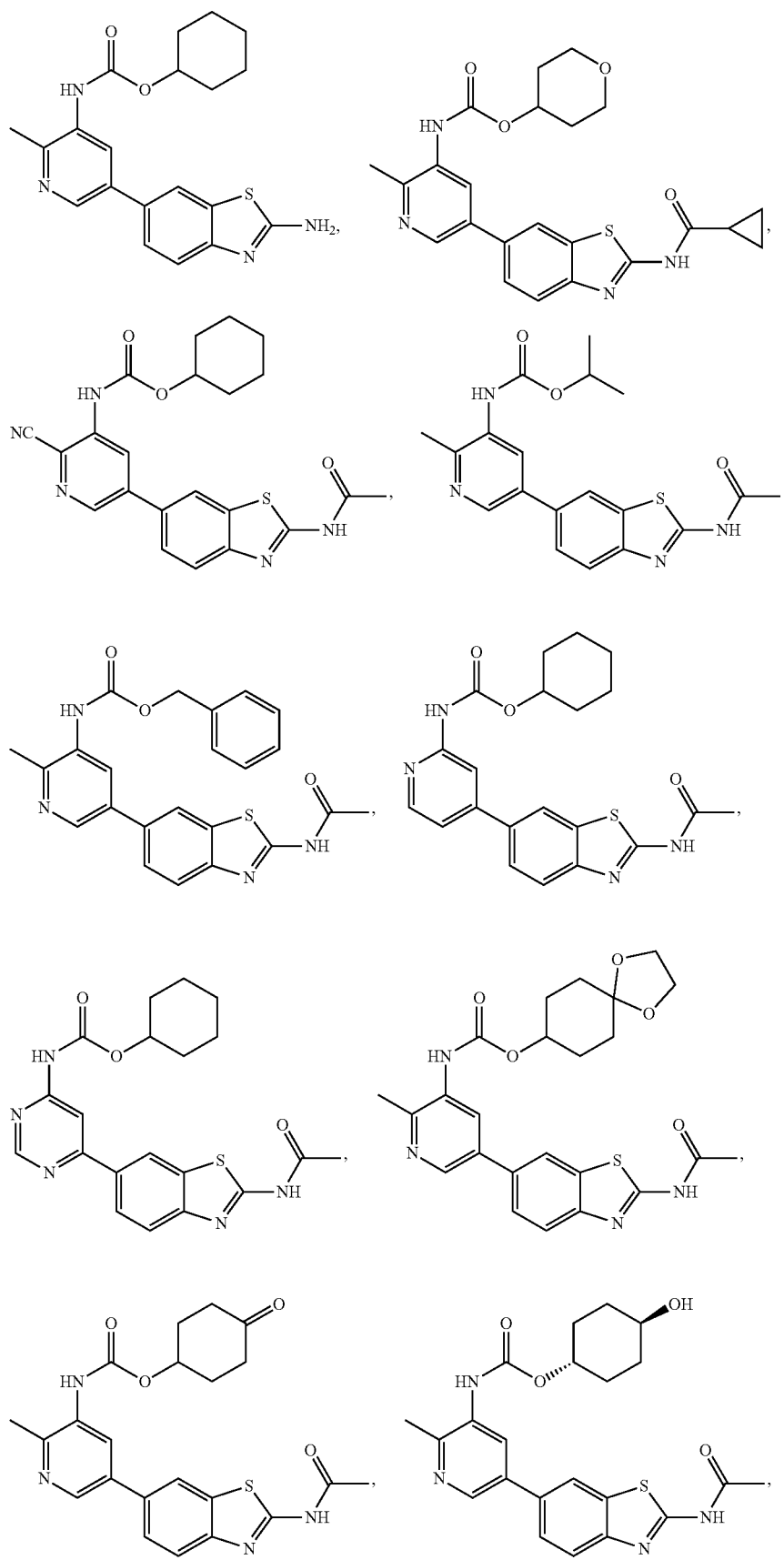

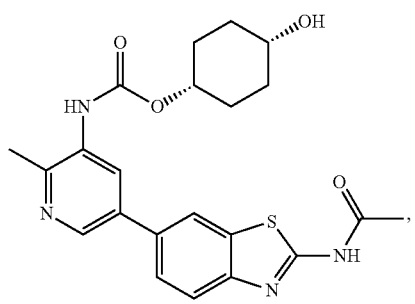
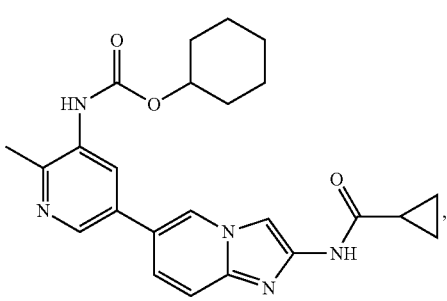
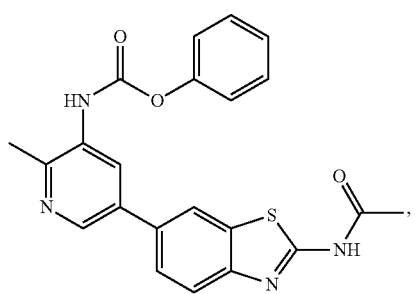
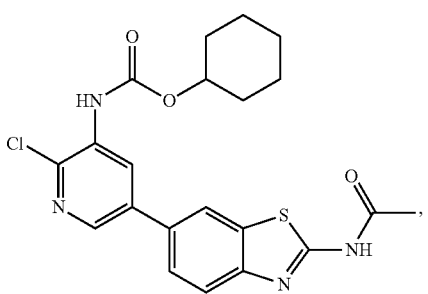
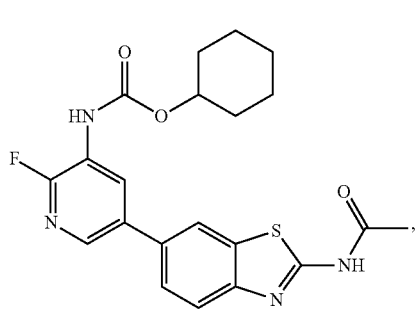
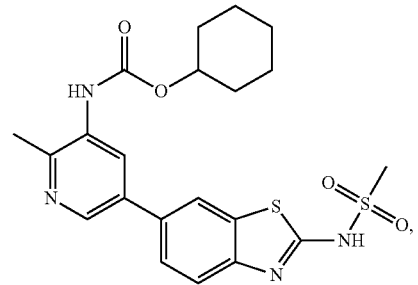
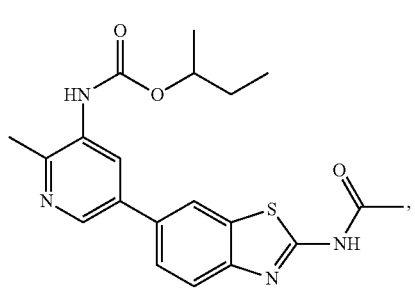
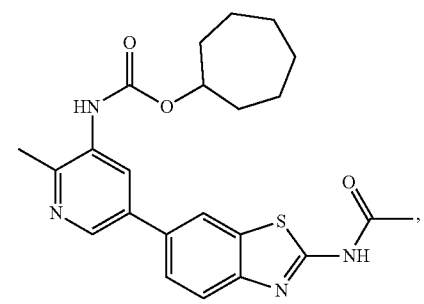
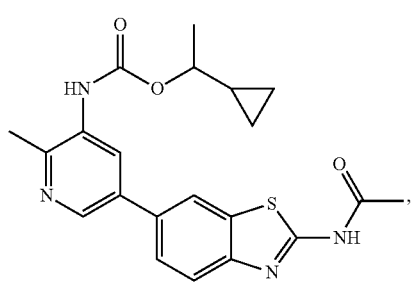
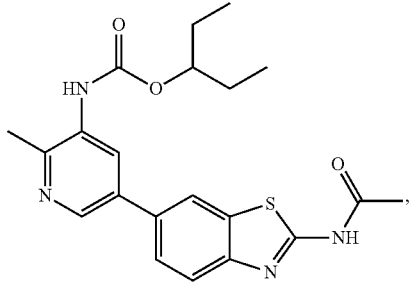

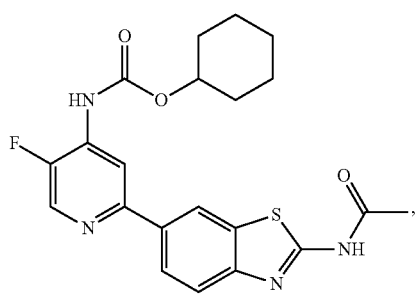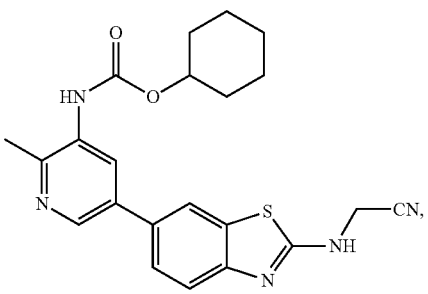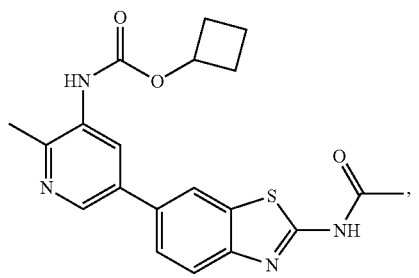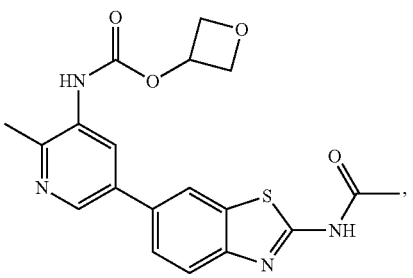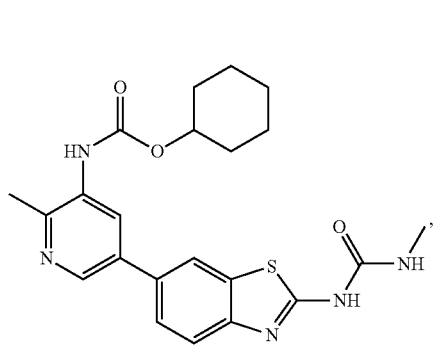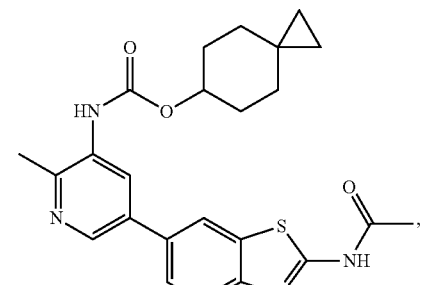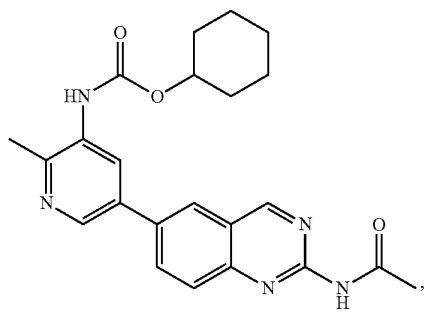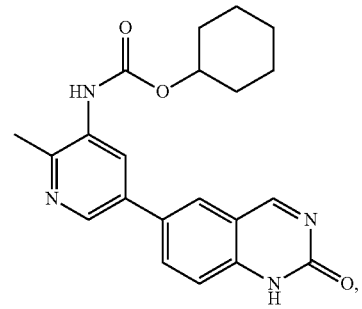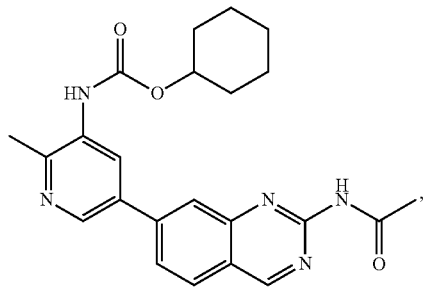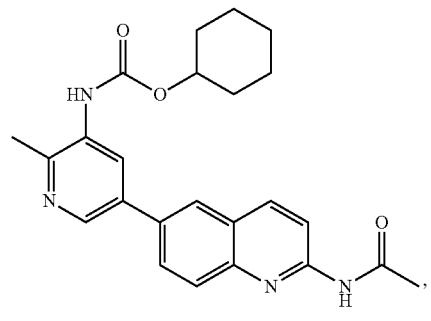

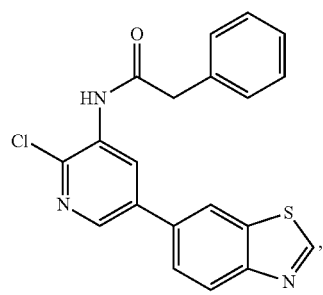

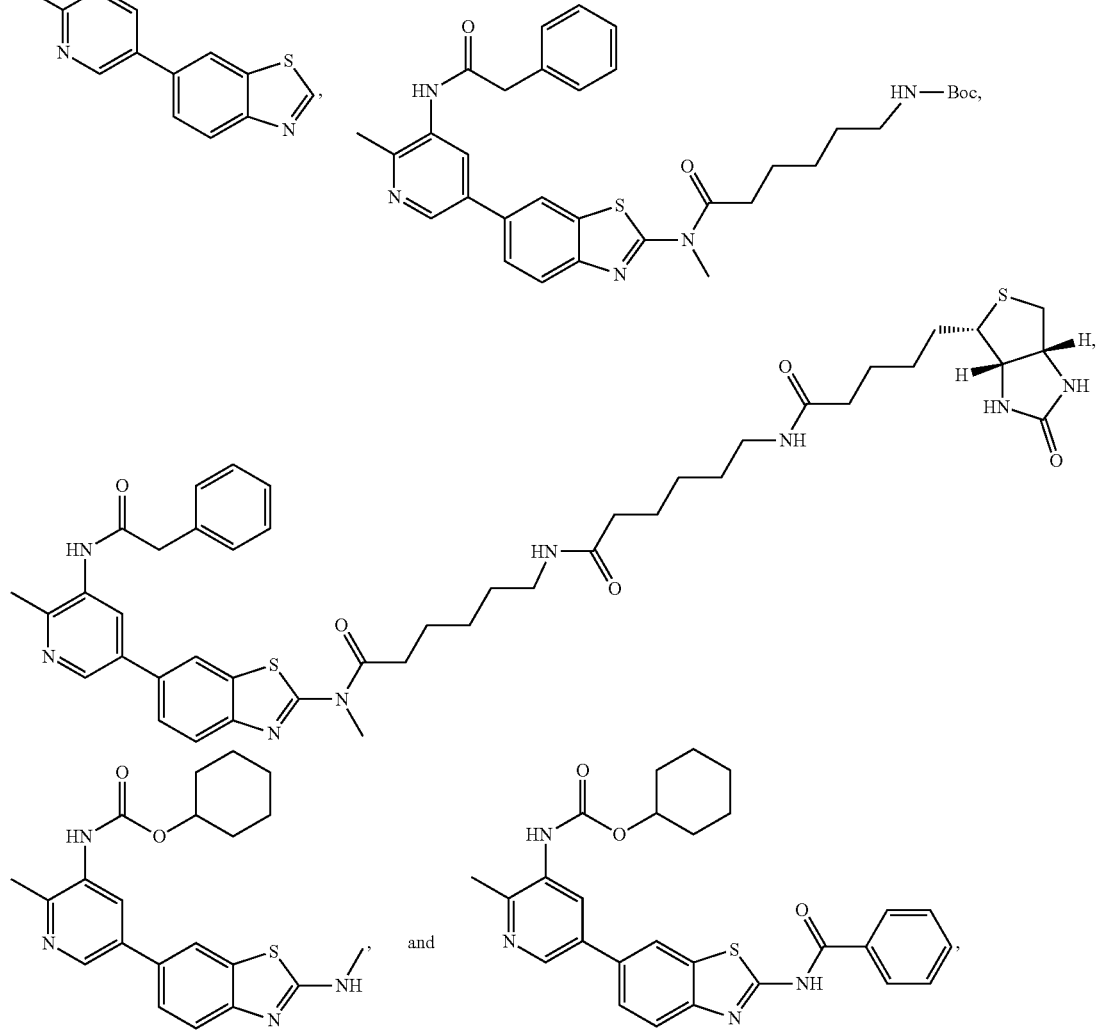

or a pharmaceutically acceptable salt, solvate, stereoisomer or a tautomer thereof.

2. A compound of Formula Ib:

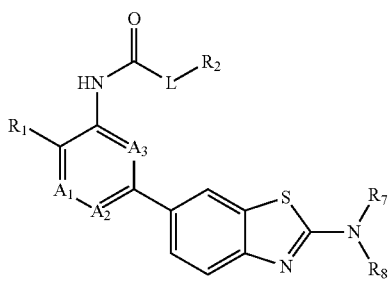

or a pharmaceutically acceptable salt, solvate, stereoisomer or a tautomer thereof, wherein $A_1$, $A_2$ and $A_3$ are independently N or $CR_3$, wherein at least one of $A_1$, $A_2$ and $A_3$ is N;

L is none, O, S, $NR_{12}$ or $CR_{12}R_{13}$;

$R_1$ is H, deuterium, halide, amino, —$NO_2$, —OH, —SH, —CN, $C_{1-6}$ alkyl, $C_{3-6}$ cycloalkyl, $C_{1-6}$ alkoxy, $C_{2-6}$ alkenyl, or $C_{2-6}$ alkynyl, wherein $C_{1-6}$ alkyl, $C_{3-6}$ cycloalkyl, $C_{1-6}$ alkoxy, $C_{2-6}$ alkenyl, $C_{2-6}$ alkynyl are unsubstituted or substituted with 1 to 3 groups selected from halide, deuterium, —CN, —$CF_3$, $C_{1-6}$ alkyl, $C_{3-6}$ cycloalkyl and $C_{1-6}$ alkoxy;

$R_2$ is $C_{1-6}$ alkyl, $C_{3-8}$ cycloalkyl, $C_{6-12}$ spirocycle, phenyl, 5-6 membered heteroaryl comprising 1-3 hetero atoms, 3-8 membered heterocycle comprising 1-3 hetero atoms, or 6-12 membered heterospirocycle comprising 1-3 hetero atoms, all of which are unsubstituted or substituted with 1-3 $R_9$, wherein each hetero atom is independently N, O or S;

$R_3$ is H, deuterium, halide, amino, —OH, —CN, $C_{1-6}$ alkoxy, $C_{1-6}$ alkylthio, $C_{3-6}$ cycloalkyl or $C_{1-6}$ alkyl;

$R_7$ is H, $C_{1-6}$ alkyl or $C_{3-6}$ cycloalkyl;

$R_8$ is H, $C(O)R_{10}$, $C(O)NR_{10}R_{11}$, $C(O)OR_{10}$, $S(O)_2R_{10}$, $S(O)_2NR_{10}R_{11}$, $C_{1-6}$ alkyl, $C_{3-6}$ cycloalkyl, $C_{2-6}$ alkenyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, phenyl, 3-6 membered heterocycle and 5-6 membered heteroaryl is unsubstituted or substituted with 1-3 groups selected from the group consisting of halide, deuterium, —CN, $C_{1-6}$ alkyl, $C_{3-6}$ cycloalkyl, $C_{1-6}$ alkoxy and 3-6 membered heterocycle comprising 1-3 hetero atoms, each hetero atom is independently N, O or S;

$R_9$ is H, deuterium, halide, —OH, oxy, —CN, -amino, $C_{1-6}$ alkyl, $C_{3-6}$ cycloalkyl or $C_{1-6}$ alkoxy, wherein each of $C_{1-6}$ alkyl, $C_{3-6}$ cycloalkyl, and $C_{1-6}$ alkoxy is unsubstituted or substituted with 1-3 groups selected from the group consisting of halide, deuterium, and $C_{1-3}$ alkyl;

each of $R_{10}$ and $R_{11}$ is independently H, $C_{1-6}$ alkyl, $C_{3-6}$ cycloalkyl, $C_{2-6}$ alkenyl, $C_{2-6}$ alkynyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, $C_{2-6}$ alkenyl, $C_{2-6}$ alkynyl, phenyl, 3-6 membered heterocycle and 5-6 membered heteroaryl is unsubstituted or substituted with 1-3 groups consisting of halide, deuterium, —CN, —OH, —CF$_3$, $C_{1-6}$ alkyl, $C_{3-6}$ cycloalkyl, $C_{1-6}$ alkoxy and 5-6 membered heteroaryl comprising 1-3 hetero atoms, each hetero atom is independently N, O or S; or $R_{10}$ and $R_{11}$ together, with nitrogen atom they attached to, form a first 5-6 membered ring; or $R_{10}$ and $R_5$ together, with adjacent atoms they attached to, form a second 5-6 membered ring; and each of $R_{12}$ and $R_{13}$ is independently H, deuterium, halide, —OH, $C_3$ alkyl or $C_{1-6}$ alkoxy;

with the proviso that when L is none, $R_2$ is not methyl.

3. The compound of claim 2, wherein $A_1$ is N;
$A_2$ is CH;
$A_3$ is CH;
$R_1$ is halide, amino, —NO$_2$, —OH, —SH, —CN, $C_{1-6}$ alkyl, $C_{3-6}$ cycloalkyl, $C_{1-6}$ alkoxy, $C_{2-6}$ alkenyl, or $C_{2-6}$ alkynyl, wherein $C_{1-6}$ alkyl, $C_{3-6}$ cycloalkyl, $C_{1-6}$ alkoxy, $C_{2-6}$ alkenyl, $C_{2-6}$ alkynyl are unsubstituted or substituted with 1 to 3 groups selected from halide, deuterium, —CN, —CF$_3$, $C_{1-6}$ alkyl, $C_{3-6}$ cycloalkyl and $C_{1-6}$ alkoxy;

L is none, O, $NR_{12}$ or $CR_{12}R_{13}$;

$R_2$ is $C_{1-6}$ alkyl, $C_{3-8}$ cycloalkyl, $C_{6-12}$ spirocycle, phenyl, 5-6 membered heteroaryl comprising 1-3 hetero atoms, 3-8 membered heterocycle comprising 1-3 hetero atoms, or 6-12 membered heterospirocycle comprising 1-3 hetero atoms, all of which are unsubstituted or substituted with 1-3 $R_9$, wherein each hetero atom is independently N, O or S, with the proviso that when L is none, $R_2$ is not methyl;

$R_7$ is H; and $R_8$ is $C(O)R_{10}$, $C(O)NR_{10}R_{11}$, $C(O)OR_{10}$, $S(O)_2R_{10}$, or $S(O)_2NR_{10}R_{11}$.

4. The compound of claim 3, wherein $R_{10}$ is $C_{1-6}$ alkyl, $C_{3-6}$ cycloalkyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, phenyl, 3-6 membered heterocycle and 5-6 membered heteroaryl is unsubstituted or substituted with 1-3 groups selected from the group consisting of halide, deuterium, —CN, —OH, —CF$_3$, $C_{1-6}$ alkyl, $C_{3-6}$ cycloalkyl, $C_{1-6}$ alkoxy and 5-6 membered heteroaryl comprising 1-3 hetero atoms, each hetero atom is independently N, O or S; or $R_{10}$ and $R_{11}$ together, with nitrogen atom they attached to, form a first 5-6 membered ring; and $R_{11}$ is H, $C_{1-6}$ alkyl, $C_{3-6}$ cycloalkyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, phenyl, 3-6 membered heterocycle and 5-6 membered heteroaryl is unsubstituted or substituted with 1-3 groups selected from the group consisting of halide, deuterium, —CN, —OH, —CF$_3$, $C_{1-6}$ alkyl, $C_{3-6}$ cycloalkyl, $C_{1-6}$ alkoxy and 5-6 membered heteroaryl comprising 1-3 hetero atoms, each hetero atom is independently N, O or S; or $R_{10}$ and $R_{11}$ together, with nitrogen atom they attached to, form a first 5-6 membered ring.

5. A compound of Formula I:

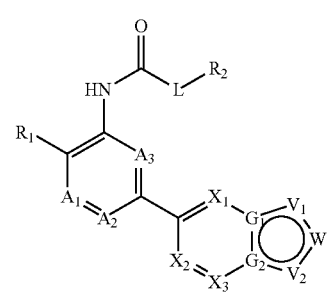

or a pharmaceutically acceptable salt, solvate, stereoisomer or a tautomer thereof, wherein $A_1$, $A_2$ and $A_3$ are independently N or $CR_3$, wherein at least one of $A_1$, $A_2$ and $A_3$ is N;

$X_1$, $X_2$ and $X_3$ are independently N or $CR_4$;

$G_1$ and $G_2$ are independently N or C;

$V_1$ and $V_2$ are independently N, O, S, $NR_5$ or $CR_3$;

L is O, NH or $CH_2$;

$R_1$ is H, deuterium, halide, amino, —NO$_2$, —OH, —SH, —CN, $C_{1-6}$ alkyl, $C_{3-6}$ cycloalkyl, $C_{1-6}$ alkoxy, $C_{2-6}$ alkenyl, or $C_{2-6}$ alkynyl, wherein $C_{1-6}$ alkyl, $C_{3-6}$ cycloalkyl, $C_{1-6}$ alkoxy, $C_{2-6}$ alkenyl, $C_{2-6}$ alkynyl are unsubstituted or substituted with 1 to 3 groups selected from halide, deuterium, —CN, —CF$_3$, $C_{1-6}$ alkyl, $C_{3-6}$ cycloalkyl and $C_{1-6}$ alkoxy;

$R_2$ is $C_{1-6}$ alkyl, $C_{3-8}$ cycloalkyl, $C_{6-12}$ spirocycle, phenyl, 5-6 membered heteroaryl comprising 1-3 hetero atoms, 3-8 membered heterocycle comprising 1-3 hetero atoms, or 6-12 membered heterospirocycle comprising 1-3 hetero atoms, all of which are unsubstituted or substituted with 1-3 $R_9$, wherein each hetero atom is independently N, O or S;

W is C—$NR_7R_8$;

each of $R_3$, $R_4$ and $R_5$ is independently H, deuterium, halide, amino, —OH, —CN, $C_{1-6}$ alkoxy, $C_{1-6}$ alkylthio, $C_{3-6}$ cycloalkyl or $C_{1-6}$ alkyl;

$R_7$ is H; and $R_8$ is $C(O)R_{10}$, $C(O)NR_{10}R_{11}$, $C(O)OR_{10}$, $S(O)_2R_{10}$, or $S(O)_2NR_{10}R_{11}$;

$R_9$ is H, deuterium, halide, —OH, oxy, —CN, -amino, $C_{1-6}$ alkyl, $C_{3-6}$ cycloalkyl or $C_{1-6}$ alkoxy, wherein each of $C_{1-6}$ alkyl, $C_{3-6}$ cycloalkyl, and $C_{1-6}$ alkoxy is unsubstituted or substituted with 1-3 groups selected from the group consisting of halide, deuterium, and $C_{1-3}$ alkyl;

each of $R_{10}$ and $R_{11}$ is independently H, $C_{1-6}$ alkyl, $C_{3-6}$ cycloalkyl, $C_{2-6}$ alkenyl, $C_{2-6}$ alkynyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, $C_{2-6}$ alkenyl, $C_{2-6}$ alkynyl, phenyl, 3-6 membered heterocycle and 5-6 membered heteroaryl is unsubstituted or substituted with 1-3 groups selected from the group consisting of halide, deuterium, —CN, —OH, —CF$_3$, $C_{1-6}$ alkyl, $C_{3-6}$ cycloalkyl, $C_{1-6}$ alkoxy and 5-6 membered heteroaryl comprising 1-3 hetero atoms, each hetero atom is independently N, O or S; or $R_{10}$ and $R_{11}$ together, with nitrogen atom they attached to, form a first 5-6 membered ring; or $R_{10}$ and $R_5$ together, with adjacent atoms they attached to, form a second 5-6 membered ring.

6. The compound of claim 5, wherein $R_{10}$ is $C_{1-6}$ alkyl, $C_{3-6}$ cycloalkyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, phenyl, 3-6 membered heterocycle and 5-6 membered heteroaryl is unsubstituted or substituted with 1-3 groups selected from the group consisting of halide, deuterium, —CN, —OH, —CF$_3$, $C_{1-6}$ alkyl, $C_{3-6}$ cycloalkyl, $C_{1-6}$ alkoxy and 5-6 membered heteroaryl comprising 1-3 hetero atoms, each hetero atom is independently N, O or S; or $R_{10}$ and $R_{11}$ together, with nitrogen atom they attached to, form a first 5-6 membered ring; and $R_{11}$ is H, $C_{1-6}$ alkyl, $C_{3-6}$ cycloalkyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, phenyl, 3-6 membered heterocycle and 5-6 membered heteroaryl is unsubstituted or substituted with 1-3 groups selected from the group consisting of halide, deuterium, —CN, —OH, —CF$_3$, $C_{1-6}$ alkyl, $C_{3-6}$ cycloalkyl, $C_{1-6}$ alkoxy and 5-6 membered heteroaryl comprising 1-3 hetero atoms, each hetero atom is independently N, O or S; or $R_{10}$ and $R_{11}$ together, with nitrogen atom they attached to, form a first 5-6 membered ring.

7. A compound of Formula Ic:

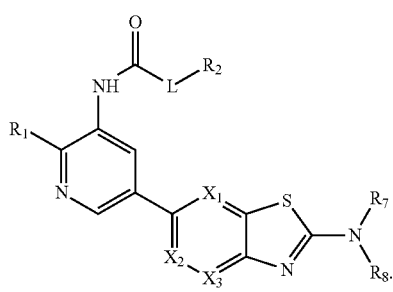

Ic or a pharmaceutically acceptable salt, solvate, stereoisomer or a tautomer thereof, wherein $X_1$, $X_2$ and $X_3$ are independently N or CR$_4$;

L is none, O, S, NR$_{12}$ or CR$_{12}$R$_{13}$;

$R_1$ is H, deuterium, halide, amino, —NO$_2$, —OH, —SH, —CN, $C_{1-6}$ alkyl, $C_{3-6}$ cycloalkyl, $C_{1-6}$ alkoxy, $C_{2-6}$ alkenyl, or $C_{2-6}$ alkynyl, wherein $C_{1-6}$ alkyl, $C_{3-6}$ cycloalkyl, $C_{1-6}$ alkoxy, $C_{2-6}$ alkenyl, $C_{2-6}$ alkynyl are unsubstituted or substituted with 1 to 3 groups selected from halide, deuterium, —CN, —CF$_3$, $C_{1-6}$ alkyl, $C_{3-6}$ cycloalkyl and $C_{1-6}$ alkoxy;

$R_2$ is $C_{1-6}$ alkyl, $C_{3-8}$ cycloalkyl, $C_{6-12}$ spirocycle, phenyl, 5-6 membered heteroaryl comprising 1-3 hetero atoms, 3-8 membered heterocycle comprising 1-3 hetero atoms, or 6-12 membered heterospirocycle comprising 1-3 hetero atoms, all of which are unsubstituted or substituted with 1-3 R$_9$, wherein each hetero atom is independently N, O or S, with the proviso that when L is none, R$_2$ is not methyl;

each of $R_4$ and $R_5$ is independently H, deuterium, halide, amino, —OH, —CN, $C_{1-6}$ alkoxy, $C_{1-6}$ alkylthio, $C_{3-6}$ cycloalkyl or $C_{1-6}$ alkyl;

$R_6$ is H, deuterium, halide, —OH, —CN, $C_{1-6}$ alkoxy, $C_{1-6}$ alkyl; $C_{3-6}$ cycloalkyl or —NR$_7$R$_8$;

$R_7$ is H, $C_{1-6}$ alkyl or $C_{3-6}$ cycloalkyl;

$R_8$ is H, C(O)R$_{10}$, C(O)NR$_{10}$R$_{11}$, C(O)OR$_{10}$, S(O)$_2$R$_{10}$, S(O)$_2$NR$_{10}$R$_{11}$, $C_{1-6}$ alkyl, $C_{3-6}$ cycloalkyl, $C_{2-6}$ alkenyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, phenyl, 3-6 membered heterocycle and 5-6 membered heteroaryl is unsubstituted or substituted with 1-3 groups selected from the group consisting of halide, deuterium, —CN, $C_{1-6}$ alkyl, $C_{3-6}$ cycloalkyl, $C_{1-6}$ alkoxy and 3-6 membered heterocycle comprising 1-3 hetero atoms, each hetero atom is independently N, O or S;

$R_9$ is H, deuterium, halide, —OH, oxy, —CN, -amino, $C_{1-6}$ alkyl, $C_{3-6}$ cycloalkyl or $C_{1-6}$ alkoxy, wherein each of $C_{1-6}$ alkyl, $C_{3-6}$ cycloalkyl, and $C_{1-6}$ alkoxy is unsubstituted or substituted with 1-3 groups selected from the group consisting of halide, deuterium, and $C_{1-3}$ alkyl;

each of $R_{10}$ and $R_{11}$ is independently H, $C_{1-6}$ alkyl, $C_{3-6}$ cycloalkyl, $C_{2-6}$ alkenyl, $C_{2-6}$ alkynyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, $C_{2-6}$ alkenyl, $C_{2-6}$ alkynyl, phenyl, 3-6 membered heterocycle and 5-6 membered heteroaryl is unsubstituted or substituted with 1-3 groups selected from the group consisting of halide, deuterium, —CN, —OH, —CF$_3$, $C_{1-6}$ alkyl, $C_{3-6}$ cycloalkyl, $C_{1-6}$ alkoxy and 5-6 membered heteroaryl comprising 1-3 hetero atoms, each hetero atom is independently N, O or S; or $R_{10}$ and $R_{11}$ together, with nitrogen atom they attached to, form a first 5-6 membered ring; or $R_{10}$ and $R_5$ together, with adjacent atoms they attached to, form a second 5-6 membered ring; and each of $R_{12}$ and $R_{13}$ is independently H, deuterium, halide, —OH, $C_{1-3}$ alkyl or $C_{1-6}$ alkoxy.

8. The compound of claim 7, wherein $X_1$ is CH;

$X_2$ is CH;

$X_3$ is CH;

L is O, NH or CH$_2$;

$R_1$ is halide, $C_{1-6}$ alkyl, $C_{3-6}$ cycloalkyl, or $C_{1-6}$ alkoxy, wherein $C_{1-6}$ alkyl, $C_{3-6}$ cycloalkyl, or $C_{1-6}$ alkoxy are unsubstituted or substituted with 1 to 3 groups selected from halide, deuterium, —CN, —CF$_3$, $C_{1-6}$ alkyl, $C_{3-6}$ cycloalkyl and $C_{1-6}$ alkoxy;

$R_2$ is $C_{1-6}$ alkyl, $C_{3-8}$ cycloalkyl, $C_{6-12}$ spirocycle, phenyl, 5-6 membered heteroaryl comprising 1-3 hetero atoms, 3-8 membered heterocycle comprising 1-3 hetero atoms, or 6-12 membered heterospirocycle comprising 1-3 hetero atoms, all of which are unsubstituted or substituted with 1-3 $R_9$, wherein each hetero atom is independently N, O or S;

$R_7$ is H; and $R_8$ is $C(O)R_{10}$, $C(O)NR_{10}R_{11}$, or $C(O)OR_{10}$, each of $R_{10}$ and $R_{11}$ is independently H, $C_{1-6}$ alkyl, $C_{3-6}$ cycloalkyl, $C_{2-6}$ alkenyl, $C_{2-6}$ alkynyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, $C_{2-6}$ alkenyl, $C_{2-6}$ alkynyl, phenyl, 3-6 membered heterocycle and 5-6 membered heteroaryl is unsubstituted or substituted with 1-3 groups selected from the group consisting of halide, deuterium, —CN, —OH, —$CF_3$, $C_{1-6}$ alkyl, $C_{3-6}$ cycloalkyl, $C_{1-6}$ alkoxy and 5-6 membered heteroaryl comprising 1-3 hetero atoms, each hetero atom is independently N, O or S; or $R_{10}$ and $R_{11}$ together, with nitrogen atom they attached to, form a first 5-6 membered ring.

9. The compound of claim 8, wherein $R_{10}$ is $C_{1-6}$ alkyl, $C_{3-6}$ cycloalkyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, phenyl, 3-6 membered heterocycle and 5-6 membered heteroaryl is unsubstituted or substituted with 1-3 groups selected from the group consisting of halide, deuterium, —CN, —OH, —$CF_3$, $C_{1-6}$ alkyl, $C_{3-6}$ cycloalkyl, $C_{1-6}$ alkoxy and 5-6 membered heteroaryl comprising 1-3 hetero atoms, each hetero atom is independently N, O or S; or $R_{10}$ and $R_{11}$ together, with nitrogen atom they attached to, form a first 5-6 membered ring; and $R_{11}$ is H, $C_{1-6}$ alkyl, $C_{3-6}$ cycloalkyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, phenyl, 3-6 membered heterocycle and 5-6 membered heteroaryl is unsubstituted or substituted with 1-3 groups selected from the group consisting of halide, deuterium, —CN, —OH, —$CF_3$, $C_{1-6}$ alkyl, $C_{3-6}$ cycloalkyl, $C_{1-6}$ alkoxy and 5-6 membered heteroaryl comprising 1-3 hetero atoms, each hetero atom is independently N, O or S; or $R_{10}$ and $R_{11}$ together, with nitrogen atom they attached to, form a first 5-6 membered ring.

10. A pharmaceutical composition comprising a therapeutically effective amount of a compound of claim 1 and a pharmaceutically acceptable carrier or diluent.

11. A method for treating a cell death-related disorder in a mammal suffering therefrom, comprising administering to the mammal a therapeutically effective amount of at least one compound of claim 1, or a pharmaceutical composition thereof, wherein the cell death-related disorder is systematic inflammatory response, tumor, cancer, metabolic diseases or neurodegenerative diseases.

12. The compound of claim 5 having a Formula Ia:

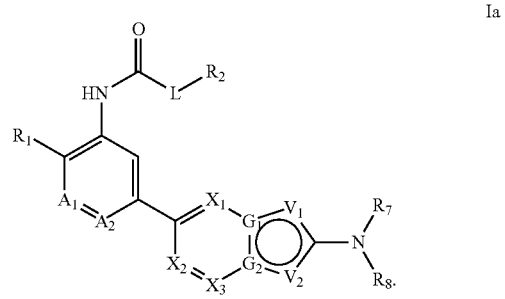

or a pharmaceutically acceptable salt, solvate, stereoisomer or a tautomer thereof, wherein at least one of $A_1$ and $A_2$ is N, L is O, NH or $CH_2$;

$R_2$ is $C_{1-6}$ alkyl, $C_{3-8}$ cycloalkyl, $C_{6-12}$ spirocycle, phenyl, 5-6 membered heteroaryl comprising 1-3 hetero atoms, 3-8 membered heterocycle comprising 1-3 hetero atoms, or 6-12 membered heterospirocycle comprising 1-3 hetero atoms, all of which are unsubstituted or substituted with 1-3 $R_9$, wherein each hetero atom is independently N, O or S;

$R_7$ is H; and $R_8$ is $C(O)R_{10}$, $C(O)NR_{10}R_{11}$, $C(O)OR_{10}$, $S(O)_2R_{10}$, or $S(O)_2NR_{10}R_{11}$.

13. The compound of claim 12, wherein $R_{10}$ is $C_{1-6}$ alkyl, $C_{3-6}$ cycloalkyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, phenyl, 3-6 membered heterocycle and 5-6 membered heteroaryl is unsubstituted or substituted with 1-3 groups selected from the group consisting of halide, deuterium, —CN, —OH, —$CF_3$, $C_{1-6}$ alkyl, $C_{3-6}$ cycloalkyl, $C_{1-6}$ alkoxy and 5-6 membered heteroaryl comprising 1-3 hetero atoms, each hetero atom is independently N, O or S; or $R_{10}$ and $R_{11}$ together, with nitrogen atom they attached to, form a first 5-6 membered ring; and $R_{11}$ is H, $C_{1-6}$ alkyl, $C_{3-6}$ cycloalkyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, phenyl, 3-6 membered heterocycle and 5-6 membered heteroaryl is unsubstituted or substituted with 1-3 groups selected from the group consisting of halide, deuterium, —CN, —OH, —$CF_3$, $C_{1-6}$ alkyl, $C_{3-6}$ cycloalkyl, $C_{1-6}$ alkoxy and 5-6 membered heteroaryl comprising 1-3 hetero atoms, each hetero atom is independently N, O or S; or $R_{10}$ and $R_{11}$ together, with nitrogen atom they attached to, form a first 5-6 membered ring.

14. A pharmaceutical composition comprising a therapeutically effective amount of a compound of claim 2 and a pharmaceutically acceptable carrier or diluent.

15. A method for treating a cell death-related disorder in a mammal suffering therefrom, comprising administering to the mammal a therapeutically effective amount of at least one compound of claim 2, or a pharmaceutical composition thereof, wherein the cell death-related disorder is systematic inflammatory response, tumor, cancer, metabolic diseases or neurodegenerative diseases.

16. A pharmaceutical composition comprising a therapeutically effective amount of a compound of claim 5 and a pharmaceutically acceptable carrier or diluent.

17. A method for treating a cell death-related disorder in a mammal suffering therefrom, comprising administering to the mammal a therapeutically effective amount of at least one compound of claim 5, or a pharmaceutical composition thereof, wherein the cell death-related disorder is systematic inflammatory response, tumor, cancer, metabolic diseases or neurodegenerative diseases.

18. A pharmaceutical composition comprising a therapeutically effective amount of a compound of claim 7 and a pharmaceutically acceptable carrier or diluent.

19. A method for treating a cell death-related disorder in a mammal suffering therefrom, comprising administering to the mammal a therapeutically effective amount of at least one compound of claim 7, or a pharmaceutical composition thereof, wherein the cell death-related disorder is systematic inflammatory response, tumor, cancer, metabolic diseases or neurodegenerative diseases.

* * * * *